(12) United States Patent
Dickson, Jr. et al.

(10) Patent No.: US 7,452,887 B2
(45) Date of Patent: Nov. 18, 2008

(54) QUINOLINE- AND ISOQUINOLINE-BASED COMPOUNDS EXHIBITING ATP-UTILIZING ENZYME INHIBITORY ACTIVITY, AND COMPOSITIONS, AND USES THEREOF

(75) Inventors: John K. Dickson, Jr., Apex, NC (US); Kevin P. Williams, Chapel Hill, NC (US); Carl Nicholas Hodge, Los Gatos, CA (US)

(73) Assignee: Amphora Discovery Corporation, Durham, NC (US)

( * ) Notice: Subject to any disclaimer, the term of this patent is extended or adjusted under 35 U.S.C. 154(b) by 424 days.

(21) Appl. No.: 11/145,562

(22) Filed: Jun. 3, 2005

(65) Prior Publication Data

US 2006/0009460 A1    Jan. 12, 2006

Related U.S. Application Data

(60) Provisional application No. 60/577,224, filed on Jun. 4, 2004.

(51) Int. Cl.
*A61K 31/496* (2006.01)
*A61K 31/4709* (2006.01)
*C07D 401/10* (2006.01)

(52) U.S. Cl. .................. 514/253.06; 514/310; 514/313; 544/363; 546/143; 546/160

(58) Field of Classification Search ........................ None
See application file for complete search history.

(56) References Cited

U.S. PATENT DOCUMENTS

| | | | |
|---|---|---|---|
| 6,207,669 B1 | 3/2001 | Cockerill et al. | |
| 6,274,596 B1 | 8/2001 | Lam et al. | |
| 6,391,874 B1 | 5/2002 | Cockerill et al. | |
| 6,713,485 B2 | 3/2004 | Carter et al. | |
| 6,723,726 B1 | 4/2004 | Cockerill et al. | |
| 6,727,256 B1 | 4/2004 | Carter et al. | |
| 2002/0048271 A1 | 4/2002 | Rastinejad et al. | |
| 2003/0176451 A1 | 9/2003 | Carter et al. | |
| 2003/0220357 A1 | 11/2003 | Bankston et al. | |
| 2004/0053942 A1 | 3/2004 | Alberti et al. | |

FOREIGN PATENT DOCUMENTS

| | | |
|---|---|---|
| WO | WO 96/18615 | 6/1996 |
| WO | WO 97/03069 | 1/1997 |
| WO | WO 98/02434 | 1/1998 |
| WO | WO 01/72711 A1 | 10/2001 |
| WO | WO 02/076976 A2 | 10/2002 |

OTHER PUBLICATIONS

Dixon et al, Journal of Chemical and Information Computer Sciences, 1998, vol. 38, pp. 1192-1203.*
International Search Report mailed Aug. 30, 2005 for international application No. PCT/US05/19255, filed Jun. 3, 2005.
International Preliminary Report on Patentability issued Dec. 4, 2006 for international application No. PCT/US05/19255, filed Jun. 3, 2005.

* cited by examiner

*Primary Examiner*—Zinna N Davis
(74) *Attorney, Agent, or Firm*—Finnegan, Henderson, Farabow, Garrett & Dunner LLP

(57) ABSTRACT

Quinoline- and isoquinoline-based compounds exhibiting ATP-utilizing enzyme inhibitory activity, methods of using compounds exhibiting ATP-utilizing enzyme inhibitory activity, and compositions comprising compounds exhibiting ATP-utilizing enzyme inhibitory activity, are disclosed.

42 Claims, No Drawings

QUINOLINE- AND ISOQUINOLINE-BASED COMPOUNDS EXHIBITING ATP-UTILIZING ENZYME INHIBITORY ACTIVITY, AND COMPOSITIONS, AND USES THEREOF

This application claims the benefit of U.S. Provisional Patent Application No. 60/577,224, filed Jun. 4, 2004; which is incorporated herein by reference for all purposes.

Protein kinases encompass a large family of functionally and structurally related enzymes that are responsible for the control of a wide variety of cellular processes including signal transduction, metabolism, transcription, cell cycle progression, cytoskeletal rearrangement and cell movement, apoptosis, and differentiation. In general, protein kinases control protein activity by catalyzing the addition of a negatively charged phosphate group from a phosphate-containing molecule such as cyclic adenosine monophosphate (cAMP), adenosine diphosphate (ADP), and ATP, to other proteins. Protein phosphorylation in turn can modulate or regulate the functioning of a target protein. Protein phosphorylation is known to play a role in intercellular communication during development, in physiological responses and in homeostasis, and in the functioning of the nervous and immune systems.

The unregulated phosphorylation of proteins is known to be a cause of, or associated with the etiology of major diseases, such as Alzheimer's disease, stroke, diabetes, obesity, inflammation, cancer, and rheumatoid arthritis. Deregulated protein kinase activity and over expression of protein kinases has been implicated in the pathophysiology of a number of important human disorders. Furthermore, genetic mutations in protein kinases are implicated in a number of disorders and many toxins and pathogens exert their effects by altering the phosphorylation of intracellular proteins.

ATP-utilizing enzymes, such as protein kinases, therefore, represent a broad class of pharmacological targets of interest for the treatment of human disease. Most human protein kinases can further be grouped into seven major groups based on the deoxyribonucleic acid (DNA) sequence homologies identified as CAMK (calcium/calmodulin-dependent protein kinases), AGC (including PKA (protein kinase A), PKG (protein kinase G), PKC (protein kinase C) kinases), CK1 (casein kinases), CMGC (containing CDK (cyclin-dependent)), MAPK (mitogen activated), GSK3 (glycogen synthase) and CLK (CDC2-like) kinases), STE (homologs of yeast Sterile 7, Sterile 11, and Sterile 20 kinases), TK (tyrosine kinases), and TKL (tyrosine-kinase like).

The AGC protein kinase family includes AKT1, AKT2, AKT3, AURORA-A, MSK1, MSK2, P70S6K, PAK1, PKA, ROCK2, SGK1, PDK1, and RSK2 protein kinases. The CMGC protein kinase family includes the CDK1, CDK2/cyclinA, CDK2/cyclinE, CDK5, DYRK2, GSK3-α, GSK3-β, p38-α, p38-β, p38-δ, and p38-γ, and MAPK1 protein kinases. The CAMK protein kinase family includes the DAPK1, MAPKAPK2, MAPKAPK3, CHEK1, CHEK2, PRAK, c-TAK1, and PIM-1-kinase protein kinases. The TK protein kinase family includes the ABL1, CSK, FLT3, FYN, HCK, INSR, KIT, LCK, PDGFRR-α, LYNA, SYK, and SRC protein kinases. The STE protein kinase family includes PAK2 protein kinase.

Chronic and excessive production of the proinflammatory cytokines tumor necrosis factor-α (TNFα) and interleukin-1β (IL-1β) are thought to be important in the progression of many inflammatory and autoimmune diseases including Crohn's disease, psoriasis and rheumatoid arthritis. Activation of the p38 MAPK pathway by a variety of cellular stresses can be a key regulator in the production of TNFα and IL-1β and the p38 MAP kinase has been targeted as an important anti-inflammatory therapeutic target. p38 MAPK pathway regulated diseases include Crohn's disease, rheumatoid arthritis, psoriasis, inflammatory bowel disease, ulcerative colitis, sepsis, asthma, osteoporosis, chronic obstructive pulmonary disease, acute coronary syndrome, stroke, atherolsclerosis, renal disease, Alzheimer's disease, and cancer. MAPKAPK2 is also a kinase in the p38 MAPK pathway and can be directly activated by p38 MAPK. Mouse knockout studies of MAPKAPK2 show a reduction in cytokine production and increase survival upon LPS challenge suggesting MAPKAPK2 can be a key regulator of the inflammatory response and can also be a potential target for anti-inflammatory therapy.

The identification and development of chemical entities that inhibit the functioning of ATP-utilizing enzymes is therefore of considerable interest.

Provided is at least one chemical entity chosen from compounds of Formula 1

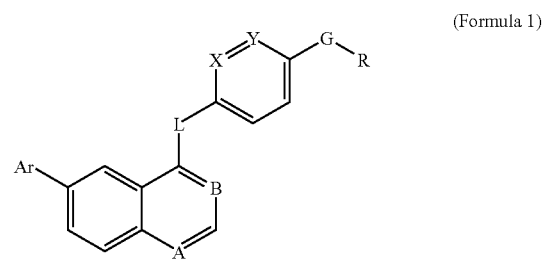

(Formula 1)

and pharmaceutically acceptable salts, solvates, chelates, non-covalent complexes, prodrugs, and mixtures thereof, wherein:

Ar is chosen from aryl, substituted aryl, heteroaryl, and substituted heteroaryl;

A is —N— and B is —CH—, or A is —CH— and B is —N—;

L is chosen from $NR^1$ and O;

$R^1$ is chosen from H, alkyl, substituted alkyl, cycloalkyl, substituted cycloalkyl, heterocycloalkyl, and substituted heterocycloalkyl;

X and Y are independently chosen from CH and N;

G is chosen from a covalent bond and $NR^6$;

$R^6$ is chosen from hydrogen and optionally substituted alkyl; and

R is chosen from optionally substituted heterocycloalkyl, with the proviso that when Ar is phenyl, A is —N—, B is —CH—, L is $NR^1$, $R^1$ is H, X is CH, Y is CH, and G is a covalent bond, then R is not 4-methylpiperazin-1-yl.

Also provided is a pharmaceutical composition comprising at least one pharmaceutically acceptable excipient, and a therapeutically effective amount of at least one chemical entity described herein.

Also provided is a method of treating a disease regulated by at least one ATP-utilizing enzyme in a subject in need of such treatment comprising administering to the patient a therapeutically effective amount of at least one chemical entity described herein.

Also provided is a method of inhibiting at least one ATP-utilizing enzyme in a subject comprising administering to the subject at least one chemical entity described herein.

Also provided is the use, in the manufacture of a medicament for treating a disease chosen from Alzheimer's disease, stroke, diabetes, obesity, inflammation, and cancer, of a chemical entity described herein.

Additional embodiments of the invention are set forth in the description which follows, or may be learned by practice of the invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements. At the very least, and not as an attempt to limit the application of the doctrine of equivalents to the scope of the claims, each numerical parameter as set forth in the claims should at least be construed in light of the number of reported significant digits and by applying ordinary rounding techniques.

As used herein, when any variable occurs more than one time in a chemical formula, its definition on each occurrence is independent of its definition at every other occurrence. In accordance with the usual meaning of "a" and "the" in patents, reference, for example, to "a" kinase or "the" kinase is inclusive of one or more kinases.

A dash ("-") that is not between two letters or symbols is used to indicate a point of attachment for a substituent. For example, —CONH$_2$ is attached through the carbon atom.

"Acyl" refers to a radical —C(O)R, where R is hydrogen, alkyl, substituted alkyl, substituted cycloalkyl, substituted heterocycloalkyl, substituted aryl, or substituted heteroaryl group as defined herein. Representative examples include, but are not limited to, formyl, acetyl, cylcohexylcarbonyl, cyclohexylmethylcarbonyl, benzoyl, benzylcarbonyl, and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms.

"Alkoxy" refers to a radical —OR where R represents an alkyl, substituted alkyl, substituted cycloalkyl, substituted heterocycloalkyl, substituted aryl, or substituted heteroaryl group as defined herein. Representative examples include, but are not limited to, methoxy, ethoxy, propoxy, butoxy, cyclohexyloxy, and the like.

"Alkoxycarbonyl" refers to a radical —C(O) alkoxy where alkoxy is as defined herein.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methylpropan-1-yl, 2-methyl-propan-2-yl, cyclobutan-1-yl, and the like. In certain embodiments, an alkyl group comprises from 1 to 20 carbon atoms. In other embodiments, an alkyl group comprises from 1 to 6 carbon atoms, and is referred to as a lower alkyl group.

"Sulfonyl" refers to a radical —S(O)$_2$R where R is an alkyl, substituted alkyl, substituted cycloalkyl, substituted heterocycloalkyl, substituted aryl, or substituted heteroaryl group as defined herein. Representative examples include, but are not limited to methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocycloalkyl, substituted aryl, or substituted heteroaryl group as defined herein that may be optionally substituted as defined herein. Representative examples include, but are not limited to, methylthio, ethylthio, propylthio, butylthio, and the like.

"Amino" refers to the radical —NH$_2$.

The term "substituted amino" refers to the group —NHR$^d$ or —NR$^d$R$^d$ where each R$^d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, and sulfonyl.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene;

bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 6 to 20 carbon atoms. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkyl, arylalkenyl, and/or arylalkynyl is used. In certain embodiments, an arylalkyl group can be (C$_{6-30}$) arylalkyl, e.g., the alkyl group of the arylalkyl group can be (C$_{1-10}$) and the aryl moiety can be (C$_{5-20}$).

"Carbonyl" refers to a radical —C(O) group.

"Carboxy" refers to the radical —C(O)OH.

When the chemical structure and chemical name conflict, the chemical structure is determinative of the identity of the compound. The chemical entities of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Further, when partial structures of the chemical entities of the present disclosure are illustrated, asterisks indicate the point of attachment of the partial structure to the rest of the molecule. Enantiomeric and stereoisomeric mixtures can be resolved into the component enantiomers or stereoisomers using separation techniques or chiral synthesis techniques well known to the skilled artisan.

Compounds of Formula 1 include, but are not limited to optical isomers of compounds of Formula 1, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula 1 include Z- and E-forms (or cis- and trans-forms) of compounds with double bonds. Where compounds of Formula 1 exists in various tautomeric forms, chemical entities of the present invention include all tautomeric forms of the compound.

Chemical entities of the present disclosure include, but are not limited to compounds of Formula 1 and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, solvates, crystal forms, chelates, non-covalent complexes, prodrugs, and mixtures thereof.

As noted above, prodrugs also fall within the scope of chemical entities, for example ester or amide derivatives of the compounds of Formula 1. The term "prodrugs" includes any compounds that become compounds of Formula 1 when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula 1.

The term "solvate" refers to the compound formed by the interaction of a solvent and a compound. Suitable solvates are pharmaceutically acceptable solvates, such as hydrates, including monohydrates and hemi-hydrates.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Heterocycloalkyl" refers to a saturated or unsaturated, but non-aromatic, cyclic alkyl group in which one or more carbon atoms (and any associated hydrogen atoms) are independently replaced with the same or different heteroatom. Typical heteroatoms to replace the carbon atom(s) include, but are not limited to, N, P, O, S, and Si. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like. Substituted heterocycloalkyl also includes ring systems substituted with one or more oxo (=O) or oxide (—O⁻) substituents, such as piperidinyl N-oxide, morpholinyl-N-oxide, 1-oxo-1-thiomorpholinyl and 1,1-dioxo-1-thiomorpholinyl.

"Disease" refers to any disease, disorder, condition, symptom, or indication.

"Enzyme" refers to any naturally occurring or synthetic macromolecular substance composed wholly or largely of protein, that catalyzes, more or less specifically, one or more biochemical reactions. The substances upon which the enzyme acts are referred to "substrates," for which the enzyme possesses a specific binding or "active site," or "catalytic domain." Enzymes can also act on macromolecular structures such as muscle fibers.

"Extended release" refers to dosage forms that provide for the delayed, slowed, over a period of time, continuous, discontinuous, or sustained release of the compounds of the present disclosure.

"Halo" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses:

5- to 7-membered aromatic, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heteroarylalkyl" or "heteroaralkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkanyl, alkenyl or alkynyl moiety of the heteroarylalkyl can be 1 to 10 membered and the heteroaryl moiety can be a 5 to 20-membered heteroaryl.

"Leaving group" refers to an atom or a group capable of being displaced by a nucleophile and includes halo, such as chloro, bromo, fluoro, and iodo, alkoxycarbonyl (e.g., acetoxy), aryloxycarbonyl, mesyloxy, tosyloxy, trifluoromethanesulfonyloxy, aryloxy (e.g., 2,4-dinitrophenoxy), methoxy, N,O-dimethylhydroxylamino, and the like.

"Optional" or "optionally" means that the subsequently described event or circumstance may but need not occur, and that the description includes instances where the event or circumstance occurs and instances in which the event does not.

"Pharmaceutically acceptable" refers to approved or approvable by a regulatory agency of the Federal or a state government or listed in the U.S. Pharmacopeia or other generally recognized pharmacopeia for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient, carrier or adjuvant" refers to an excipient, carrier or adjuvant that can be administered to a subject, together with a at least one chemical of the present disclosure, and which does not destroy the pharmacological activity thereof and is nontoxic when administered in doses sufficient to deliver a therapeutic amount of the at least one chemical entity.

"Pharmaceutically acceptable vehicle" refers to a diluent, adjuvant, excipient or carrier with which at least one chemical entity of the present disclosure is administered.

"Promoiety" refers to a form of protecting group that when used to mask a functional group within a drug molecule converts the drug into a prodrug. For example, the promoiety can be attached to the drug via bond(s) that are cleaved (or broken) by enzymatic or non-enzymatic means in vivo.

"Protecting group" refers to a grouping of atoms that when attached to a reactive group in a molecule masks, reduces or prevents that reactivity. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitro-veratryloxycarbonyl ("NVOC"), and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Protein kinase" and "kinase" refers to any enzyme that phosphorylates one or more hydroxyl or phenolic groups in proteins, ATP being the phosphoryl-group donor.

"Stereoisomer" refers to an isomer that differs in the arrangement of the constituent atoms in space. Stereoisomers that are mirror images of each other and optically active are termed "enantiomers," and stereoisomers that are not mirror images of one another are termed "diastereoisomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, —X, —$R^{33}$, —$O^-$, =O, —$OR^{33}$, —$SR^{33}$, —$S^-$, =S, —$NR^{33}R^{34}$, —$NR^{33}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{33}$, —$OS(O_2)O^-$, —$OS(O)_2R^{33}$, —$P(O)(O^-)_2$, —$P(O)(OR^{33})(O^-)$, —$OP(O)(OR^{33})(OR^{34})$, —$C(O)R^{33}$, —$C(S)R^{33}$, —$C(O)OR^{33}$, —$C(O)NR^{33}R^{34}$, —$C(O)O^-$, —$C(S)OR^{33}$, —$NR^{35}C(O)NR^{33}R^{34}$, —$NR^{35}C(S)NR^{33}R^{34}$, —$NR^{35}C(NR^{33})NR^{33}R^{34}$, —$C(NR^{33})NR^{33}R^{34}$, —$S(O)_2NR^{33}R^{34}$, —$NR^{35}S(O)_2R^{33}$, —$NR^{35}C(O)R^{33}$, and —$S(O)R^{33}$ where each X is independently a halo; each $R^{33}$ and $R^{34}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, —$NR^{35}R^3$, —$C(O)R^{35}$ or —$S(O)_2R^{35}$ or optionally $R^{33}$ and $R^{34}$ together with the atom to which $R^{33}$ and $R^{34}$ are attached form one or more cycloheteroalkyl, substituted cycloheteroalkyl, heteroaryl, or substituted heteroaryl rings; and $R^{35}$ and $R^{36}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl or substituted heteroarylalkyl, or optionally $R^{35}$ and $R^{36}$ together with the nitrogen atom to which $R^{35}$ and $R^{36}$ are attached form one or more cycloheteroalkyl, substituted cycloheteroalkyl, heteroaryl, or substituted heteroaryl rings. In certain embodiments, a tertiary amine or aromatic nitrogen may be substituted with on or more oxygen atoms to form the corresponding nitrogen oxide.

In certain embodiments, substituted aryl and substituted heteroaryl include one or more of the following substitute groups: F, Cl, Br, $C_{1-3}$ alkyl, substituted alkyl, $C_{1-3}$ alkoxy, —S(O)$_2$NR$^{33}$R$^{34}$, —NR$^{33}$R$^{34}$, —CF$_3$, —OCF$_3$, —CN, —NR$^{35}$S(O)$_2$R$^{33}$, —NR$^{35}$C(O)R$^{33}$, $C_{5-10}$ aryl, substituted $C_{5-10}$ aryl, $C_{5-10}$ heteroaryl, substituted $C_{5-10}$ heteroaryl, —C(O)OR$^{33}$, —NO$_2$, —C(O)R$^{33}$, —C(O)NR$^{33}$R$^{34}$, —OCHF$_2$, $C_{1-3}$ acyl, —SR$^{33}$—S(O)$_2$OH, —S(O)$_2$R$^{33}$, —S(O)R$^{33}$, —C(S)R$^{33}$, —C(O)O$^-$, —C(S)OR$^{33}$, —NR$^{35}$C(O)NR$^{33}$R$^{34}$—NR$^{35}$C(S)NR$^{33}$R$^{34}$, and —C(NR$^{35}$)NR$^{33}$R$^{34}$, $C_{3-8}$ cycloalkyl, and substituted $C_{3-8}$ cycloalkyl, as defined herein.

In certain embodiments, substituted arylalkyl, and substituted heteroarylalkyl include one or more of the following substitute groups: F, Cl, Br, $C_{1-3}$ alkyl, $C_{1-3}$ alkoxy, —S(O)$_2$NR$^{33}$R$^{34}$, —NR$^{33}$R$^{34}$, —CF$_3$, —OCF$_3$, CN, —NR$^{35}$S(O)$_2$R$^{33}$, —NR$^{35}$C(O)R$^{33}$, $C_{5-10}$ aryl, substituted alkyl, substituted $C_{5-10}$ aryl, $C_{5-10}$ heteroaryl, substituted $C_{5-10}$ heteroaryl, —C(O)OR$^{33}$, —N$_2$, —C(O)R$^{33}$, C(O)NR$^{33}$R$^{34}$, —OCHF$_2$, $C_{1-3}$ acyl, —SR$^{33}$, —S(O)$_2$OH, —S(O)$_2$R$^{33}$, —S(O)R$^{33}$, —C(S)R$^{33}$, —C(O)O$^-$, —C(S)OR$^{33}$, —NR$^{35}$C(O)NR$^{33}$R$^{34}$, —NR$^{35}$C(S)NR$^{33}$R$^{34}$, and —C(NR$^{35}$)NR$^{33}$R$^{34}$, $C_{3-8}$ cycloalkyl, and substituted $C_{3-8}$ cycloalkyl, as defined herein.

In certain embodiments, substituted alkyl, substituted cycloalkyl, and substituted heterocycloalkyl includes one or more of the following substitute groups: $C_{1-3}$ alkoxy, —NR$^{33}$R$^{34}$, substituted $C_{5-10}$ heteroaryl, —SR$^{33}$, $C_{1-3}$ alkoxy, —S(O)$_2$ NR$^{33}$R$^{34}$, CN, F, Cl, —CF$_3$, —OCF$_3$, —NR$^{35}$S(O)$_2$R$^{33}$, —NR$^{35}$C(O)R$^{33}$, $C_{5-10}$ aryl, substituted $C_{5-10}$ aryl, $C_{5-10}$ heteroaryl, substituted $C_{5-10}$ heteroaryl, —C(O)OR$^{33}$, —N$_2$, —C(O)R$^{33}$, C(O)NR$^{33}$R$^{34}$, —OCHF$_2$, $C_{1-3}$ acyl, —S(O)$_2$OH, —S(O)$_2$R$^{33}$, —S(O)R$^{33}$, —C(S)R, —C(O)O$^-$, —C(S)OR$^{33}$—NR$^{35}$C(O)NR$^{33}$R$^{34}$—NR$^{35}$C(S)NR$^{33}$R$^{34}$ and —C(NR$^{35}$)NR$^{33}$R$^{34}$, $C_{3-8}$ cycloalkyl, and substituted $C_{3-8}$ cycloalkyl, as defined herein.

In certain embodiments, substituted alkenyl includes one or more of the following substitute groups: $C_{1-8}$ alkyl, substituted $C_{1-8}$ alkyl, $C_{5-10}$ aryl, substituted $C_{5-10}$ aryl, $C_{5-10}$ heteroaryl, substituted $C_{5-10}$ heteroaryl, $C_{3-8}$ cycloalkyl, substituted $C_{3-8}$ cycloalkyl, cycloheteroalkylalkyl, and substituted cycloheteroalkylalkyl, as defined herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Therapeutically effective dosage" refers to a dosage that provides effective treatment of a condition and/or disease in a subject. The therapeutically effective dosage can vary somewhat from compound to compound, and from subject to subject, and can depend upon factors such as the condition of the subject and the route of delivery. A therapeutically effective dosage can be determined in accordance with routine pharmacological procedures known to those skilled in the art.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and inhibit at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

The compounds of Formula 1 can be named and numbered in the manner (e.g., using ChemDraw Ultra 9.0 Struct=Name algorithm) described below. For example, the compound:

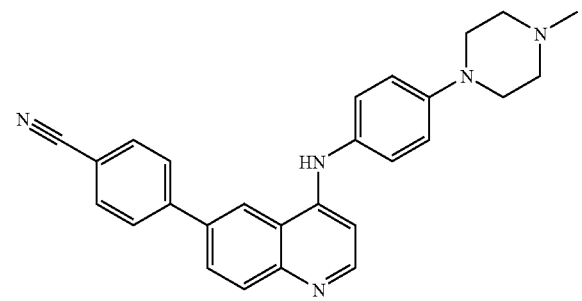

i.e., the compound according to Formula 1 where Ar is 4-cyanophenyl, A is N, B is CH, L is NR$^1$, R$^1$ is H, X is CH, Y is CH, G is a covalent bond, and R is 4-methylpiperazin-1-yl) can be named 4-(4-(4-(4-methylpiperazin-1-yl)phenylamino)quinolin-6-yl)benzonitrile.

Provided is at least one chemical entity chosen from compounds of Formula 1

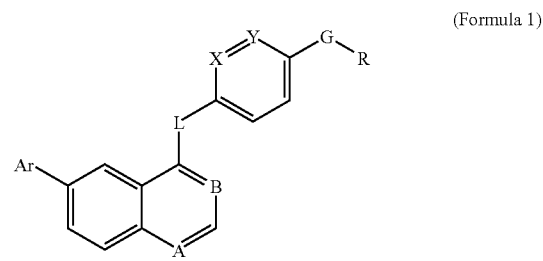

(Formula 1)

and pharmaceutically acceptable salts, solvates, chelates, non-covalent complexes, prodrugs, and mixtures thereof, wherein:

Ar is chosen from aryl, substituted aryl, heteroaryl, and substituted heteroaryl;

A is —N— and B is —CH—, or A is —CH— and B is —N—;

L is chosen from NR$^1$ and O;

R¹ is chosen from H, alkyl, substituted alkyl, cycloalkyl, substituted cycloalkyl, heterocycloalkyl, and substituted heterocycloalkyl;

X and Y are independently chosen from CH and N;

G is chosen from a covalent bond and NR⁶;

R⁶ is chosen from hydrogen and optionally substituted alkyl; and

R is chosen from optionally substituted heterocycloalkyl, with the proviso that when Ar is phenyl, A is —N—, B is —CH—, L is NR¹, R¹ is H, X is CH, Y is CH, and G is a covalent bond, then R is not 4-methylpiperazin-1-yl.

In certain embodiments, A is —N— and B is —CH—.

In certain embodiments, A is —CH— and B is —N—.

In certain embodiments, R is chosen from optionally substituted piperidinyl, optionally substituted pyrrolidinyl, and optionally substituted piperazinyl.

In certain embodiments, G is a covalent bond.

In certain embodiments, G is NR⁶.

In certain embodiments, R⁶ is chosen from hydrogen and lower alkyl.

In certain embodiments, R¹ is chosen from hydrogen, alkyl, and substituted alkyl. In certain embodiments, R¹ is hydrogen.

In certain embodiments, Ar is chosen from aryl and substituted aryl. In certain embodiments, Ar is chosen from phenyl, substituted phenyl, and naphthyl. In certain embodiments, Ar is chosen from phenyl, and substituted phenyl. In certain embodiments, Ar is chosen from substituted phenyl.

In certain embodiments, the substituent groups on Ar are selected from halogen, —CN, —OH, —COOH, —NO₂, $C_{1-8}$ alkoxy, substituted $C_{1-8}$ alkoxy, $C_{1-8}$ alkyl, substituted $C_{1-8}$ alkyl, $C_{5-10}$ aryl, substituted $C_{5-0}$ aryl, $C_{5-10}$ cycloalkyl, substituted $C_{5-10}$ cycloalkyl, $C_{1-8}$ alkylthio, substituted $C_{1-8}$ alkylthio, $C_{1-8}$ alkylsulfinyl, substituted $C_{1-8}$ alkylsulfinyl, $C_{1-8}$ alkylamino, substituted $C_{1-8}$ alkylamino, $C_{1-8}$ aminocarbonyl, substituted $C_{1-8}$ aminocarbonyl, $C_{1-8}$ alkylcarbonylamino, substituted $C_{1-8}$ alkylcarbonylamino, $C_{1-8}$ alkylsulfonyl, substituted $C_{1-8}$ alkylsulfonyl, $C_{1-8}$ alkylcarbonyl, and substituted $C_{1-8}$ alkylcarbonyl.

In certain embodiments, X is CH and Y is CH.

In certain embodiments, X is CH and Y is N.

In certain embodiments, X is N and Y is N.

Also provided is at least one chemical entity chosen from compounds of Formula 2:

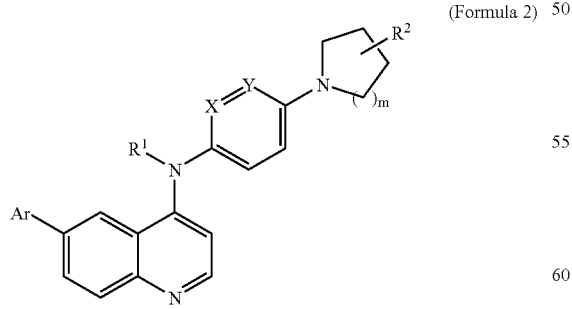

(Formula 2)

and pharmaceutically acceptable salts, solvates, chelates, non-covalent complexes, prodrugs, and mixtures thereof, wherein Ar, R¹, X, and Y are as described for compounds of Formula 1 and wherein m is an integer chosen from 1, 2, and 3; and R² is chosen from 14, alkyl, substituted alkyl, cycloalkyl, substituted cycloalkyl, heterocycloalkyl, substituted heterocycloalkyl, aryl, substituted aryl, heteroaryl, and substituted heteroaryl.

In certain embodiments, R² is chosen from H, alkyl, substituted alkyl, cycloalkyl, substituted cycloalkyl, and —NR⁴R⁵, wherein R⁴ and R⁵ are independently chosen from H, alkyl, and substituted alkyl; and when R² is attached to a carbon α to the ring nitrogen, then R² is not —NR⁴R⁵.

In certain embodiments, R² is chosen from alkyl, and substituted alkyl.

In certain embodiments, R² is independently chosen from —NR⁴R⁵ and —CH₂—NR⁴R⁵.

In certain embodiments, R² is —NR⁴R⁵ and R⁴ and R⁵ are independently chosen from $C_{1-4}$ alkyl, and substituted $C_{1-4}$ alkyl.

In certain embodiments, R² is —N(CH₃)₂.

In certain embodiments, m is 1. In certain embodiments, m is 2. In certain embodiments, m is 3.

Also provided is at least one chemical entity chosen from compounds of Formula 3:

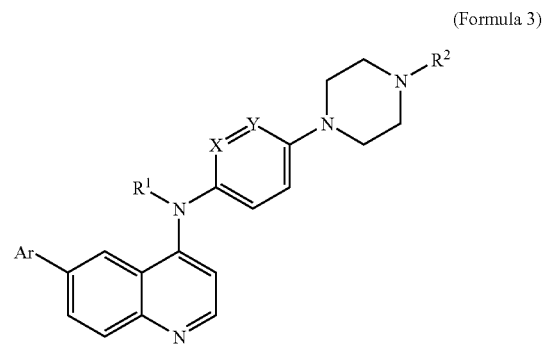

(Formula 3)

and pharmaceutically acceptable salts, solvates, chelates, non-covalent complexes, prodrugs, and mixtures thereof, wherein Ar, R¹, X, Y, and R² are as described for compounds of Formula 2.

Also provided is at least one chemical entity chosen from compounds of Formula 4:

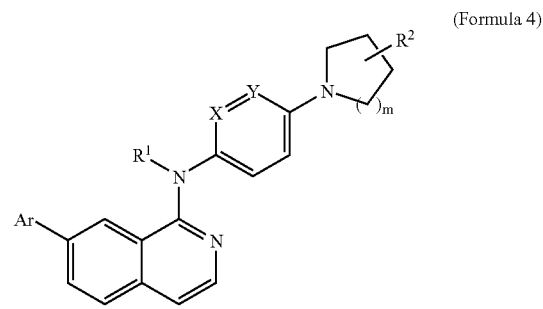

(Formula 4)

and pharmaceutically acceptable salts, solvates, chelates, non-covalent complexes, prodrugs, and mixtures thereof, wherein Ar, R¹, X, Y, m and R² are as described for compounds of Formula 2.

Also provided is at least one chemical entity chosen from compounds of Formula 5:

(Formula 5)

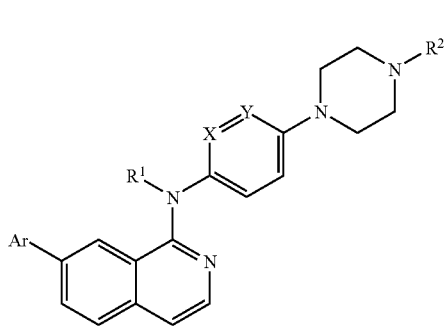

and pharmaceutically acceptable salts, solvates, chelates, non-covalent complexes, prodrugs, and mixtures thereof, wherein Ar, $R^1$, X, Y, and $R^2$ are as described for compounds of Formula 2.

Also provided is at least one chemical entity chosen from compounds of Formula 6:

(Formula 6)

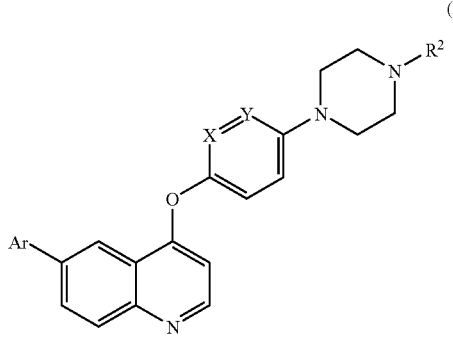

and pharmaceutically acceptable salts, solvates, chelates, non-covalent complexes, prodrugs, and mixtures thereof, wherein Ar, X, Y, and $R^2$ are as described for compounds of Formula 5.

Also provided is at least one chemical entity chosen from compounds of Formula 7:

(Formula 7)

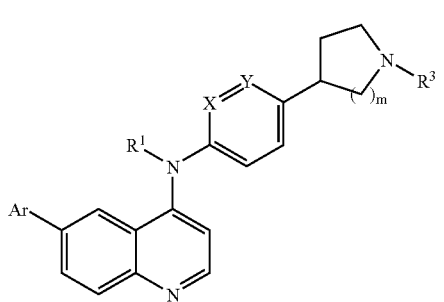

and pharmaceutically acceptable salts, solvates, chelates, non-covalent complexes, prodrugs, and mixtures thereof, wherein Ar, $R^1$, X, and Y are as described for compounds of Formula 1, wherein
m is an integer chosen from 1, 2, and 3; and
$R^3$ is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

In certain embodiments, m is 1. In certain embodiments, m is 2. In certain embodiments, m is 3.

In certain embodiments, $R^3$ is chosen from H, alkyl, substituted alkyl, cycloalkyl, substituted cycloalkyl, aryl, substituted aryl, heteroaryl, and substituted heteroaryl.

In certain embodiments, $R^3$ is chosen from H, alkyl, and substituted alkyl.

In certain embodiments, $R^3$ is chosen from $C_{1-4}$ alkyl, and substituted $C_{1-4}$ alkyl.

Also provided is at least one chemical entity chosen from compounds of Formula 8:

(Formula 8)

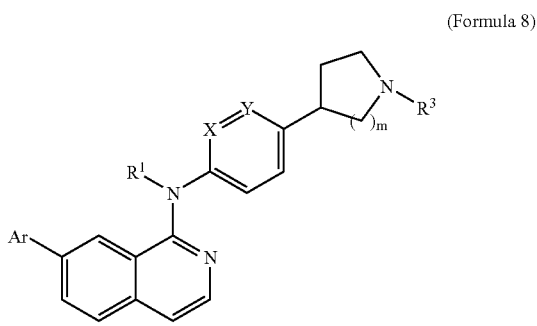

and pharmaceutically acceptable salts, solvates, chelates, non-covalent complexes, prodrugs, and mixtures thereof, wherein Ar, $R^1$, X, Y, m and $R^3$ are as described for compounds of Formula 7.

Also provided is at least one chemical entity chosen from compounds of Formula 9:

(Formula 9)

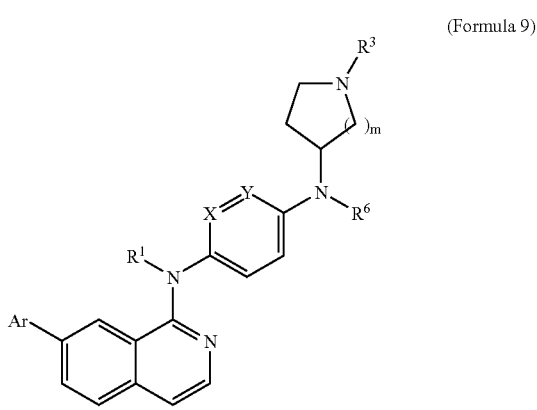

and pharmaceutically acceptable salts, solvates, chelates, non-covalent complexes, prodrugs, and mixtures thereof, wherein Ar, $R^1$, X, Y, and $R^6$ are as described for compounds of Formula 1 and m and $R^3$ are as described for compounds of Formula 7.

Also provided is at least one chemical entity chosen from compounds of Formula 10:

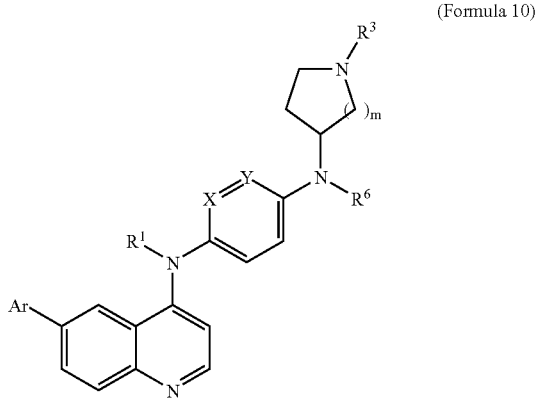

(Formula 10)

and pharmaceutically acceptable salts, solvates, chelates, non-covalent complexes, prodrugs, and mixtures thereof, wherein Ar, $R^1$, X, Y, and $R^6$ are as described for compounds of Formula 1 and m and $R^3$ are as described for compounds of Formula 7.

In certain embodiments, the compound of Formula 1 is chosen from
N-(4-(4-methylpiperazin-1-yl)phenyl)-6-(thiophen-2-yl)quinolin-4-amine;
N-(4-(4-methylpiperazin-1-yl)phenyl)-6-(thiophen-3-yl)quinolin-4-amine;
6-(furan-2-yl)-N-(4-(4-methylpiperazin-1-yl)phenyl)quinolin-4-amine;
6-(furan-3-yl)-N-(4-(4-methylpiperazin-1-yl)phenyl)quinolin-4-amine;
N-(4-(4-methylpiperazin-1-yl)phenyl)-6-(pyridin-3-yl)quinolin-4-amine;
N-(4-(4-methylpiperazin-1-yl)phenyl)-6-(pyridin-4-yl)quinolin-4-amine;
6-(benzo[b]thiophen-3-yl)-N-(4-(4-methylpiperazin-1-yl)phenyl)quinolin-4-amine;
1-(5-(4-(4-(4-methylpiperazin-1-yl)phenylamino)quinolin-6-yl)thiophen-2-yl)ethanone;
6-(benzo[b]thiophen-2-yl)-N-(4-(4-methylpiperazin-1-yl)phenyl)quinolin-4-amine;
6-(5-chlorothiophen-2-yl)-N-(4-(4-methylpiperazin-1-yl)phenyl)quinolin-4-amine;
N-(4-(4-methylpiperazin-1-yl)phenyl)-6-(4-methylthiophen-2-yl)quinolin-4-amine;
N-(4-(4-methylpiperazin-1-yl)phenyl)-6-(pyrimidin-5-yl)quinolin-4-amine;
N-(4-(4-methylpiperazin-1-yl)phenyl)-6,8'-biquinolin-4-amine;
N-(4-(4-methylpiperazin-1-yl)phenyl)-6-(naphthalen-2-yl)quinolin-4-amine;
N-(4-(4-methylpiperazin-1-yl)phenyl)-6-(naphthalen-1-yl)quinolin-4-amine;
4-(4-(methyl(4-(4-methylpiperazin-1-yl)phenyl)amino)quinolin-6-yl)benzonitrile;
4-(4-((4-(4-methylpiperazin-1-yl)phenyl)(propyl)amino)quinolin-6-yl)benzonitrile;
N-(4-(4-methylpiperazin-1-yl)phenyl)-6-phenylquinolin-4-amine;
6-(3-chlorophenyl)-N-(4-(4-methylpiperazin-1-yl)phenyl)quinolin-4-amine;
6-(4-chlorophenyl)-N-(4-(4-methylpiperazin-1-yl)phenyl)quinolin-4-amine;
N-(4-(4-methylpiperazin-1-yl)phenyl)-6-o-tolylquinolin-4-amine;
N-(4-(4-methylpiperazin-1-yl)phenyl)-6-m-tolylquinolin-4-amine;
N-(4-(4-methylpiperazin-1-yl)phenyl)-6-p-tolylquinolin-4-amine;
6-(2-methoxyphenyl)-N-(4-(4-methylpiperazin-1-yl)phenyl)quinolin-4-amine;
6-(3-methoxyphenyl)-N-(4-(4-methylpiperazin-1-yl)phenyl)quinolin-4-amine;
6-(4-methoxyphenyl)-N-(4-(4-methylpiperazin-1-yl)phenyl)quinolin-4-amine;
2-(4-(4-(4-methylpiperazin-1-yl)phenylamino)quinolin-6-yl)benzamide;
3-(4-(4-(4-methylpiperazin-1-yl)phenylamino)quinolin-6-yl)benzonitrile;
4-(4-(4-(4-methylpiperazin-1-yl)phenylamino)quinolin-6-yl)benzonitrile;
6-(3,4-dimethoxyphenyl)-N-(4-(4-methylpiperazin-1-yl)phenyl)quinolin-4-amine;
6-(2,4-difluorophenyl)-N-(4-(4-methylpiperazin-1-yl)phenyl)quinolin-4-amine;
6-(4-fluoro-3-methylphenyl)-N-(4-(4-methylpiperazin-1-yl)phenyl)quinolin-4-amine;
(3-(4-(4-(4-methylpiperazin-1-yl)phenylamino)quinolin-6-yl)phenyl)methanol;
6-(5-fluoro-2-methoxyphenyl)-N-(4-(4-methylpiperazin-1-yl)phenyl)quinolin-4-amine;
3-(4-(4-(4-methylpiperazin-1-yl)phenylamino)quinolin-6-yl)phenol;
6-(3-chloro-4-fluorophenyl)-N-(4-(4-methylpiperazin-1-yl)phenyl)quinolin-4-amine;
4-(4-(4-(4-methylpiperazin-1-yl)phenylamino)quinolin-6-yl)phenol;
6-(2,3-dimethylphenyl)-N-(4-(4-methylpiperazin-1-yl)phenyl)quinolin-4-amine;
6-(2,5-dimethoxyphenyl)-N-(4-(4-methylpiperazin-1-yl)phenyl)quinolin-4-amine;
6-(2-ethylphenyl)-N-(4-(4-methylpiperazin-1-yl)phenyl)quinolin-4-amine;
4-(4-(4-(4-methylpiperazin-1-yl)phenylamino)quinolin-6-yl)benzamide;
6-(4-(ethylthio)phenyl)-N-(4-(4-methylpiperazin-1-yl)phenyl)quinolin-4-amine;
6-(4-(ethylthio)phenyl)-N-(4-(4-methylpiperazin-1-yl)phenyl)quinolin-4-amine;
6-(4-(ethylthio)phenyl)-N-(4-(4-methylpiperazin-1-yl)phenyl)quinolin-4-amine;
6-(2,5-difluorophenyl)-N-(4-(4-methylpiperazin-1-yl)phenyl)quinolin-4-amine;
6-(2,5-difluorophenyl)-N-(4-(4-methylpiperazin-1-yl)phenyl)quinolin-4-amine;
6-(2,3-dichlorophenyl)-N-(4-(4-methylpiperazin-1-yl)phenyl)quinolin-4-amine;
6-(2,5-dimethylphenyl)-N-(4-(4-methylpiperazin-1-yl)phenyl)quinolin-4-amine;
3-(4-(4-(4-methylpiperazin-1-yl)phenylamino)quinolin-6-yl)benzoic acid;
N-(4-(4-methylpiperazin-1-yl)phenyl)-6-(4-(methylthio)phenyl)quinolin-4-amine;
6-(3-ethoxyphenyl)-N-(4-(4-methylpiperazin-1-yl)phenyl)quinolin-4-amine;
N-(4-(4-methylpiperazin-1-yl)phenyl)-6-(2-(trifluoromethyl)phenyl)quinolin-4-amine;

6-(3-(benzyloxy)phenyl)-N-(4-(4-methylpiperazin-1-yl)phenyl)quinolin-4-amine;
N-(4-(4-methylpiperazin-1-yl)phenyl)-6-(4-vinylphenyl)quinolin-4-amine;
6-(2,4-dimethoxyphenyl)-N-(4-(4-methylpiperazin-1-yl)phenyl)quinolin-4-amine;
N-(4-(4-methylpiperazin-1-yl)phenyl)-6-(3,4,5-trifluorophenyl)quinolin-4-amine;
(4-(4-(4-(4-methylpiperazin-1-yl)phenylamino)quinolin-6-yl)phenyl)methanol;
N-(4-(4-methylpiperazin-1-yl)phenyl)-6-(4-phenoxyphenyl)quinolin-4-amine;
6-(4-ethoxyphenyl)-N-(4-(4-methylpiperazin-1-yl)phenyl)quinolin-4-amine;
6-(3,4-dichlorophenyl)-N-(4-(4-methylpiperazin-1-yl)phenyl)quinolin-4-amine;
N-(4-(4-methylpiperazin-1-yl)phenyl)-6-(4-(trifluoromethyl)phenyl)quinolin-4-amine;
6-(2,5-dichlorophenyl)-N-(4-(4-methylpiperazin-1-yl)phenyl)quinolin-4-amine;
6-(2,4-dichlorophenyl)-N-(4-(4-methylpiperazin-1-yl)phenyl)quinolin-4-amine;
6-(3-isopropylphenyl)-N-(4-(4-methylpiperazin-1-yl)phenyl)quinolin-4-amine;
6-(4-isopropylphenyl)-N-(4-(4-methylpiperazin-1-yl)phenyl)quinolin-4-amine;
6-(4-fluoro-2-methylphenyl)-N-(4-(4-methylpiperazin-1-yl)phenyl)quinolin-4-amine;
6-(3,4-difluorophenyl)-N-(4-(4-methylpiperazin-1-yl)phenyl)quinolin-4-amine;
6-(biphenyl-3-yl)-N-(4-(4-methylpiperazin-1-yl)phenyl)quinolin-4-amine;
6-(5-isopropyl-2-methoxyphenyl)-N-(4-(4-methylpiperazin-1-yl)phenyl)quinolin-4-amine;
N-(3-(4-(4-(4-methylpiperazin-1-yl)phenylamino)quinolin-6-yl)phenyl)acetamide;
6-(2,4-bis(trifluoromethyl)phenyl)-N-(4-(4-methylpiperazin-1-yl)phenyl)quinolin-4-amine;
N-(4-(4-methylpiperazin-1-yl)phenyl)-6-(4-(methylsulfinyl)phenyl)quinolin-4-amine;
N-(4-(4-methylpiperazin-1-yl)phenyl)-6-(4-pentylphenyl)quinolin-4-amine;
6-(3,5-bis(trifluoromethyl)phenyl)-N-(4-(4-methylpiperazin-1-yl)phenyl)quinolin-4-amine;
6-(4-butylphenyl)-N-(4-(4-methylpiperazin-1-yl)phenyl)quinolin-4-amine;
3-(4-(4-(4-(4-methylpiperazin-1-yl)phenylamino)quinolin-6-yl)phenyl)propanoic acid;
N-(4-(4-methylpiperazin-1-yl)phenyl)-6-(3-nitrophenyl)quinolin-4-amine;
6-(3-fluorophenyl)-N-(4-(4-methylpiperazin-1-yl)phenyl)quinolin-4-amine;
6-(2-fluorophenyl)-N-(4-(4-methylpiperazin-1-yl)phenyl)quinolin-4-amine;
6-(4-tert-butylphenyl)-N-(4-(4-methylpiperazin-1-yl)phenyl)quinolin-4-amine;
N-(4-(4-methylpiperazin-1-yl)phenyl)-6-(3-(trifluoromethoxy)phenyl)quinolin-4-amine;
N-(4-(4-methylpiperazin-1-yl)phenyl)-6-(4-(trifluoromethoxy)phenyl)quinolin-4-amine;
6-(2,6-difluorophenyl)-N-(4-(4-methylpiperazin-1-yl)phenyl)quinolin-4-amine;
N-(4-(4-methylpiperazin-1-yl)phenyl)-6-(3-(trifluoromethyl)phenyl)quinolin-4-amine;
6-(4-(benzyloxy)phenyl)-N-(4-(4-methylpiperazin-1-yl)phenyl)quinolin-4-amine;
6-(2-((dimethylamino)methyl)phenyl)-N-(4-(4-methylpiperazin-1-yl)phenyl)quinolin-4-amine;
6-(4-(benzyloxy)-3-fluorophenyl)-N-(4-(4-methylpiperazin-1-yl)phenyl)quinolin-4-amine;
6-(4-cyclohexylphenyl)-N-(4-(4-methylpiperazin-1-yl)phenyl)quinolin-4-amine;
6-(3,4-dimethylphenyl)-N-(4-(4-methylpiperazin-1-yl)phenyl)quinolin-4-amine;
6-phenyl-N-(4-(piperazin-1-yl)phenyl)quinolin-4-amine;
N-(4-(4-ethylpiperazin-1-yl)phenyl)-6-phenylquinolin-4-amine;
6-phenyl-N-(4-(4-propylpiperazin-1-yl)phenyl)quinolin-4-amine;
N-(4-(4-butylpiperazin-1-yl)phenyl)-6-phenylquinolin-4-amine;
N-(4-(4-isopropylpiperazin-1-yl)phenyl)-6-phenylquinolin-4-amine;
N-(4-(4-(pentan-3-yl)piperazin-1-yl)phenyl)-6-phenylquinolin-4-amine;
2-(4-(4-(6-phenylquinolin-4-ylamino)phenyl)piperazin-1-yl)ethanol;
N-(4-(4-(2-methoxyethyl)piperazin-1-yl)phenyl)-6-phenylquinolin-4-amine;
3-(4-(4-(6-phenylquinolin-4-ylamino)phenyl)piperazin-1-yl)propan-1-ol;
N-(4-(4-(2-(dimethylamino)ethyl)piperazin-1-yl)phenyl)-6-phenylquinolin-4-amine;
3-(4-(4-(6-phenylquinolin-4-ylamino)phenyl)piperazin-1-yl)propanenitrile;
2-(4-(4-(6-phenylquinolin-4-ylamino)phenyl)piperazin-1-yl)acetic acid;
6-(4-methoxyphenyl)-N-(4-(piperazin-1-yl)phenyl)quinolin-4-amine;
N-(4-(4-ethylpiperazin-1-yl)phenyl)-6-(4-methoxyphenyl)quinolin-4-amine;
6-(4-methoxyphenyl)-N-(4-(4-propylpiperazin-1-yl)phenyl)quinolin-4-amine;
N-(4-(4-butylpiperazin-1-yl)phenyl)-6-(4-methoxyphenyl)quinolin-4-amine;
N-(4-(4-isopropylpiperazin-1-yl)phenyl)-6-(4-methoxyphenyl)quinolin-4-amine;
2-(4-(4-(6-(4-methoxyphenyl)quinolin-4-ylamino)phenyl)piperazin-1-yl)ethanol;
3-(4-(4-(6-(4-methoxyphenyl)quinolin-4-ylamino)phenyl)piperazin-1-yl)propan-1-ol;
N-(4-(4-(2-(dimethylamino)ethyl)piperazin-1-yl)phenyl)-6-(4-methoxyphenyl)quinolin-4-amine;
3-(4-(4-(6-(4-methoxyphenyl)quinolin-4-ylamino)phenyl)piperazin-1-yl)propanenitrile;
2-(4-(4-(6-(4-methoxyphenyl)quinolin-4-ylamino)phenyl)piperazin-1-yl)-N,N-dimethylacetamide;
2-(4-(4-(6-(4-methoxyphenyl)quinolin-4-ylamino)phenyl)piperazin-1-yl)acetic acid;
4-(4-(4-(piperazin-1-yl)phenylamino)quinolin-6-yl)benzonitrile;
4-(4-(4-(4-ethylpiperazin-1-yl)phenylamino)quinolin-6-yl)benzonitrile;
4-(4-(4-(4-propylpiperazin-1-yl)phenylamino)quinolin-6-yl)benzonitrile;
4-(4-(4-(4-butylpiperazin-1-yl)phenylamino)quinolin-6-yl)benzonitrile;
4-(4-(4-(4-sec-butylpiperazin-1-yl)phenylamino)quinolin-6-yl)benzonitrile;
4-(4-(4-(4-(pentan-3-yl)piperazin-1-yl)phenylamino)quinolin-6-yl)benzonitrile;
4-(4-(4-(4-allylpiperazin-1-yl)phenylamino)quinolin-6-yl)benzonitrile;

4-(4-(4-(4-cyclohexylpiperazin-1-yl)phenylamino)quinolin-6-yl)benzonitrile;
4-(4-(4-(4-(2-hydroxyethyl)piperazin-1-yl)phenylamino)quinolin-6-yl)benzonitrile;
4-(4-(4-(4-(3-hydroxypropyl)piperazin-1-yl)phenylamino)quinolin-6-yl)benzonitrile;
4-(4-(4-(4-(2-(dimethylamino)ethyl)piperazin-1-yl)phenylamino)quinolin-6-yl)benzonitrile;
4-(4-(4-(4-(2-cyanoethyl)piperazin-1-yl)phenylamino)quinolin-6-yl)benzonitrile;
2-(4-(4-(6-(4-cyanophenyl)quinolin-4-ylamino)phenyl)piperazin-1-yl)acetic acid;
N-(4-(4-sec-butylpiperazin-1-yl)phenyl)-6-phenylquinolin-4-amine;
N-(4-(4-cyclopentylpiperazin-1-yl)phenyl)-6-phenylquinolin-4-amine;
N-(4-(4-cyclohexylpiperazin-1-yl)phenyl)-6-phenylquinolin-4-amine;
N-(4-(4-sec-butylpiperazin-1-yl)phenyl)-6-(4-methoxyphenyl)quinolin-4-amine;
N-(4-(4-cyclopentylpiperazin-1-yl)phenyl)-6-(4-methoxyphenyl)quinolin-4-amine;
N-(4-(4-cyclohexylpiperazin-1-yl)phenyl)-6-(4-methoxyphenyl)quinolin-4-amine;
4-(4-(4-(4-isopropylpiperazin-1-yl)phenylamino)quinolin-6-yl)benzonitrile;
4-(4-(4-(4-cyclopentylpiperazin-1-yl)phenylamino)quinolin-6-yl)benzonitrile;
4-(4-(4-(4-(2-methoxyethyl)piperazin-1-yl)phenylamino)quinolin-6-yl)benzonitrile;
2-(4-(4-(6-(4-cyanophenyl)quinolin-4-ylamino)phenyl)piperazin-1-yl)-N,N-dimethylacetamide;
N-methyl-N-(4-(4-methylpiperazin-1-yl)phenyl)-6-phenylquinolin-4-amine;
N-(4-(4-methylpiperazin-1-yl)phenyl)-6-phenyl-N-propylquinolin-4-amine;
6-(4-methoxyphenyl)-N-methyl-N-(4-(4-methylpiperazin-1-yl)phenyl)quinolin-4-amine;
6-(4-methoxyphenyl)-N-(4-(4-methylpiperazin-1-yl)phenyl)-N-propylquinolin-4-amine;
7-(4-chlorophenyl)-N-(4-(4-methylpiperazin-1-yl)phenyl)isoquinolin-1-amine;
7-(3-chlorophenyl)-N-(4-(4-methylpiperazin-1-yl)phenyl)isoquinolin-1-amine;
7-(2-methoxyphenyl)-N-(4-(4-methylpiperazin-1-yl)phenyl)isoquinolin-1-amine;
7-(3-methoxyphenyl)-N-(4-(4-methylpiperazin-1-yl)phenyl)isoquinolin-1-amine;
7-(4-methoxyphenyl)-N-(4-(4-methylpiperazin-1-yl)phenyl)isoquinolin-1-amine;
4-(1-(4-(4-propylpiperazin-1-yl)phenylamino)isoquinolin-7-yl)benzonitrile;
4-(1-(4-(4-(2-cyanoethyl)piperazin-1-yl)phenylamino)isoquinolin-7-yl)benzonitrile;
4-(1-(4-(4-(3-hydroxypropyl)piperazin-1-yl)phenylamino)isoquinolin-7-yl)benzonitrile;
4-(1-(4-(4-methylpiperazin-1-yl)phenylamino)isoquinolin-7-yl)benzonitrile;
4-(4-(4-(4-methylpiperidin-1-yl)phenylamino)quinolin-6-yl)benzonitrile;
4-(4-(4-(4-(dimethylamino)piperidin-1-yl)phenylamino)quinolin-6-yl)benzonitrile;
4-(4-(4-(2-((dimethylamino)methyl)pyrrolidin-1-yl)phenylamino)quinolin-6-yl)benzonitrile;
4-(4-(4-(3-((dimethylamino)methyl)piperidin-1-yl)phenylamino)quinolin-6-yl)benzonitrile;
4-(4-(4-(4-((dimethylamino)methyl)piperidin-1-yl)phenylamino)quinolin-6-yl)benzonitrile;
4-(4-(4-(3-(dimethylamino)piperidin-1-yl)phenylamino)quinolin-6-yl)benzonitrile;
4-(4-(4-(3-(dimethylamino)pyrrolidin-1-yl)phenylamino)quinolin-6-yl)benzonitrile;
4-(4-(4-(3-(methylamino)pyrrolidin-1-yl)phenylamino)quinolin-6-yl)benzonitrile;
6-(3-chlorophenyl)-N-(4-(3-(dimethylamino)pyrrolidin-1-yl)phenyl)quinolin-4-amine;
6-(4-chlorophenyl)-N-(4-(3-(dimethylamino)pyrrolidin-1-yl)phenyl)quinolin-4-amine;
N-(4-(3-(dimethylamino)pyrrolidin-1-yl)phenyl)-6-m-tolylquinolin-4-amine;
N-(4-(3-(dimethylamino)pyrrolidin-1-yl)phenyl)-6-p-tolylquinolin-4-amine;
N-(4-(3-(dimethylamino)pyrrolidin-1-yl)phenyl)-6-(3-methoxyphenyl)quinolin-4-amine;
N-(4-(3-(dimethylamino)pyrrolidin-1-yl)phenyl)-6-(4-methoxyphenyl)quinolin-4-amine;
N-(4-(3-(dimethylamino)pyrrolidin-1-yl)phenyl)-6-(4-fluoro-3-methylphenyl)quinolin-4-amine;
6-(3-(benzyloxy)phenyl)-N-(4-(3-(dimethylamino)pyrrolidin-1-yl)phenyl)quinolin-4-amine;
N-(4-(3-(dimethylamino)pyrrolidin-1-yl)phenyl)-6-(4-vinylphenyl)quinolin-4-amine;
6-(3,4-dichlorophenyl)-N-(4-(3-(dimethylamino)pyrrolidin-1-yl)phenyl)quinolin-4-amine;
N-(4-(3-(dimethylamino)pyrrolidin-1-yl)phenyl)-6-(3,4-dimethylphenyl)quinolin-4-amine;
N-(4-(3-(dimethylamino)pyrrolidin-1-yl)phenyl)-6-(naphthalen-2-yl)quinolin-4-amine;
N-(4-(3-(dimethylamino)pyrrolidin-1-yl)phenyl)-6-(4-isopropylphenyl)quinolin-4-amine;
6-(benzo[b]thiophen-3-yl)-N-(4-(3-(dimethylamino)pyrrolidin-1-yl)phenyl)quinolin-4-amine;
N-(4-(3-(dimethylamino)pyrrolidin-1-yl)phenyl)-6-(5-methylpyridin-2-yl)quinolin-4-amine;
N-(4-(3-(dimethylamino)pyrrolidin-1-yl)phenyl)-6-(1H-indol-5-yl)quinolin-4-amine;
6-(4-(4-(3-(dimethylamino)pyrrolidin-1-yl)phenylamino)quinolin-6-yl)benzo[d]thiazol-2(3H)-one;
5-(4-(4-(3-(dimethylamino)pyrrolidin-1-yl)phenylamino)quinolin-6-yl)-2,3-dihydroinden-1-one;
5-(4-(4-(3-(dimethylamino)pyrrolidin-1-yl)phenylamino)quinolin-6-yl)nicotinic acid;
6-(6-chloropyridin-3-yl)-N-(4-(3-(dimethylamino)pyrrolidin-1-yl)phenyl)quinolin-4-amine;
N-(4-(3-(dimethylamino)pyrrolidin-1-yl)phenyl)-6-(1H-indol-4-yl)quinolin-4-amine;
6-(6-chloro-5-methylpyridin-3-yl)-N-(4-(3-(dimethylamino)pyrrolidin-1-yl)phenyl)quinolin-4-amine;
N-(4-(3-(dimethylamino)pyrrolidin-1-yl)phenyl)-6-(thiazol-2-yl)quinolin-4-amine;
1-(5-(4-(4-(3-(dimethylamino)pyrrolidin-1-yl)phenylamino)quinolin-6-yl)indolin-1-yl)ethanone;
4-(4-(4-(3-(dimethylamino)pyrrolidin-1-yl)phenylamino)quinolin-6-yl)-2-methylbenzonitrile;
6-(4-(difluoromethoxy)phenyl)-N-(4-(3-(dimethylamino)pyrrolidin-1-yl)phenyl)quinolin-4-amine;
6-(4-(diethylamino)phenyl)-N-(4-(3-(dimethylamino)pyrrolidin-1-yl)phenyl)quinolin-4-amine;
N-(4-(3-(dimethylamino)pyrrolidin-1-yl)phenyl)-6-(1H-indol-6-yl)quinolin-4-amine;
4-(4-(4-(3-(dimethylamino)pyrrolidin-1-yl)phenylamino)quinolin-6-yl)-2-fluorobenzonitrile;

6-(4-chloro-3-methoxyphenyl)-N-(4-(3-(dimethylamino)
  pyrrolidin-1-yl)phenyl)quinolin-4-amine;
6-(4-chloro-3-fluorophenyl)-N-(4-(3-(dimethylamino)pyr-
  rolidin-1-yl)phenyl)quinolin-4-amine;
6-(benzo[d][1,3]dioxol-5-yl)-N-(4-(3-(dimethylamino)pyr-
  rolidin-1-yl)phenyl)quinolin-4-amine;
N-(4-(3-(dimethylamino)pyrrolidin-1-yl)phenyl)-6-(3-
  fluoro-4-methylphenyl)quinolin-4-amine;
6-(3-chloro-4-methylphenyl)-N-(4-(3-(dimethylamino)pyr-
  rolidin-1-yl)phenyl)quinolin-4-amine;
N-(4-(3-(dimethylamino)pyrrolidin-1-yl)phenyl)-6-(3-
  fluoro-4-methoxyphenyl)quinolin-4-amine;
6-(4-chloro-3-methylphenyl)-N-(4-(3-(dimethylamino)pyr-
  rolidin-1-yl)phenyl)quinolin-4-amine;
6-(4-chlorophenyl)-N-(4-(3-(diethylamino)pyrrolidin-1-yl)
  phenyl)quinolin-4-amine;
4-(4-(4-(3-(diethylamino)pyrrolidin-1-yl)phenylamino)
  quinolin-6-yl)benzonitrile;
N-(4-(3-(diethylamino)pyrrolidin-1-yl)phenyl)-6-(naphtha-
  len-2-yl)quinolin-4-amine;
(R)-6-(4-chlorophenyl)-N-(4-(3-(dimethylamino)pyrroli-
  din-1-yl)phenyl)quinolin-4-amine;
(R)-4-(4-(4-(3-(dimethylamino)pyrrolidin-1-yl)pheny-
  lamino)quinolin-6-yl)benzonitrile;
(R)-N-(4-(3-(dimethylamino)pyrrolidin-1-yl)phenyl)-6-
  (naphthalen-2-yl)quinolin-4-amine;
(S)-6-(4-chlorophenyl)-N-(4-(3-(dimethylamino)pyrrolidin-
  1-yl)phenyl)quinolin-4-amine;
(S)-4-(4-(4-(3-(dimethylamino)pyrrolidin-1-yl)pheny-
  lamino)quinolin-6-yl)benzonitrile;
(S)-N-(4-(3-(dimethylamino)pyrrolidin-1-yl)phenyl)-6-
  (naphthalen-2-yl)quinolin-4-amine;
4-(4-(4-(3-(benzyl(methyl)amino)pyrrolidin-1-yl)pheny-
  lamino)quinolin-6-yl)benzonitrile;
4-(4-(4-(3-(methyl(3,3,3-trifluoropropyl)amino)pyrrolidin-
  1-yl)phenylamino)quinolin-6-yl)benzonitrile;
6-(4-chlorophenyl)-N-(6-(4-methylpiperazin-1-yl)pyridin-
  3-yl)quinolin-4-amine;
4-(4-(6-(4-methylpiperazin-1-yl)pyridazin-3-ylamino)
  quinolin-6-yl)benzonitrile;
4-(4-(6-(4-methylpiperazin-1-yl)pyridin-3-ylamino)quino-
  lin-6-yl)benzonitrile;
4-(4-(4-(4-methylpiperazin-1-yl)phenoxy)quinolin-6-yl)
  benzonitrile;
6-(4-chlorophenyl)-4-(4-(4-methylpiperazin-1-yl)phenoxy)
  quinoline;
4-(4-(4-(1-methylpiperidin-4-yl)phenylamino)quinolin-6-
  yl)benzonitrile;
4-(4-(4-(piperidin-4-yl)phenylamino)quinolin-6-yl)ben-
  zonitrile;
N1-(3,6'-biquinolin-4'-yl)-N-4-methyl-N-4-(1-methylpyrro-
  lidin-3-yl)benzene-1,4-diamine;
4-(4-(4-(methyl(1-methylpyrrolidin-3-yl)amino)pheny-
  lamino)quinolin-6-yl)benzonitrile; and
N1-methyl-N-4-(6-(5-methylpyridin-2-yl)quinolin-4-yl)-N-
  1-(1-methylpyrrolidin-3-yl)benzene-1,4-diamine.

Certain of those compounds were tested for protein kinase inhibitory activity according to the biological assays and definitions of protein kinase inhibitory activity as described herein.

Chemical entities described herein can be prepared by methods well known in the art. Chemical entities described herein can be prepared from readily available starting materials using the following general methods and procedures. It will be appreciated that where typical or preferred process conditions, such as, reaction temperatures, times, mole ratios of reactants, solvents, pressures, are given, other process conditions can also be used unless otherwise stated. Reaction conditions may vary with the reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis,* 3$^{rd}$ Edition, John Wiley & Sons, 1999, and references cited therein.

Furthermore, chemical entities described herein can contain one or more chiral centers. Accordingly, if desired, such chemical entities can be prepared or isolated as pure stereoisomers, i.e., as individual enantiomers or diastereomers, or as stereoisomer-enriched mixtures. All such stereoisomers, and enriched mixtures thereof, are included within the scope of the present disclosure, unless otherwise indicated. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

General synthetic schemes and specific reaction protocols used to prepare compounds of the present disclosure are presented in the reaction schemes and Examples provided herein.

A compound of Formula 1 can be prepared as illustrated in Schemes 1 through 3 below. The 6-bromo-4-hydroxyquinoline or 7-bromo-1-hydroxyisoquinoline can be transformed into the halide IV (e.g. into the Cl via POCl$_3$) (Scheme 1). In addition, the chloro(iso)quinolines can be treated with an excess of iodide salt (e.g. NaI) to provide the iodo(iso)quinolines. Synthesis of I can occur by initial arylation of IV (where X$^1$=Cl) to provide V, followed by reaction of the appropriate amine/alcohol VII; or, initial reaction of IV (X$^1$=halo) with amine/alcohol VII to provide VI, followed by arylation. Alternatively, arylation can initially provide V', which, following conversion to the corresponding halide, can be coupled with amine/alcohol VII to provide I. Arylation conditions include, but are not limited to, reaction of the bromide with the appropriate arylboronic acid or ester mediated by a metal catalyst. Numerous methods for aryl cross-coupling are known by those skilled in the art (*Metal-Catalyzed Cross-coupling Reactions*, VCH, Weinheim, 1998, 49-97; *J. Organometallic Chem.* 1999, 576, 147-168; Chem. Rev. 1995, 95, 2457; and references cited therein). Coupling of amine/alcohol VII with IV or V can be accomplished in a solvent or neat, at a temperature preferably between 20° C. and 200° C., and optionally with a base such as sodium carbonate or sodium hydride; in the case of utilizing alcohol VII, use of a strong base is preferred. The coupling may also be aided by microwave irradiation.

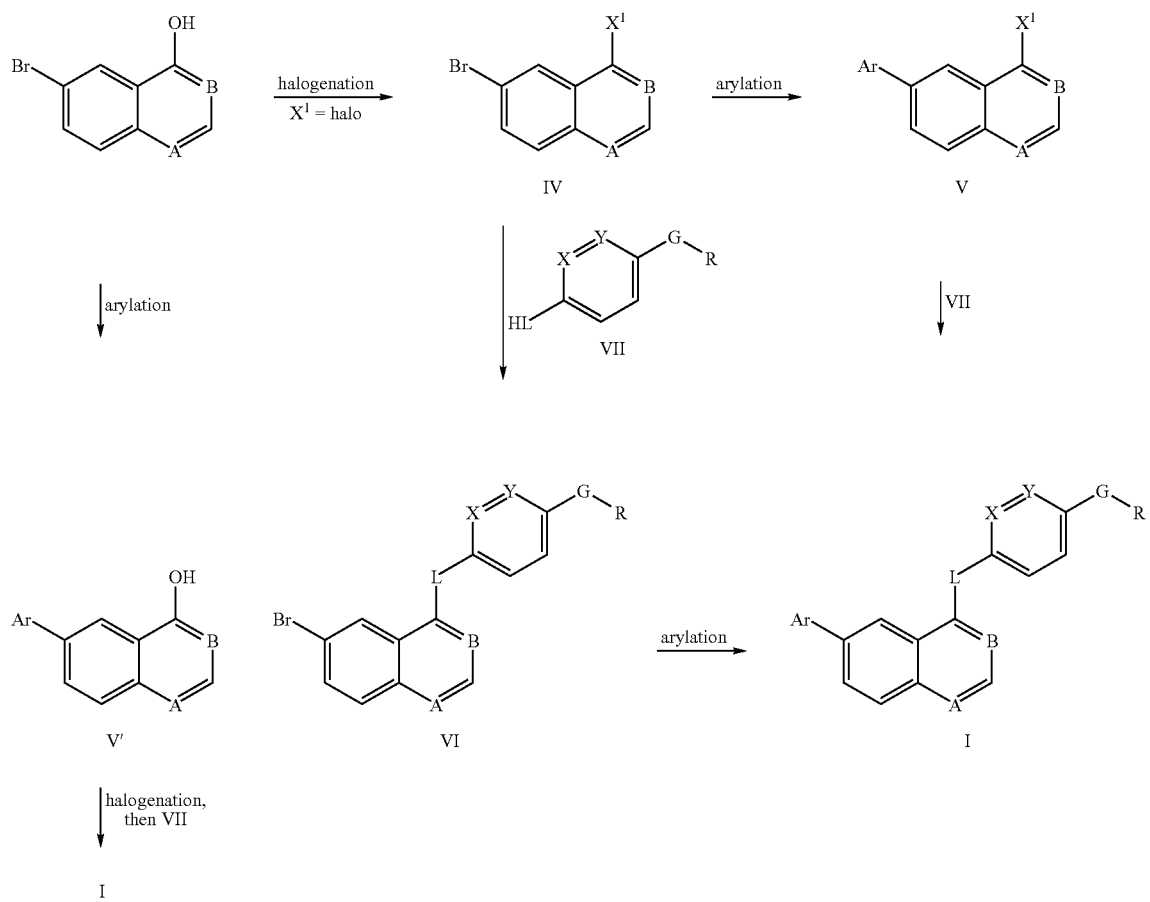

Amines of formula VII can be prepared as illustrated in Scheme 2. Nucleophilic displacement of 4-halonitrobenzene with the appropriately functionalized amine Q-H can provide the nitrophenyl intermediate VIII. Amines Q-H are commercially available or can be prepared via literature methods known by those skilled in the art. Alkylation of 3-phenylpyrrolidine or 4-phenylpiperidine can provide IX, which upon nitration, and separation of isomers if necessary, can provide nitrophenyl intermediate X. Reduction of the appropriate nitrophenyl derivative can provide the primary amine VIIa, which can also be alkylated to form the secondary amine VIIb. Amine alkylations illustrated in Scheme 2 can be accomplished, for example, by reaction of the amine with an alkyl halide or by reductive amination with the appropriate aldehyde under reducing conditions.

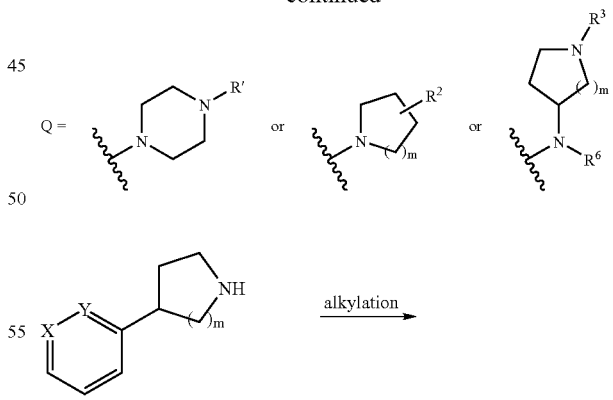

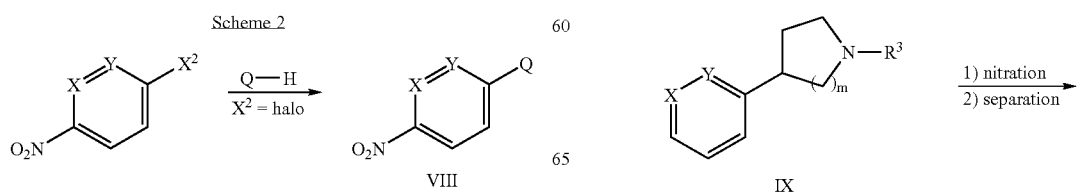

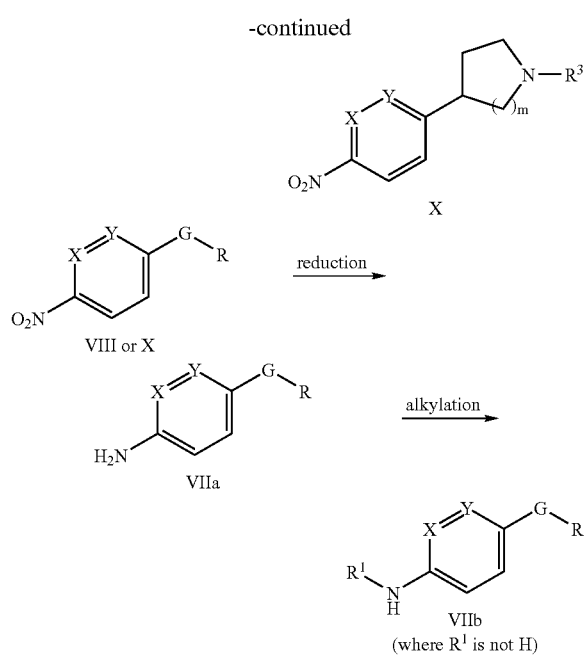

Alcohols of formula VII, where not commercially available, can be prepared as illustrated in Scheme 3. Reaction of an aryl bromide with the appropriate amine Q-H can be accomplished in the presence of a metal catalyst, such as palladium or copper (or their salts) to provide XI. Where the aryl bromide is substituted with an OMe group, demethylation can provide the phenol VIIc. In addition, certain compounds can be prepared from intermediate X via reduction of the nitro group to an amine, formation of the diazonium salt from the resulting amine, and hydrolysis of the diazonium salt to give phenols VIId.

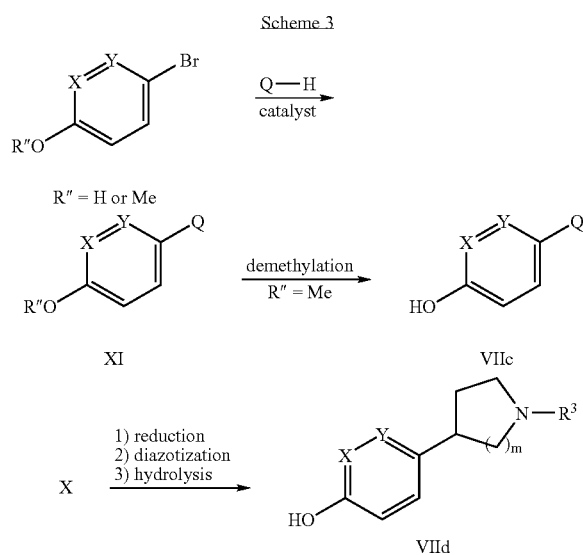

In accordance with certain embodiments, chemical entities of the present disclosure exhibit ATP-utilizing enzyme inhibitory activity. Thus, one use of the chemical entities of the present present disclosure includes the administration of at least one chemical entity of the present disclosure to a subject, such as a human. This administration serves to arrest, ameliorate, reduce the risk of acquiring, reduce the development of or at least one of the clinical symptoms of, or reduce the risk of developing or at least one of the clinical symptoms of diseases or conditions regulated by ATP-utilizing enzymes, such as, protein kinases.

For example, unregulated or inappropriately high protein kinase activity has been implicated in many diseases resulting from abnormal cellular function. Unregulated or inappropriately high protein kinase activity can arise either directly or indirectly, for example, by failure of the proper control mechanisms of a protein kinase, related, for example, to mutation, over-expression or inappropriate activation of the enzyme; or by over- or under-production of cytokines or growth factors also participating in the transduction of signal upstream or downstream of the protein kinase. In all of these instances, selective inhibition of the action of a protein kinase can be expected to have a beneficial effect.

According to certain embodiments, the present disclosure relates to methods of treating a disease regulated by at least one ATP-utilizing enzyme in a subject. ATP-utilizing enzyme regulated diseases include, for example, those where the ATP-utilizing enzyme participates in the signaling, mediation, modulation, control or otherwise involved in the biochemical processes affecting the manifestation of a disease. In certain embodiments, the methods are useful in treating diseases regulated by protein kinase enzymes. Protein kinase regulated diseases include, for example, the following general disease classes: cancer, autoimmunological, metabolic, inflammatory, infection, diseases of the central nervous system, degenerative neural disease, allergy/asthma, angiogenesis, neovascularization, vasucolgenesis, cardiovascular, and the like. Without being limited by theory, specific examples of diseases that are known or believed to be regulated by protein kinase enzymes, include, transplant rejection, osteoarthritis, rheumatoid arthritis, multiple sclerosis, diabetes, diabetic retinopathy, asthma, inflammatory bowel disease such as Crohn's disease, and ulcerative colitis, renal disease cachexia, septic shock, lupus, diabetes mellitus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, leukemia including, but not limited to, acute myeloid leukemia, chronic myeloid leukemia, and acute lymphoblastic leukemia, cancer including but not limited to, breast cancer, lung cancer, colorectal cancer, ovary cancer, prostate cancer, renal cancer, squamous cell cancer, glioblastoma, melanoma, pancreatic cancer, and Kaposi's sarcoma, ocular disease, corneal disease, glaucoma, bacterial infections, viral infections, fungal infections, heart disease, stroke, and obesity.

Chemical entities of the present disclosure can be used in the treatment of diseases in which inappropriate protein kinase activity plays a role, including, for example, Alzheimer's disease, stroke, diabetes, obesity, inflammation, and cancer. In particular, cpompounds of the present disclosure can be used in the treatment of inflammatory diseases such as, for example, Crohn's disease, rheumatoid arthritis, psoriasis, and inflammatory bowel disease.

Certain embodiments of the present disclosure are directed to methods of treating disease in a subject comprising the step of administering to a subject, in need of such treatment, a therapeutically effective dosage of at least one compound of the present disclosure. In some embodiments, a disease can be regulated by at least one ATP-utilizing enzyme such as a protein kinase. Certain diseases can be regulated by one or more ATP-utilizing enzymes. In such cases, treatment of the disease or disorder can include administering a therapeutically effective amount of at least one compound of the present disclosure that inhibits the activity of one or more ATP-utilizing enzymes, or more than one compound of the present disclosure, wherein each compound inhibits at least one different ATP-utilizing enzyme.

Other embodiments of the present disclosure are related to methods of inhibiting at least one ATP-utilizing enzyme, including for example, a protein kinase. In certain embodiments, the ATP-utilizing enzyme can be inhibited by the method of administering to a subject, at least one chemical entity described herein, or a composition comprising at least chemical entity describe herein.

In certain embodiments, the present disclosure relates to methods of inhibiting ATP-utilizing enzyme activity by contacting at least one ATP-utilizing enzyme with at least one chemical entity of the present disclosure. ATP-utilizing enzymes include phosphotransferase enzymes that catalyze the phosphorylation of a biological molecule by transferring a phosphate group from an ATP substrate. ATP-utilizing enzymes include for example, synthetases, ligases, and kinases. Certain methods of the present disclosure are useful in inhibiting protein kinase enzymes, including, for example, the following protein kinase enzymes ABL1, AKT1, AKT2, AKT3, AURORA-A, BMX, c-TAK1, CDK1, CDK1/cyclinB, CDK2/cyclinA, CDK2/cyclinE, CDK5, CHEK1, CHEK2, CK2, CSK, DAPK1, DYRK2, FLT-3, FYN, GSK3-α, GSK3-β, HCK, INSR, KIT, LCK, LYNA, MAPKAPK2, MAPKAPK3, MSK1, MSK2, NEK2, p38-α, p38-β, p38-δ, p38-γ, P70S6K1, PAK2, PDGFR-α, PAK1, PKA, PRAK, ROCK2, SGK1, SRC, SYK, PIM-1-kinase, PDK1, and RSK2.

Some methods of the present disclosure can be used to inhibit ATP-utilizing enzymes that are present in a living organism, such as a mammal; contained in a biological sample such as a cell, cell culture, or extract thereof, biopsied material obtained from a mammal or extracts thereof, and blood, saliva, feces, semen, tears or other body fluids or extracts thereof; contained within a reagent, or bound to a physical support. In certain embodiments, an ATP-utilizing enzyme can regulate a disease or disorder and in other embodiments, the ATP-utilizing enzyme may not regulate a disease or disorder.

According to the methods of the present disclosure, at least one ATP-utilizing enzyme can be inhibited by contact with at least one chemical entity of the present disclosure. In vivo ATP-utilizing enzymes can be inhibited by administration through routes and using compositions comprising at least one chemical entity of the present disclosure previously described. For in vitro systems, contacting an ATP-utilizing enzyme with at least one chemical entity of the present disclosure can include, for example, combining liquid reagents or combining a reagent and an ATP-utilizing enzyme and/or chemical entity of the present disclosure attached to a solid support. The ATP-utilizing enzyme and chemical entity of the present disclosure can be contacted in any appropriate device such as an affinity chromatography column, a microarray, a microfluidic device, assay plate, or other appropriate chemical or biotechnology apparatus used to perform biochemical analysis, assay, screening, and the like.

In certain embodiments, pharmaceutical compositions of the present disclosure may be administered orally, parenterally, by inhalation spray, topically, rectally, nasally, buccally, vaginally, via an implanted reservoir, or by any other appropriate route. Pharmaceutical compositions of the present disclosure can contain any conventional non-toxic pharmaceutically acceptable, excipients carriers, adjuvants and/or vehicles. In some embodiments, the pH of the formulation can be adjusted with pharmaceutically acceptable acids, bases or buffers to enhance the stability of the formulated compound or the delivery form. The term parenteral as used herein includes subcutaneous, intracutaneous, intravenous, intramuscular, intra-articular, intra-arterial, interasynovial, intrasternal, interathecal, intralesional, and intracranial injection or infusion techniques.

In certain embodiments, chemical entities disclosed herein can be delivered orally. Suitable dosage ranges for oral administration can depend on the potency of the chemical entity, but generally can range from 0.1 mg to 20 mg of a chemical entity per kilogram of body weight. Appropriate dosages can be in the range of 25 to 500 mg/day and the dose of chemical entity administered can be adjusted to provide an equivalent molar quantity of chemical entity in the plasma of a subject. Dosage ranges can be readily determined by methods known to those skilled in the art.

A dosage can be delivered in a composition by a single administration, by multiple applications, by sustained release or by controlled sustained release, or any other appropriate intervals and/or rates of release.

Chemical entities of the present disclosure can be assayed in vitro and in vivo, for the desired therapeutic or prophylactic activity prior to therapeutic use in mammals. For example, in vitro assays can be used to determine whether administration of one chemical entity of the present disclosure or a combination of such chemical entities is effective for inhibiting the activity of certain ATP-utilizing enzymes or treating at least one disease. Chemical entities of the present disclosure can also be demonstrated to be effective and safe using animal model systems. A therapeutically effective dose of a chemical entity of the present disclosure can, in certain embodiments, provide therapeutic benefit without causing substantial toxicity. Toxicity of chemical entities of the present disclosure can be determined using standard pharmaceutical procedures and can be readily ascertained by the skilled artisan. The dose ratio between toxic and therapeutic effect is the therapeutic index. Chemical entities of the present disclosure can exhibit high therapeutic indices in treating diseases and disorders. The dosage of a chemical entity of the present present disclosure can be within a range of circulating concentrations that include an effective dose with little or no toxicity.

When employed as pharmaceuticals, chemical entities of the present disclosure can be administered in the form of pharmaceutical compositions. Such compositions can be prepared in a manner well known in the pharmaceutical art and can comprise at least one chemical entity of the present disclosure.

Pharmaceutical compositions of the present disclosure can comprise a therapeutically effective amount of at least one chemical entity of the present disclosure, and at least one pharmaceutically acceptable excipient, such as, for example, diluents, carriers, or adjuvants. Pharmaceutical compositions of the present disclosure can additionally comprise at least one chemical entity that enhances the therapeutic efficacy of one or more chemical entities of the present disclosure. For example, such chemical entities can enhance the therapeutic efficacy of chemical entities of the present disclosure by effectively increasing the plasma concentration of the chemical entities. Without being limited by theory, certain chemical entities can decrease the degradation of the chemical entities of the present disclosure prior to administration or during transport to the plasma, or within the plasma. Certain chemical entites can increase the plasma concentration by increasing the absorption of chemical entities in the gastrointestinal tract. Pharmaceutical compositions of the present disclosure can also include additional therapeutic agents that are normally administered to treat a disease or disorder.

In some embodiments, chemical entities and compositions of the present disclosure can be administered by oral routes. The compositions can be prepared in a manner well known in the pharmaceutical art and can comprise at least one chemical entity of the present disclosure. In some embodiments, compositions of the present disclosure contain a therapeutically effective amount of one or more thiatriazole-based chemical entities of the present disclosure, which can be in purified form, together with a therapeutically effective amount of at least one additional therapeutic agent, and a suitable amount of at least one pharmaceutically acceptable excipient, so as to provide the form for proper administration to a subject Some embodiments of the present disclosure are directed to compositions that contain, as the active ingredient, of at least one chemical entity of the present disclosure associated with pharmaceutically acceptable excipients. In making certain compositions of the present disclosure, the active ingredient can be mixed with an excipient, diluted by an excipient, or enclosed within such a carrier that can be in the form of a capsule, sachet, paper or other container. When the excipient serves as a diluent, the excipient can be a solid, semi-solid, or liquid material, which acts as a vehicle, carrier or medium for the active ingredient. Thus, for example, the compositions can be in the form of tablets, pills, powders, lozenges, sachets, cachets, elixirs, suspensions, emulsions, solutions, and syrups containing, for example, from 1% to 90% by weight of at least one chemical entity of the present disclosure using, for example, soft and hard gelatin capsules.

In preparing a composition, it can be necessary to mill the active chemical entity to provide the appropriate particle size prior to combining with other ingredients. If the active chemical entity is insoluble, the active component ordinarily can be milled to a particle size of less than 200 mesh. If the active chemical entity is water soluble, the particle size can be adjusted by milling to provide a uniform distribution in the formulation, e.g. 40 mesh.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. Some compositions can additionally include, lubricating agents such as talc, magnesium stearate, and mineral oil, wetting agents, emulsifying and suspending agents, preserving agents such as methyl- and propylhydroxy-benzoates, sweetening agents, and flavoring agents. Compositions of the present disclosure can be formulated so as to provide quick, sustained or delayed release of the active ingredient after administration to the subject by employing procedures known in the art.

Some compositions of the present disclosure can be formulated in unit dosage form, each dosage containing, for example, 0.1 mg to 2 g of the active ingredient. As used herein, "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, diluent, carrier and/or adjuvant. In certain embodiments, compositions of the present disclosure can be formulated in multiple dosage forms. The amount of the chemical entities of the present disclosure that can be combined with other materials and therapeutic agents to produce compositions of the present disclosure in a single dosage form will vary depending upon the subject and the particular mode of administration.

In the treatment of disease, chemical entities of the present disclosure can be administered in a therapeutically effective amount. It will be understood, however, that the amount of the chemical entity administered will be determined by a physician, in the light of the relevant circumstances, including the condition to be treated, the chosen route of administration, the actual chemical entity administered, the age, weight, and response of the individual subject, the severity of the subject's symptoms, and the like.

For preparing solid compositions such as tablets, the principal active ingredient can be mixed with a pharmaceutical excipient to form a solid preformulation composition containing a homogeneous mixture of a chemical entity of the present present disclosure. When referring to these preformulation compositions as homogeneous, it is meant that the active ingredient is dispersed evenly throughout the composition so that the composition may be readily subdivided into equally effective unit dosage forms such as tablets, pills and capsules. The solid preformulation can then subdivided into unit dosage forms of the type described above containing from, for example, 0.1 mg to 2 g of the therapeutically effective chemical entity of the present present disclosure.

The tablets or pills comprising certain compositions of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials include a number of polymeric acids and mixtures of polymeric acids with such materials as shellac, cetyl alcohol, and cellulose acetate.

The liquid forms in which the compositions of the present disclosure may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

As used herein, a "pharmaceutically acceptable derivative or prodrug" refers to any pharmaceutically acceptable salt, ester, salt of an ester or other derivative of a compound of Formula 1 that, upon administration to a recipient, is capable of providing, either directly or indirectly, a compound of the present disclosure or an inhibitory active metabolite or residue thereof. Examples of such derivatives or prodrugs include those that increase the bioavailability of the chemical entities of the present disclosure when such compounds are administered to a mammal, e.g., by allowing an orally administered compound to be more readily absorbed into the blood, or which enhance delivery of the parent compound to a biological compartment, e.g., the brain or lymphatic system, relative to the parent species.

In certain embodiments, acceptable formulation materials can be nontoxic to recipients at the dosages and concentrations employed.

In certain embodiments, a pharmaceutical composition of the present disclosure can contain formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids such as glycine, glutamine, asparagine, arginine or lysine; antimicrobials; antioxidants such as ascorbic acid, sodium sulfite, or sodium hydrogen-sulfite; buffers such as borate, bicarbonate, Tris-HCl, citrates, phosphates or other organic acids; bulking agents such as mannitol or glycine; chelating agents such as ethylenediamine tetraacetic acid (EDTA); complexing agents such as caffeine, polyvinylpyrrolidone, beta-cyclodextrin or hydroxypropyl-beta-cyclodextrin; fillers; monosaccharides; disaccharides; and other carbohydrates such as glucose, mannose, or dextrins; proteins such as serum albumin, gelatin or immunoglobulins; coloring, flavoring and diluting agents; emulsifying agents; hydrophilic polymers such as polyvinylpyrrolidone; low molecular weight polypeptides; salt-forming counterions such as sodium; preservatives such as benzalkonium chloride, benzoic acid, salicylic acid, thimerosal, phenethyl alcohol, methylparaben, propylparaben, chlorhexidine, sorbic acid or hydrogen peroxide; solvents such as glycerin, propylene glycol or polyethylene glycol; sugar alcohols such as mannitol or sorbitol; suspending agents; surfactants or wetting agents such as pluronics, PEG, sorbitan esters, polysorbates such as polysorbate 20, polysorbate 80, triton, tromethamine, lecithin, cholesterol, tyloxapal; stability enhancing agents such as sucrose or sorbitol; tonicity enhancing agents such as alkali metal halides, such as sodium or potassium chloride, mannitol, sorbitol; delivery vehicles; diluents; excipients and/or pharmaceutical adjuvants. (Remington's Pharmaceutical Sciences, 18$^{th}$ Edition, A. R. Gennaro, ed., Mack Publishing Company (1990)).

In certain embodiments, the optimal pharmaceutical composition can be determined by one skilled in the art depending upon, for example the intended route of administration, delivery format, and desired dosage. See, for example, Remington's Pharmaceutical Sciences, supra. In certain embodiments, such compositions may influence the physical state, stability, rate of in vivo release, and rate of in vivo clearance of the antibodies of the present disclosure.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of pH 7 to 8.5, or acetate buffer of pH 4 to 5.5, which can further comprise sorbitol or a suitable substitute thereof. In certain embodiments, buffers are used to maintain the composition at physiological pH or at a slightly lower pH, typically within a pH range of from 5 to 8.

In certain embodiments, the pharmaceutical compositions of the present disclosure can be selected for parenteral delivery. In other embodiments, the compositions can be selected for inhalation or for delivery through the digestive tract, such as orally. The preparation of such pharmaceutically acceptable compositions is within the skill of the art.

In certain embodiments, the composition components cam be present in concentrations that are acceptable to the site of administration. In certain embodiments, when parenteral administration is contemplated, a therapeutic composition can be in the form of a pyrogen-free, parenterally acceptable aqueous solution comprising at least one chemical entity of the present disclosure, with or without additional therapeutic agents, in a pharmaceutically acceptable vehicle. In other embodiments, a vehicle for parenteral injection can be sterile distilled water in which at least one chemical entity of the present disclosure, with or without at least one additional therapeutic agent, is formulated as a sterile, isotonic solution, properly preserved. In still other embodiments, the pharmaceutical composition can include encapsulation of a at least one chemical entity of the present disclosure with an agent, such as injectable microspheres, bio-erodible particles, polymeric compounds such as polyacetic acid or polyglycolic acid, beads or liposomes, that can provide the controlled or sustained release of the chemical entity of the present disclosure which can then be delivered via a depot injection. In certain embodiments, implantable drug delivery devices can be used to introduce a chemical entity of the present disclosure to the plasma of a subject, within a target organ, or to a specific site within the subject's body.

In certain embodiments, a pharmaceutical composition can be formulated for inhalation. In certain embodiments, a chemical entity of the present disclosure, with or without at least one additional therapeutic agent, can be formulated as a dry powder for inhalation. In certain embodiments, an inhalation solution comprising a at least one chemical entity of the present disclosure with or without at least one additional therapeutic agent can be formulated with a propellant for aerosol delivery. In other embodiments, solutions can be nebulized. In still other embodiments, solutions, powders or dry films of chemical entities of the present disclosure can be aerosolized or vaporized for pulmonary deliver.

In certain embodiments, it is contemplated that formulations can be administered orally. In certain embodiments, at least one chemical entity of the present disclosure, with or without at least one additional therapeutic agent that can be administered orally, can be formulated with or without carriers customarily used in the compounding of solid dosage forms such as tablets and capsules. In other embodiments, a capsule may be designed to release the active portion of the formulation in the region of the gastrointestinal tract where bioavailability can be maximized and pre-systemic degradation minimized. In still other embodiments, at least one additional agent can be included in the formulation to facilitate absorption of at least one chemical entity of the present disclosure and/or any additional therapeutic agents into the systemic circulation. In certain embodiments, diluents, flavorings, low melting pint waxes, vegetable oils, lubricants, suspending agents, tablet disintegrating agents, and binders can be employed.

In certain embodiments, a pharmaceutical composition of the present disclosure can include an effective quantity of at least one chemical entity of the present disclosure, with or without at least one additional therapeutic agent, in a mixture with non-toxic excipients which are suitable for the manufacture of tablets. In certain embodiments, by dissolving the tablets in sterile water, or other appropriate vehicle, solutions can be prepared in unit-dose form. In certain embodiments, suitable excipients include inert diluents, such as calcium carbonate, sodium carbonate or bicarbonate, lactose, or calcium phosphate; or binding agents, such as starch, gelatin, or acacia; and lubricating agents such as magnesium stearate, stearic acid or talc.

In certain embodiments, the frequency of dosing will take into account the pharmacokinetic parameters of the chemical entity and/or any additional therapeutic agents in the pharmaceutical composition used. In certain embodiments, a clinician can administer the composition until a dosage is reached that achieves the desired effect. The composition can be administered as a single dose, or as two or more doses, which may or may not contain the same amount of the therapeutically active compound time, or as a continuous infusion via an implantation device or catheter. Further refinement of an appropriate dosage can be routinely made by those of ordinary skill in the art. For example, therapeutically effective dosages and dosage regiments can be determined through use of appropriate dose-response data.

In certain embodiments, the route of administration of the pharmaceutical composition can be in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions can be administered by bolus injection or continuously by infusion, or by an implantation device.

In certain embodiments, the composition can be administered locally via implantation of a membrane, sponge or another appropriate material onto which the desired chemical entity of the present disclosure has been absorbed or encapsulated. In certain embodiments, where an implantation device is used, the device can be implanted into any suitable tissue or organ, and delivery of the desired molecule via diffusion, timed-release bolus, or continuous administration.

In certain embodiments, it can be desirable to use a pharmaceutical composition comprising at least one chemical entity of the present disclosure, with or without at least one additional therapeutic agent, in an ex vivo manner. For example, cells, tissues and/or organs that have been removed from a subject are exposed to a pharmaceutical composition comprising at least one chemical entity of the present disclosure, with or without at least one additional therapeutic agent, after which the cells, tissues and/or organs are subsequently implanted back into the subject.

In certain embodiments, at least one chemical entity of the present disclosure and/or any additional therapeutic agents can be delivered by implanting certain cells that have been genetically engineered, using methods known in the art, to express and secrete at least one chemical entity of the present disclosure. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials can be biocompatible, semi-permeable polymeric enclosures or membranes that enable the release of the protein product(s) while preventing the destruction of the cells by the subject's immune system or by other detrimental factors originating from the surrounding tissues.

Pharmaceutical compositions according to the present disclosure can take a form suitable for oral, buccal, parenteral, nasal, topical or rectal administration, or a form suitable for administration by inhalation or insufflation.

The compositions of the present disclosure can, if desired, be presented in a pack or dispenser device that can contain one or more unit dosage forms containing the active ingredient. The pack or dispensing device can be accompanied by instructions for administration.

The quantity of at least one chemical entity of the present disclosure required for the treatment of a particular condition can vary depending on the chemical entity, and the condition of the subject to be treated. In general, daily dosages can range from 100 ng/kg to 100 mg/kg, e.g., 0.01 mg/kg to 40 mg/kg body weight, for oral or buccal administration; from 10 ng/kg to 50 mg/kg body weight, e.g., 0.001 mg/kg to 20 mg/kg body weight, for parenteral administration; and from 0.05 mg to 1,000 mg for nasal administration or administration by inhalation or insufflation.

Certain chemical entities of the present disclosure and/or compositions of the present disclosure can be administered as sustained release systems. In certain embodiments, the chemical entities of the present disclosure can be delivered by oral sustained release administration. In this embodiment, at least one chemical entity of the present disclosure can be administered, for example, twice per day and, once per day.

The methods of the present disclosure can be practiced with a number of different dosage forms, which can be adapted to provide sustained release of at least one chemical entity upon oral administration.

In one embodiment of the present disclosure, the dosage form comprises beads that on dissolution or diffusion release at least one chemical entity of the present disclosure over an extended period of hours, for example, over a period of at least 6 hours, over a period of at least 8 hours or over a period of at least 12 hours. The compound-releasing beads can include a central composition or core comprising at least one chemical entity of the present disclosure and pharmaceutically acceptable vehicles, including an optional lubricant, antioxidant and buffer. The beads can be medical preparations with a diameter of 1 to 2 mm. Individual beads can comprise doses of a compound of the present disclosure, for example, doses of up to 40 mg of the compound. In certain embodiments, the beads can be formed of non-cross-linked materials to enhance discharge of the beads from the gastrointestinal tract. The beads can be coated with a release rate-controlling polymer that gives a timed-release profile.

The timed-release beads can be manufactured into a tablet for therapeutically effective administration of a compound of the present disclosure. The beads can be formed into matrix tablets by the direct compression of a plurality of beads coated with, for example, an acrylic resin, and blended with excipients such as hydroxypropylmethyl cellulose.

In other embodiments, an oral sustained release pump can be used.

In other embodiments, polymeric materials can be used. In other embodiments, polymeric materials appropriate for oral sustained release delivery can be used. Examples of useful polymers include sodium carboxymethylcellulose, hydroxypropylcellulose, hydroxypropylmethylcellulose, hydroxyethylcellulose, and hydroxypropylmethylcellulose. Factors affecting controlled drug release are well known to the skilled artisan.

In other embodiments, enteric-coated preparations can be used for oral sustained release administration. Enteric coating materials include polymers exhibiting a pH-dependent solubility (i.e., pH-controlled release), polymers exhibiting a slow or pH-dependent rate of swelling, dissolution or erosion (i.e., time-controlled release), polymers that can be degraded by enzymes (i.e., enzyme-controlled release), and polymers capable of forming firm layers that can be destroyed by an increase in pressure (i.e., pressure-controlled release).

In still other embodiments, drug-releasing lipid matrices can be used for oral sustained release administration. In one example, chemical entities of the present disclosure can be coated with a thin controlled release layer of a lipid to form solid microparticles, such as glyceryl behenate and/or glyceryl palmitostearate. The lipid-coated particles can optionally be compressed to form a tablet. Another controlled release lipid-based matrix material which can be suitable for sustained-release oral administration comprises polyglycolized glycerides.

In still other embodiments, compound-releasing waxes can be used for oral sustained release administration. Examples of suitable sustained drug-releasing waxes include carnauba wax, candedilla wax, esparto wax, ouricury wax, hydrogenated vegetable oil, bees wax, paraffin, castor wax, ozokerite, and mixtures thereof.

In still other embodiments, osmotic delivery systems can be used for oral sustained release administration.

In other embodiments, a controlled-release system can be placed in proximity to the target of the compound of the present disclosure, thus requiring only a fraction of the systemic dose.

In other embodiments, the dosage form can comprise a compound of the present disclosure coated on a polymer substrate. The polymer can be an erodible, or a nonerodible polymer. The coated substrate can be folded to provide a bilayer polymer drug dosage form. For example, a compound of the present disclosure can be coated onto a polymer such as a polypeptide, collagen, gelatin, polyvinyl alcohol, polyorthoester, polyacetyl, or a polyorthocarbonate, and the coated polymer folded to provide a bilaminated dosage form.

In practice, the bioerodible dosage form can erode at a controlled rate to dispense the compound over a sustained release period. Representative biodegradable polymers include a polymer chosen from biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly (dehydropyrans), and poly(dioxinones).

In other embodiments, the dosage form can comprise a compound of the present disclosure loaded into a polymer that can release the compound by diffusion through a polymer, by flux through pores, or by rupture of a polymer matrix. The drug delivery polymeric dosage form can comprise a concentration of from 10 mg to 2,500 mg of the compound, homogenously contained in or on a polymer. The dosage form can comprise at least one exposed surface at the beginning of dose delivery. The non-exposed surface, when present, can be coated with a pharmaceutically acceptable material impermeable to the passage of the compound of the present disclosure. The dosage form can be manufactured by procedures known in the art. An example of providing a dosage form includes blending a pharmaceutically acceptable carrier such as polyethylene glycol, with a known dose of a compound of the present disclosure at an elevated temperature, such as 37° C., and adding the blend to a Silastic® medical grade elastomer with a cross-linking agent, for example, octanoate, followed by casting in a mold. The step can be repeated for each optional successive layer. The system can be allowed to set for 1 hour, to provide the dosage form. Representative polymers for manufacturing the dosage form include olefin, and vinyl polymers, addition polymers, condensation polymers, carbohydrate polymers, and silicon polymers as represented by polyethylene, polypropylene, polyvinyl acetate, polymethylacrylate, polyisobutylmethacrylate, polyalginate, polyamide, and polysilicon.

In other embodiments, the dosage form can comprise a plurality of tiny pills. Tiny time-released pills can provide a number of individual doses characterized by different temporal release profiles for achieving a sustained-release profile over an extended period of time, such as up to 24 hours. The matrix can comprise a hydrophilic polymer, such as a polysaccharide, agar, agarose, natural gum, alkali alginate including sodium alginate, carrageenan, fucoidan, furcellaran, laminaran, hypnea, gum arabic, gum ghatti, gum karaya, gum tragacanth, locust bean gum, pectin, amylopectin, gelatin, or a hydrophilic colloid. A hydrophilic matrix can comprise a plurality of 4 to 50 tiny pills, each tiny pill containing a dose of from 10 ng, 0.5 mg, 1 mg, 1.2 mg, 1.4 mg, 1.6 mg, 5.0 mg, or greater. The tiny pills can comprise a release rate-controlling wall ranging from 0.001 mm to 10 mm thickness to enable the timed release of a compound of the present disclosure. Representative wall-forming materials include a triglyceryl ester such as glyceryl tristearate, glyceryl monostearate, glyceryl dipalmitate, glyceryl laureate, glyceryl didecenoate, and glyceryl tridenoate. Other wall-forming materials include polyvinyl acetate, phthalate, methylcellulose phthalate, and microporous olefins.

In other embodiments, the dosage form can comprise an osmotic dosage form, which can include a semipermeable wall surrounding a therapeutic composition comprising at least one compound of the present disclosure. An osmotic dosage form comprising a homogenous composition can imbibe fluid through the semipermeable wall into the dosage form in response to concentration gradients across the semipermeable wall. The therapeutic composition in the dosage form can develop osmotic energy that can cause the therapeutic composition to be administered through an exit from the dosage form over a prolonged period of time, such as up to 24 hours, to provide controlled and sustained release of a compound of the present disclosure.

In other embodiments, the dosage form can comprise an osmotic dosage form comprising a wall surrounding a compartment, the wall having a semipermeable polymeric composition permeable to the passage of fluid and impermeable to the passage of a compound of the present disclosure contained within the compartment, a compound-containing layer composition in the compartment, a hydrogel layer composition in the compartment comprising an osmotic formulation for imbibing and absorbing fluid for expanding in size for pushing the prodrug or derivative composition layer from the dosage form, and at least one passageway in the wall for releasing the composition containing a compound of the present disclosure. This method can deliver a compound of the present disclosure by imbibing fluid through the semipermeable wall at a fluid imbibing rate determined by the permeability of the semipermeable wall and the osmotic pressure across the semipermeable wall causing the push layer to expand, thereby delivering the compound from the dosage form through the exit passageway to a subject over a prolonged period of time, such as up to 24 hours.

The hydrogel layer composition can comprise 10 mg to 1,000 mg of a hydrogel such as a polyalkylene oxide of 1,000,000 to 8,000,000 weight-average molecular weight, for example, a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. The hydrogel expansion layer can comprise 0.1 mg to 350 mg of a polymer, for example, 0.1 mg to 250 mg of a hydroxyalkylcellulose of 7,500 to 4,500,00 weight-average molecular weight such as hydroxymethylcellulose, hydroxyethylcellulose, hydroxypropylcellulose, hydroxybutylcellulose or hydroxypentylcellulose; 0.1 mg to 50 mg of an osmagent chosen from sodium chloride, potassium chloride, potassium acid phosphate, tartaric acid, citric acid, raffinose, magnesium sulfate, magnesium chloride, urea, inositol, sucrose, glucose and sorbitol; 0.1 to 5 mg of a colorant, such as ferric oxide; 0.1 to 1.5 mg of an antioxidant including ascorbic acid, butylated hydroxyanisole, butylatedhydroxyquinone, butylhydroxyanisol, hydroxycoumarin, butylated hydroxytoluene, cephalm, ethyl gallate, propyl gallate, octyl gallate, lauryl gallate, propyl-hydroxybenzoate, trihydroxybutylrophenone, dimethylphenol, dibutylphenol, vitamin E, lecithin and ethanolamine; and 0.1 mg to 7 mg of a lubricant inluding calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

In the osmotic dosage forms, the semipermeable wall can comprise a composition that is permeable to the passage of fluid and impermeable to the passage of the compound of the present disclosure. The wall is nontoxic and comprises a polymer such as a cellulose acylate, cellulose diacylate, cellulose triacylate, cellulose acetate, cellulose diacetate or cellulose triacetate. The wall can comprise 75 wt % (weight percent) to 100 wt % of the cellulosic wall-forming polymer; or, the wall can additionally comprise 0.01 wt % to 80 wt % of polyethylene glycol, or 1 wt % to 25 wt % of a cellulose ether including, for example, hydroxypropylcellulose or a hydroxypropylalkycellulose such as hydroxypropylmethylcellulose. The total weight percent of all components comprising the wall is equal to 100 wt %. The internal compartment can comprise the compound or composition of the present disclosure alone or in layered position with an expandable hydrogel composition. The expandable hydrogel composition in the compartment can increase in dimension upon imbibing the fluid through the semipermeable wall, causing the hydrogel to expand and occupy space in the compartment, whereby a pharmaceutical composition is pushed from the dosage form. The therapeutic layer and the expandable layer can act together to release of a compound of the present disclosure to a subject over time. The dosage form comprises a passageway in the wall that connects the exterior of the dosage form with the internal compartment.

As used herein, "passageway" refers to means and methods suitable for the metered release of the chemical entities of the present disclosure from the compartment of the dosage form. The exit means can comprise at least one passageway, including orifice, bore, aperture, pore, porous element, hollow fiber, capillary tube, channel, porous overlay, or porous element that can provide for the osmotic controlled release of a compound of the present disclosure. The passageway can include a material that erodes or is leached from the wall in a fluid environment of use to produce at least one controlled-release dimensioned passageway. Representative materials suitable for forming a passageway, or a multiplicity of passageways include a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway can possess controlled-release dimensions, such as round, triangular, square and elliptical, for the metered release of a compound of the present disclosure from the dosage form. The dosage form can be constructed with one or more passageways in spaced apart relationship on a single surface or on more than one surface of the wall. As used herein, "fluid environment" refers to an aqueous or biological fluid as in a subject, including the gastrointestinal tract.

Regardless of the specific form of sustained release oral dosage form used, the compounds and composition of the present disclosure can be released from the dosage form over an extended period of time. In certain embodiments, sustained release oral dosage forms can provide a therapeutically effective amount of a compound of the present disclosure over a period of at least several hours. In certain embodiments the extended release dosage form can provide a constant therapeutically effective concentration of a compound of the present disclosure in the plasma of a subject for a prolonged period of time, such as at least several hours. In other embodiments, the sustained release oral dosage form can provide a controlled and constant concentration of a therapeutically effective amount of a compound of the present disclosure in the plasma of a subject.

Dosage forms comprising compositions and chemical entities of the present disclosure can be administered at certain intervals such as, for example, twice per day or once per day.

Exemplary dosage ranges for oral administration are dependent on the potency of the compound of the present disclosure, but can range from 0.1 mg to 20 mg of the compound per kilogram of body weight. Dosage ranges may be readily determined by methods known to those skilled in the art.

Chemical entities of the present disclosure can be assayed in vitro and in vivo, to determine and optimize therapeutic or prophylactic activity prior to use in subjects. For example, in vitro assays can be used to determine whether administration of a specific compound of the present disclosure or a combination of such compounds exhibits therapeutic efficacy. Chemical entities of the present disclosure can also be demonstrated to be effective and safe using animal model systems.

It is desirable that a therapeutically effective dose of a compound of the present disclosure provide therapeutic benefit without causing substantial toxicity. Toxicity of chemical entities of the present disclosure can be determined using standard pharmaceutical procedures and can be readily ascertained by the skilled artisan. The dose ratio between toxic and therapeutic effect is the therapeutic index. In certain embodiments, chemical entities of the present disclosure can exhibit particularly high therapeutic indices in treating diseases and disorders. In certain embodiments, the dosage of a compound of the present disclosure can be within a range of circulating concentrations that exhibit therapeutic efficacy with limited or no toxicity.

EXAMPLES

Embodiments of the present disclosure can be further defined by reference to the following examples, which describe in detail preparation of compounds of the present disclosure and assays for using compounds of the present disclosure. It will be apparent to those skilled in the art that many modifications, both to materials and methods, may be practiced without departing from the scope of the present disclosure.

In the examples below, the following abbreviations have the following meanings. If an abbreviation is not defined, it has its generally accepted meaning.

| | |
|---|---|
| AcOH = | acetic acid |
| Atm = | atmosphere |
| ATP = | adenosine triphosphate |
| Boc = | tert-butyloxycarbonyl |
| BSA = | bovine serum albumin |
| Da = | Dalton |
| DMF = | N,N-dimethylformamide |
| DMSO = | dimethylsulfoxide |
| DTT = | (R,R)-dithiothrietol |
| EDTA = | ethylenediaminetetraacetic acid |
| EtOAc = | ethyl acetate |
| g = | gram |
| HCl = | hydrochloric acid |
| hr = | hour |
| HEPES = | [4-(2-hydroxyethyl)-1-piperazineethanesulfonic acid |
| HPLC = | high performance liquid chromatography |
| HTS = | high throughput screen |
| i-PrOH = | isopropanol |
| kDa = | kilo Dalton |
| $K_2CO_3$ = | potassium carbonate |
| L = | liter |
| LC/MS = | liquid chromatography/mass spectroscopy |
| M = | molar |
| $MgSO_4$ = | magnesium sulfate |
| MeOH = | methanol |
| MS = | mass spectroscopy |
| mg = | milligram |
| min = | minute |
| mL = | milliliter |
| mm = | millimeter |
| mmol = | millimoles |
| mM = | millimolar |
| nM = | nanomolar |
| $NaHCO_3$ = | sodium bicarbonate |
| NaOH = | sodium hydroxide |
| NMP = | N-methylpyrrolidinone |
| µL = | microliter |
| µM = | micromolar |
| psi = | pounds per square inch |
| RT = | room temperature |
| TCB = | trough circulating buffer |
| THF = | tetrahydrofuran |
| TFA = | trifluoroacetic acid |

| | |
|---|---|
| TLC = | thin layer chromatography |
| TMS = | trimethylsilyl |
| UV = | ultraviolet |
| v/c = | volume to volume |
| W = | watt |

General Procedure for Solution Phase Parallel Synthesis (R¹ and Z Group Variation)

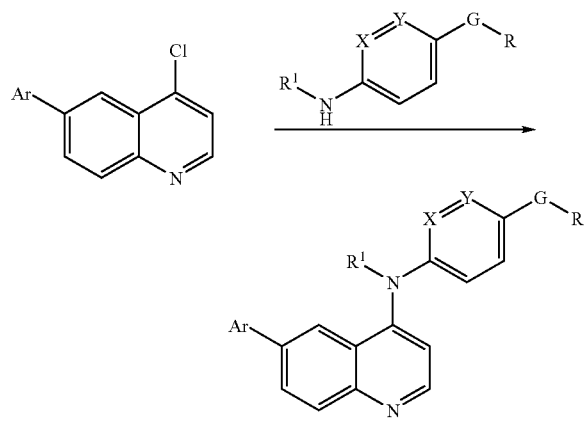

A mixture of the appropriate chloroquinoline derivative (3 mg, 0.01 mmol) and the appropriate aniline derivative (0.02 mmol) were dissolved in NMP (300 μL) followed by N,N-diisopropylethylamine (17 μL, 0.1 mmol). The reaction mixture was irradiated in a microwave oven (max. power 250 W, 180° C.) for 5 min, cooled to room temperature, and concentrated in vacuo. The resulting residue was dissolved in DMSO (200 μL) and subjected to HPLC purification (Method B) to provide the desired coupled product.

General Procedure for Solution Phase Parallel Synthesis (Ar Group Variation)

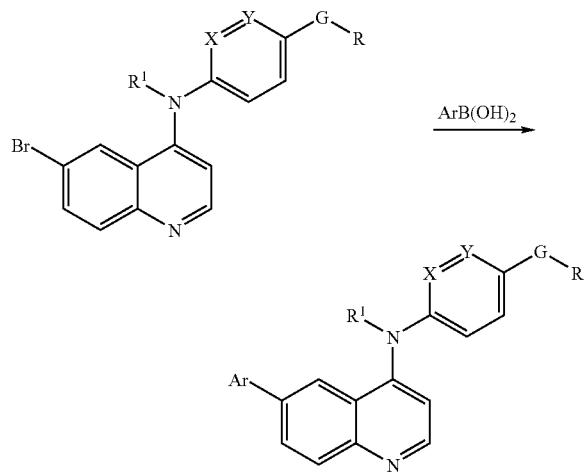

A mixture of the appropriate bromoquinoline derivative (3 mg, 0.008 mmol) and the appropriate arylboronic acid (0.02 mmol) was dissolved in NMP (300 μL) followed by addition of cesium carbonate (10 mg, 0.31 mmol) and tetrakis(triphenylphosphine)palladium(0) (1 mg, 0.0006 mmol). The reaction mixture was irradiated in a microwave oven (max. power 250 W, 160° C.) for 5 min, cooled to room temperature, and concentrated in vacuo. The resulting residue was dissolved in DMSO (200 μL) and subjected to HPLC purification (Method B) to provide the desired coupled product.

Example 1

Synthesis of (101)

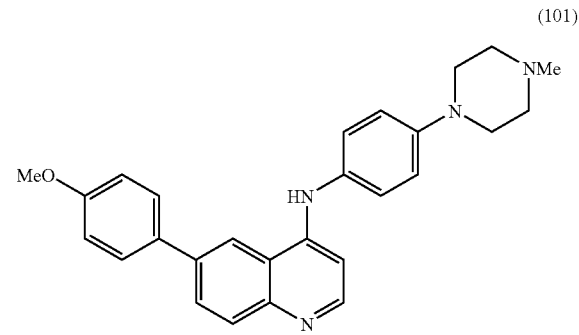

(101)

Step A: Synthesis of (102)

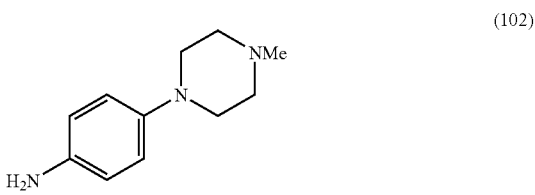

(102)

A mixture of 1-fluoro-4-nitrobenzene (2.54 mL, 24 mmol) and N-methylpiperazine (2.22 mL, 20 mmol) was dissolved in DMSO (25 mL) and irradiated in a microwave oven (max power 250 W, 160° C.) for 10 min, then cooled to room temperature. The solvent was removed under high vacuum, and the residue was dissolved in EtOAc and extracted with 0.5M aqueous HCl. The aqueous extracts were combined, basified to pH 8, and extracted with EtOAc. The organic layer was washed with brine, and then dried over MgSO₄. Evaporation of the solvent provided the crude 1-methyl-4-(4-nitrophenyl)piperazine as an brown oil.

A mixture of the crude intermediate and 5% palladium on carbon (1 g) in MeOH (80 mL) was hydrogenated on a Parr shaker at room temperature at 80 psi for 1 h, and then filtered. The filtrate was treated with 1N aqueous HCl, concentrated in vacuo, and the residue was triturated with i-PrOH. The crude solid was recrystallized from i-PrOH/ether to provide 102 (3.43 g) as the hydrochloride salt.

Step B: Synthesis of (103)

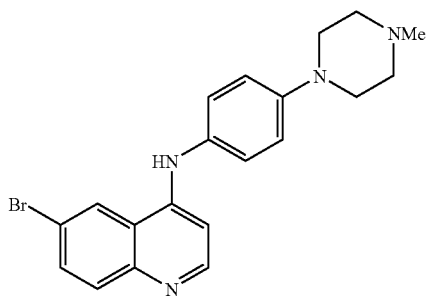
(103)

A mixture of 6-bromo-4-chloroquinoline (242 mg, 1 mmol) (prepared according to *J. Med. Chem.* 1978, 21, 268-272) and 102 (598 mg, 2 mmol) was dissolved in DMSO (3 mL), followed by addition of N,N-diisopropylethylamine (1,218 μL, 7 mmol). The reaction mixture was irradiated in a microwave oven (max. power 250 W, 180° C.) for 5 min, cooled to room temperature, and concentrated in vacuo. The resulting residue was subjected to HPLC purification (Method A). Fractions containing the desired product were combined and concentrated in vacuo. A solution of 1M aqueous HCl was added to the residue and the mixture was concentrated in vacuo. The resulting residue was dissolved in a mixture of acetonitrile/water (1:4) and lyophilized to provide the dihydrochloride salt of 103 (342 mg, 73%) as a yellow powder.

Step C: Synthesis of (101)

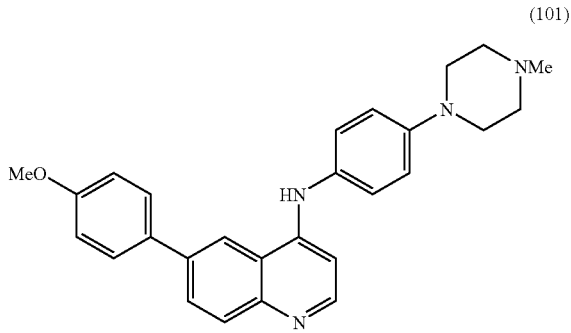
(101)

A mixture of 103 (469 mg, 1 mmol) and 4-methoxyphenylboronic acid (304 mg, 2 mmol) was dissolved in acetonitrile (8 mL), followed by addition of 1M aqueous $K_2CO_3$ (4 mL) and tetrakis(triphenylphosphine) palladium(0) (10 mg, 0.009 mmol). The reaction mixture was irradiated in a microwave oven (max. power 250 W, 160° C.) for 6 min, cooled to room temperature, and concentrated in vacuo. The resulting residue was subjected to HPLC purification (Method A). Fractions containing 101 were combined and concentrated in vacuo. A solution of 1M aqueous HCl was added to the residue and the mixture was concentrated in vacuo. The resulting residue was dissolved in a mixture of acetonitrile/water (1:4) and lyophilized to provide the dihydrochloride salt of the title compound (312 mg, 63%) as a yellow powder. LC/MS (ESI) m/z 425 [M+H]. HPLC retention time=2.46 min.

Example 2

Synthesis of (104)

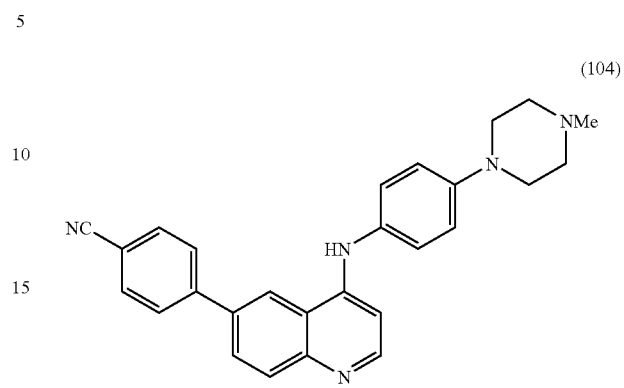
(104)

Step A: Synthesis of (105)

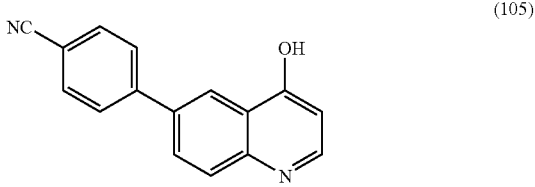
(105)

A mixture of 6-bromo-4-hydroxyquinoline (224 mg, 1 mmol) and 4-cyanophenylboronic acid (282 mg, 2 mmol) were dissolved in acetonitrile (8 mL), followed by addition of 1M aqueous $K_2CO_3$ (4 mL) and tetrakis(triphenylphosphine) palladium(0) (10 mg, 0.009 mmol). The reaction mixture was irradiated in a microwave oven (max. power 250 W, 160° C.) for 6 min, cooled to room temperature, and then concentrated in vacuo. Water was added to the resulting residue and the mixture was extracted with EtOAc. The aqueous layer was adjusted to pH 7 with 0.5M aqueous HCl, at which time the product precipitated from the mixture. The resulting solid was filtered, washed with water, and dried in vacuo to provide 105 (185 mg, 75%) as a grey powder.

Step B: Synthesis of (106)

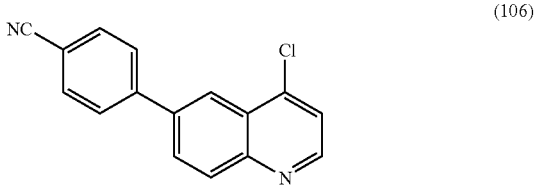
(106)

A mixture of 105 (185 mg, 0.75 mmol) and phosphorus oxychloride (5 mL) was heated at reflux for 20 min, cooled to room temperature, and concentrated in vacuo. The resulting residue was treated with ice water (20 mL) and the mixture was adjusted to pH 7 with 0.5M aqueous NaOH. The resulting solid was filtered, washed with water, and dried in vacuo to provide 106 (130 mg, 65%) as a grey powder.

Step C: Synthesis of (104)

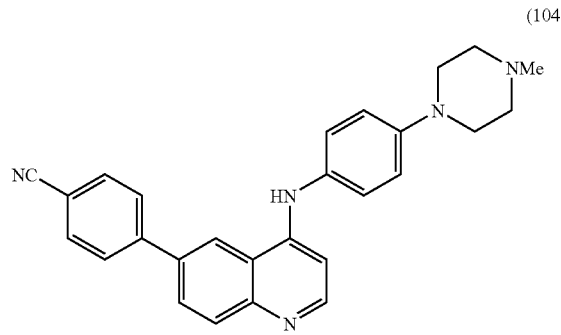

A mixture of 106 (264 mg, 1 mmol) and 102 (598 mg, 2 mmol) was dissolved in DMSO (3 mL), followed by addition of N,N-diisopropylethylamine (1.22 mL, 7 mmol). The reaction mixture was irradiated in a microwave oven (max. power 250 W, 180° C.) for 5 min, cooled to room temperature, and concentrated in vacuo. The resulting residue was subjected to HPLC purification (Method A). Fractions containing the desired product were combined and concentrated in vacuo. A solution of 1M aqueous HCl was added to the residue and the mixture was concentrated in vacuo. The resulting residue was dissolved in a mixture of acetonitrile/water (1:4) and lyophilized to provide the title compound (368 mg, 75%) as a yellow powder as the dihydrochloride salt. LC/MS (ESI) m/z 420 [M+H]. HPLC retention time=2.38 min.

Example 3

Synthesis of (107)

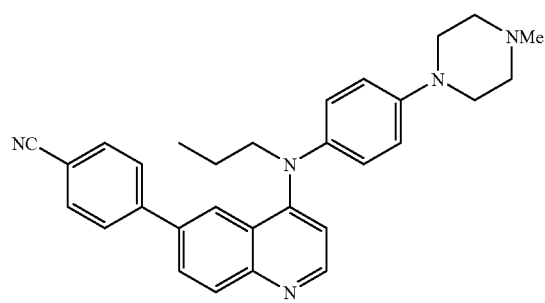

Step A: Synthesis of (108)

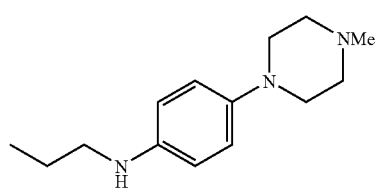

A solution of 102 (150 mg, 0.5 mmol) in N,N-dimethylacetamide (5 mL) was treated with 1-bromopropane (110 μL, 1.2 mmol), and the mixture was heated at 50° C. overnight. The reaction mixture was cooled to room temperature, concentrated in vacuo, and the residue was subjected to HPLC purification (Method A). Fractions containing the desired product were combined and concentrated in vacuo. The residue was dissolved in MeOH (1 mL) and 1M HCl/ether (50 mL) was added. The solvents were decanted and the resulting oil was dried in vacuo to provide 108 (21 mg, 12%) as a colorless amorphous solid as the hydrochloride salt.

Step B: Syntheis of (107)

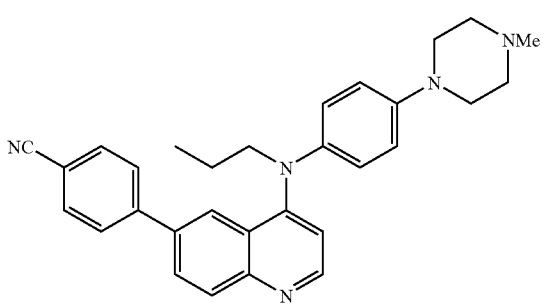

Following the procedure in Example 2, 108 was coupled to provide 1.2 mg (61%) of the title compound as a yellow amorphous solid. LC/MS (ESI) m/z 462 [M+H]. HPLC retention time=2.31 min.

Example 4

The compounds listed below were prepared by the general procedures as set forth in the General Procedures and as exemplified in Examples 2 and 3, utilizing the appropriate starting materials.

| Compound | LC/MS m/z [M + H] | HPLC retention time (min) |
|---|---|---|
| N-(4-(4-methylpiperazin-1-yl)phenyl)-6-phenylquinolin-4-amine | 395.1 | 2.31 |
| 6-(3-chlorophenyl)-N-(4-(4-methylpiperazin-1-yl)phenyl)quinolin-4-amine | 429.1 | 2.52 |
| 6-(4-chlorophenyl)-N-(4-(4-methylpiperazin-1-yl)phenyl)quinolin-4-amine | 429.1 | 2.52 |
| N-(4-(4-methylpiperazin-1-yl)phenyl)-6-o-tolylquinolin-4-amine | 409.5 | 2.42 |
| N-(4-(4-methylpiperazin-1-yl)phenyl)-6-m-tolylquinolin-4-amine | 409.5 | 2.48 |
| N-(4-(4-methylpiperazin-1-yl)phenyl)-6-p-tolylquinolin-4-amine | 409.5 | 2.48 |
| 6-(2-methoxyphenyl)-N-(4-(4-methylpiperazin-1-yl)phenyl)quinolin-4-amine | 425.1 | 2.35 |
| 6-(3-methoxyphenyl)-N-(4-(4-methylpiperazin-1-yl)phenyl)quinolin-4-amine | 425.1 | 2.36 |
| 2-(4-(4-(4-methylpiperazin-1-yl)phenylamino)quinolin-6-yl)benzamide | 438.3 | 1.87 |
| 3-(4-(4-(4-methylpiperazin-1-yl)phenylamino)quinolin-6-yl)benzonitrile | 420.3 | 2.29 |
| 6-(3,4-dimethoxyphenyl)-N-(4-(4-methylpiperazin-1-yl)phenyl)quinolin-4-amine | 455.1 | 2.22 |
| 6-(2,4-difluorophenyl)-N-(4-(4-methylpiperazin-1-yl)phenyl)quinolin-4-amine | 431.1 | 2.36 |

-continued

| Compound | LC/MS m/z [M + H] | HPLC retention time (min) |
| --- | --- | --- |
| 6-(4-fluoro-3-methylphenyl)-N-(4-(4-methylpiperazin-1-yl)phenyl)quinolin-4-amine | 427.1 | 2.58 |
| (3-(4-(4-(4-methylpiperazin-1-yl)phenylamino)quinolin-6-yl)phenyl)methanol | 425.1 | 2.05 |
| 6-(5-fluoro-2-methoxyphenyl)-N-(4-(4-methylpiperazin-1-yl)phenyl)quinolin-4-amine | 443.5 | 2.39 |
| 3-(4-(4-(4-methylpiperazin-1-yl)phenylamino)quinolin-6-yl)phenol | 411.1 | 2.09 |
| 6-(3-chloro-4-fluorophenyl)-N-(4-(4-methylpiperazin-1-yl)phenyl)quinolin-4-amine | 447.1 | 2.53 |
| 4-(4-(4-(4-methylpiperazin-1-yl)phenylamino)quinolin-6-yl)phenol | 411.1 | 2.05 |
| 6-(2,3-dimethylphenyl)-N-(4-(4-methylpiperazin-1-yl)phenyl)quinolin-4-amine | 423.1 | 2.53 |
| 6-(2,5-dimethoxyphenyl)-N-(4-(4-methylpiperazin-1-yl)phenyl)quinolin-4-amine | 455.1 | 2.36 |
| 6-(2-ethylphenyl)-N-(4-(4-methylpiperazin-1-yl)phenyl)quinolin-4-amine | 423.1 | 2.51 |
| 4-(4-(4-(4-methylpiperazin-1-yl)phenylamino)quinolin-6-yl)benzamide | 438.3 | 1.89 |
| 6-(4-(ethylthio)phenyl)-N-(4-(4-methylpiperazin-1-yl)phenyl)quinolin-4-amine | 455.1 | 2.65 |
| 6-(3,5-difluorophenyl)-N-(4-(4-methylpiperazin-1-yl)phenyl)quinolin-4-amine | 431.5 | 2.46 |
| 6-(biphenyl-2-yl)-N-(4-(4-methylpiperazin-1-yl)phenyl)quinolin-4-amine | 471.5 | 2.65 |
| 6-(2,5-difluorophenyl)-N-(4-(4-methylpiperazin-1-yl)phenyl)quinolin-4-amine | 431.1 | 2.36 |
| 6-(4-fluorophenyl)-N-(4-(4-methylpiperazin-1-yl)phenyl)quinolin-4-amine | 413.1 | 2.38 |
| 6-(2,3-dichlorophenyl)-N-(4-(4-methylpiperazin-1-yl)phenyl)quinolin-4-amine | 463.1 | 2.58 |
| 6-(2,5-dimethylphenyl)-N-(4-(4-methylpiperazin-1-yl)phenyl)quinolin-4-amine | 423.1 | 2.55 |
| 3-(4-(4-(4-methylpiperazin-1-yl)phenylamino)quinolin-6-yl)benzoic acid | 439.1 | 2.20 |
| N-(4-(4-methylpiperazin-1-yl)phenyl)-6-(4-(methylthio)phenyl)quinolin-4-amine | 441.1 | 2.50 |
| 6-(3-ethoxyphenyl)-N-(4-(4-methylpiperazin-1-yl)phenyl)quinolin-4-amine | 439.5 | 2.48 |
| N-(4-(4-methylpiperazin-1-yl)phenyl)-6-(2-(trifluoromethyl)phenyl)quinolin-4-amine | 463.1 | 2.46 |
| 6-(3-(benzyloxy)phenyl)-N-(4-(4-methylpiperazin-1-yl)phenyl)quinolin-4-amine | 501.1 | 2.81 |
| N-(4-(4-methylpiperazin-1-yl)phenyl)-6-(4-vinylphenyl)quinolin-4-amine | 421.1 | 2.53 |
| 6-(2,4-dimethoxyphenyl)-N-(4-(4-methylpiperazin-1-yl)phenyl)quinolin-4-amine | 455.1 | 2.39 |
| N-(4-(4-methylpiperazin-1-yl)phenyl)-6-(3,4,5-trifluorophenyl)quinolin-4-amine | 449.1 | 2.53 |
| (4-(4-(4-methylpiperazin-1-yl)phenylamino)quinolin-6-yl)phenyl)methanol | 425.1 | 1.99 |
| N-(4-(4-methylpiperazin-1-yl)phenyl)-6-(4-phenoxyphenyl)quinolin-4-amine | 487.5 | 2.79 |
| 6-(4-ethoxyphenyl)-N-(4-(4-methylpiperazin-1-yl)phenyl)quinolin-4-amine | 439.5 | 2.50 |
| 6-(3,4-dichlorophenyl)-N-(4-(4-methylpiperazin-1-yl)phenyl)quinolin-4-amine | 463.1 | 2.65 |
| N-(4-(4-methylpiperazin-1-yl)phenyl)-6-(4-(trifluoromethyl)phenyl)quinolin-4-amine | 463.1 | 2.62 |
| 6-(2,5-dichlorophenyl)-N-(4-(4-methylpiperazin-1-yl)phenyl)quinolin-4-amine | 463.1 | 2.62 |
| 6-(2,4-dichlorophenyl)-N-(4-(4-methylpiperazin-1-yl)phenyl)quinolin-4-amine | 463.1 | 2.62 |
| 6-(3-isopropylphenyl)-N-(4-(4-methylpiperazin-1-yl)phenyl)quinolin-4-amine | 437.1 | 2.72 |
| 6-(4-isopropylphenyl)-N-(4-(4-methylpiperazin-1-yl)phenyl)quinolin-4-amine | 437.1 | 2.75 |
| 6-(4-fluoro-2-methylphenyl)-N-(4-(4-methylpiperazin-1-yl)phenyl)quinolin-4-amine | 427.1 | 2.49 |
| 6-(3,4-difluorophenyl)-N-(4-(4-methylpiperazin-1-yl)phenyl)quinolin-4-amine | 431.5 | 2.48 |
| 6-(biphenyl-3-yl)-N-(4-(4-methylpiperazin-1-yl)phenyl)quinolin-4-amine | 471.5 | 2.78 |
| 6-(5-isopropyl-2-methoxyphenyl)-N-(4-(4-methylpiperazin-1-yl)phenyl)quinolin-4-amine | 467.5 | 2.72 |
| N-(3-(4-(4-(4-methylpiperazin-1-yl)phenylamino)quinolin-6-yl)phenyl)acetamide | 452.3 | 2.06 |
| 6-(2,4-bis(trifluoromethyl)phenyl)-N-(4-(4-methylpiperazin-1-yl)phenyl)quinolin-4-amine | 531.1 | 2.83 |
| N-(4-(4-methylpiperazin-1-yl)phenyl)-6-(4-(methylsulfinyl)phenyl)quinolin-4-amine | 457.5 | 1.93 |
| N-(4-(4-methylpiperazin-1-yl)phenyl)-6-(4-pentylphenyl)quinolin-4-amine | 465.5 | 3.05 |
| 6-(3,5-bis(trifluoromethyl)phenyl)-N-(4-(4-methylpiperazin-1-yl)phenyl)quinolin-4-amine | 531.1 | 2.83 |
| 6-(4-butylphenyl)-N-(4-(4-methylpiperazin-1-yl)phenyl)quinolin-4-amine | 451.1 | 2.99 |
| 3-(4-(4-(4-methylpiperazin-1-yl)phenylamino)quinolin-6-yl)phenyl)propanoic acid | 467.1 | 2.19 |
| N-(4-(4-methylpiperazin-1-yl)phenyl)-6-(3-nitrophenyl)quinolin-4-amine | 440.3 | 2.35 |
| 6-(3-fluorophenyl)-N-(4-(4-methylpiperazin-1-yl)phenyl)quinolin-4-amine | 413.1 | 2.39 |
| 6-(2-fluorophenyl)-N-(4-(4-methylpiperazin-1-yl)phenyl)quinolin-4-amine | 413.1 | 2.32 |
| 6-(4-tert-butylphenyl)-N-(4-(4-methylpiperazin-1-yl)phenyl)quinolin-4-amine | 451.1 | 2.82 |
| N-(4-(4-methylpiperazin-1-yl)phenyl)-6-(3-(trifluoromethoxy)phenyl)quinolin-4-amine | 479.1 | 2.66 |
| N-(4-(4-methylpiperazin-1-yl)phenyl)-6-(4-(trifluoromethoxy)phenyl)quinolin-4-amine | 479.1 | 2.66 |
| 6-(2,6-difluorophenyl)-N-(4-(4-methylpiperazin-1-yl)phenyl)quinolin-4-amine | 431.5 | 2.32 |
| N-(4-(4-methylpiperazin-1-yl)phenyl)-6-(3-(trifluoromethyl)phenyl)quinolin-4-amine | 463.1 | 2.58 |
| 6-(4-(benzyloxy)phenyl)-N-(4-(4-methylpiperazin-1-yl)phenyl)quinolin-4-amine | 501.1 | 2.82 |
| 6-(2-((dimethylamino)methyl)phenyl)-N-(4-(4-methylpiperazin-1-yl)phenyl)quinolin-4-amine | 452.3 | 1.86 |
| 6-(4-(benzyloxy)-3-fluorophenyl)-N-(4-(4-methylpiperazin-1-yl)phenyl)quinolin-4-amine | 519.1 | 2.83 |
| 6-(4-cyclohexylphenyl)-N-(4-(4-methylpiperazin-1-yl)phenyl)quinolin-4-amine | 477.1 | 3.06 |
| 6-(3,4-dimethyl)-N-(4-(4-methylpiperazin-1-yl)phenyl)quinolin-4-amine | 423.1 | 2.61 |
| 6-phenyl-N-(4-(piperazin-1-yl)phenyl)quinolin-4-amine | 381.1 | 2.26 |
| N-(4-(4-ethylpiperazin-1-yl)phenyl)-6-phenylquinolin-4-amine | 409.5 | 2.33 |
| 6-phenyl-N-(4-(4-propylpiperazin-1-yl)phenylquinolin-4-amine | 423.1 | 2.38 |
| N-(4-(4-butylpiperazin-1-yl)phenyl)-6-phenylquinolin-4-amine | 437.1 | 2.48 |
| N-(4-(4-isopropylpiperazin-1-yl)phenyl)-6-phenylquinolin-4-amine | 423.1 | 2.36 |
| N-(4-(4-(pentan-3-yl)piperazin-1-yl)phenyl)-6-phenylquinolin-4-amine | 451.1 | 2.49 |
| 2-(4-(4-(6-phenylquinolin-4-ylamino)phenyl)piperazin-1-yl)ethanol | 425.1 | 2.28 |
| N-(4-(4-(2-methoxyethyl)piperazin-1-yl)phenyl)-6-phenylquinolin-4-amine | 439.5 | 2.35 |
| 3-(4-(4-(6-phenylquinolin-4-ylamino)phenyl)piperazin-1-yl)propan-1-ol | 439.5 | 2.29 |
| N-(4-(4-(2-(dimethylamino)ethyl)piperazin-1-yl)phenyl)-6-phenylquinolin-4-amine | 452.3 | 2.20 |
| 3-(4-(4-(6-phenylquinolin-4-ylamino)phenyl)piperazin-1-yl)propanenitrile | 434.3 | 2.33 |
| 2-(4-(4-(6-phenylquinolin-4-ylamino)phenyl)piperazin-1-yl)acetic acid | 439.5 | 2.32 |
| 6-(4-methoxyphenyl)-N-(4-(piperazin-1-yl)phenyl)quinolin-4-amine | 411.1 | 2.30 |
| N-(4-(4-ethylpiperazin-1-yl)phenyl)-6-(4-methoxyphenyl)quinolin-4-amine | 439.5 | 2.35 |
| 6-(4-methoxyphenyl)-N-(4-(4-propylpiperazin-1-yl)phenyl)quinolin-4-amine | 453.1 | 2.40 |
| N-(4-(4-butylpiperazin-1-yl)phenyl)-6-(4-methoxyphenyl)quinolin-4-amine | 467.5 | 2.51 |

| Compound | LC/MS m/z [M + H] | HPLC retention time (min) |
|---|---|---|
| N-(4-(4-isopropylpiperazin-1-yl)phenyl)-6-(4-methoxyphenyl)quinolin-4-amine | 453.1 | 2.39 |
| 2-(4-(6-(4-methoxyphenyl)quinolin-4-ylamino)phenyl)piperazin-1-yl)ethanol | 455.1 | 2.30 |
| 3-(4-(6-(4-methoxyphenyl)quinolin-4-ylamino)phenyl)piperazin-1-yl)propan-1-ol | 469.5 | 2.32 |
| N-(4-(4-(2-(dimethylamino)ethyl)piperazin-1-yl)phenyl)-6-(4-methoxyphenyl)quinolin-4-amine | 482.3 | 2.22 |
| 3-(4-(6-(4-methoxyphenyl)quinolin-4-ylamino)phenyl)piperazin-1-yl)propanenitrile | 464.3 | 2.36 |
| 2-(4-(4-(6-(4-methoxyphenyl)quinolin-4-ylamino)phenyl)piperazin-1-yl)-N,N-dimethylacetamide | 496.3 | 2.36 |
| 2-(4-(4-(6-(4-methoxyphenyl)quinolin-4-ylamino)phenyl)piperazin-1-yl)acetic acid | 469.5 | 2.32 |
| 4-(4-(piperazin-1-yl)phenylamino)quinolin-6-yl)benzonitrile | 406.3 | 2.21 |
| 4-(4-(4-ethylpiperazin-1-yl)phenylamino)quinolin-6-yl)benzonitrile | 434.3 | 2.26 |
| 4-(4-(4-propylpiperazin-1-yl)phenylamino)quinolin-6-yl)benzonitrile | 448.3 | 2.30 |
| 4-(4-(4-butylpiperazin-1-yl)phenylamino)quinolin-6-yl)benzonitrile | 462.3 | 2.40 |
| 4-(4-(4-sec-butylpiperazin-1-yl)phenylamino)quinolin-6-yl)benzonitrile | 462.3 | 2.36 |
| 4-(4-(4-(pentan-3-yl)piperazin-1-yl)phenylamino)quinolin-6-yl)benzonitrile | 476.3 | 2.45 |
| 4-(4-(4-allylpiperazin-1-yl)phenylamino)quinolin-6-yl)benzonitrile | 446.3 | 2.32 |
| 4-(4-(4-cyclohexylpiperazin-1-yl)phenylamino)quinolin-6-yl)benzonitrile | 488.3 | 2.48 |
| 4-(4-(4-(2-hydroxyethyl)piperazin-1-yl)phenylamino)quinolin-6-yl)benzonitrile | 450.3 | 2.19 |
| 4-(4-(4-(3-hydroxypropyl)piperazin-1-yl)phenylamino)quinolin-6-yl)benzonitrile | 464.3 | 2.20 |
| 4-(4-(4-(2-(dimethylamino)ethyl)piperazin-1-yl)phenylamino)quinolin-6-yl)benzonitrile | 477.1 | 2.12 |
| 4-(4-(4-(2-cyanoethyl)piperazin-1-yl)phenylamino)quinolin-6-yl)benzonitrile | 459.5 | 2.26 |
| 2-(4-(4-(6-(4-cyanophenyl)quinolin-4-ylamino)phenyl)piperazin-1-yl)acetic acid | 464.3 | 2.22 |
| N-(4-(4-sec-butylpiperazin-1-yl)phenyl)-6-phenylquinolin-4-amine | 437.1 | 2.42 |
| N-(4-(4-cyclopentylpiperazin-1-yl)phenyl)-6-phenylquinolin-4-amine | 449.1 | 2.45 |
| N-(4-(4-cyclohexylpiperazin-1-yl)phenyl)-6-phenylquinolin-4-amine | 463.5 | 2.55 |
| N-(4-(4-sec-butylpiperazin-1-yl)phenyl)-6-(4-methoxyphenyl)quinolin-4-amine | 467.5 | 2.45 |
| N-(4-(4-cyclopentylpiperazin-1-yl)phenyl)-6-(4-methoxyphenyl)quinolin-4-amine | 479.1 | 2.48 |
| N-(4-(4-cyclohexylpiperazin-1-yl)phenyl)-6-(4-methoxyphenyl)quinolin-4-amine | 493.5 | 2.55 |
| 4-(4-(4-isopropylpiperazin-1-yl)phenylamino)quinolin-6-yl)benzonitrile | 448.3 | 2.30 |
| 4-(4-(4-cyclopentylpiperazin-1-yl)phenylamino)quinolin-6-yl)benzonitrile | 474.3 | 2.39 |
| 4-(4-(4-(2-methoxyethyl)piperazin-1-yl)phenylamino)quinolin-6-yl)benzonitrile | 464.3 | 2.26 |
| 2-(4-(4-(6-(4-cyanophenyl)quinolin-4-ylamino)phenyl)piperazin-1-yl)-N,N-dimethylacetamide | 491.1 | 2.26 |
| N-(4-(4-methylpiperazin-1-yl)phenyl)-6-(naphthalen-2-yl)quinolin-4-amine | 445.5 | 2.62 |
| N-(4-(4-methylpiperazin-1-yl)phenyl)-6-(naphthalen-1-yl)quinolin-4-amine | 445.5 | 2.56 |
| N-(4-(4-methylpiperazin-1-yl)phenyl)-6-(thiophen-2-yl)quinolin-4-amine | 401.1 | 2.26 |
| N-(4-(4-methylpiperazin-1-yl)phenyl)-6-(thiophen-3-yl)quinolin-4-amine | 401.1 | 2.26 |
| 6-(furan-2-yl)-N-(4-(4-methylpiperazin-1-yl)phenyl)quinolin-4-amine | 385.1 | 2.18 |
| 6-(furan-3-yl)-N-(4-(4-methylpiperazin-1-yl)phenyl)quinolin-4-amine | 385.1 | 2.16 |
| N-(4-(4-methylpiperazin-1-yl)phenyl)-6-(pyridin-3-yl)quinolin-4-amine | 396.3 | 1.57 |
| N-(4-(4-methylpiperazin-1-yl)phenyl)-6-(pyridin-4-yl)quinolin-4-amine | 396.3 | 1.57 |
| 6-(benzo[b]thiophen-3-yl)-N-(4-(4-methylpiperazin-1-yl)phenyl)quinolin-4-amine | 451.1 | 2.55 |
| 1-(5-(4-(4-(4-methylpiperazin-1-yl)phenylamino)quinolin-6-yl)thiophen-2-yl)ethanone | 443.5 | 2.22 |
| 6-(benzo[b]thiophen-2-yl)-N-(4-(4-methylpiperazin-1-yl)phenyl)quinolin-4-amine | 451.1 | 2.59 |
| 6-(5-chlorothiophen-2-yl)-N-(4-(4-methylpiperazin-1-yl)phenyl)quinolin-4-amine | 435.1 | 2.52 |
| N-(4-(4-methylpiperazin-1-yl)phenyl)-6-(4-methylthiophen-2-yl)quinolin-4-amine | 415.1 | 2.42 |
| N-(4-(4-methylpiperazin-1-yl)phenyl)-6-(pyrimidin-5-yl)quinolin-4-amine | 397.1 | 1.77 |
| N-(4-(4-methylpiperazin-1-yl)phenyl)-6,8'-biquinolin-4-amine | 446.3 | 1.92 |
| N-methyl-N-(4-(4-methylpiperazin-1-yl)phenyl)-6-phenylquinolin-4-amine | 409.5 | 2.10 |
| N-(4-(4-methylpiperazin-1-yl)phenyl)-6-phenyl-N-propylquinolin-4-amine | 437.1 | 2.29 |
| 6-(4-methoxyphenyl)-N-methyl-N-(4-(4-methylpiperazin-1-yl)phenyl)quinolin-4-amine | 439.5 | 2.16 |
| 6-(4-methoxyphenyl)-N-(4-(4-methylpiperazin-1-yl)phenyl)-N-propylquinolin-4-amine | 467.5 | 2.35 |
| 4-(4-(methyl(4-(4-methylpiperazin-1-yl)phenyl)amino)quinolin-6-yl)benzonitrile | 434.3 | 2.09 |
| 4-(4-(4-methylpiperidin-1-yl)phenylamino)quinolin-6-yl)benzonitrile | 419.1 | 2.29 |
| 4-(4-(4-(dimethylamino)piperidin-1-yl)phenylamino)quinolin-6-yl)benzonitrile | 448.3 | 2.22 |
| 4-(4-(4-(2-((dimethylamino)methyl)pyrrolidin-1-yl)phenylamino)quinolin-6-yl)benzonitrile | 448.3 | 2.39 |
| 4-(4-(4-(3-((dimethylamino)methyl)piperidin-1-yl)phenylamino)quinolin-6-yl)benzonitrile | 462.3 | 2.19 |
| 4-(4-(4-((dimethylamino)methyl)piperidin-1-yl)phenylamino)quinolin-6-yl)benzonitrile | 462.3 | 2.03 |
| 4-(4-(3-(dimethylamino)piperidin-1-yl)phenylamino)quinolin-6-yl)benzonitrile | 448.3 | 2.42 |
| 4-(4-(3-(dimethylamino)pyrrolidin-1-yl)phenylamino)quinolin-6-yl)benzonitrile | 434.3 | 2.30 |
| 4-(4-(3-(methylamino)pyrrolidin-1-yl)phenylamino)quinolin-6-yl)benzonitrile | 420.3 | 2.30 |
| N1-methyl-N4-(6-(5-methylpyridin-2-yl)quinolin-4-yl)-N1-(1-methylpyrrolidin-3-yl)benzene-1,4-diamine | 424.3 | 1.85 |
| 4-(4-(4-(methyl(1-methylpyrrolidin-3-yl)amino)phenylamino)quinolin-6-yl)benzonitrile | 434.3 | 2.29 |
| N1-(3,6'-biquinolin-4'-yl)-N4-methyl-N4-(1-methylpyrrolidin-3-yl)benzene-1,4-diamine | 460.3 | 1.99 |
| 4-(4-(6-(4-methylpiperazin-1-yl)pyridin-3-ylamino)quinolin-6-yl)benzonitrile | 421.1 | 2.06 |
| 6-(4-chlorophenyl)-N-(6-(4-methylpiperazin-1-yl)pyridin-3-yl)quinolin-4-amine | 430.3 | 2.32 |
| 4-(4-(6-(4-methylpiperazin-1-yl)pyridazin-3-ylamino)quinolin-6-yl)benzonitrile | 421.9 | 1.93 |
| 6-(1H-indol-4-yl)-N-(4-(4-methylpiperazin-1-yl)phenyl)quinolin-4-amine | 434.3 | 2.23 |
| 5-(4-(4-(4-methylpiperazin-1-yl)phenylamino)quinolin-6-yl)-2,3-dihydroinden-1-one | 449.1 | 2.16 |
| 2-methyl-4-(4-(4-(4-methylpiperazin-1-yl)phenylamino)quinolin-6-yl)benzonitrile | 434.3 | 2.34 |
| 6-(4-(difluoromethoxy)phenyl)-N-(4-(4-methylpiperazin-1-yl)phenyl)quinolin-4-amine | 461.1 | 2.44 |
| 6-(4-(diethylamino)phenyl)-N-(4-(4-methylpiperazin-1-yl)phenyl)quinolin-4-amine | 466.3 | 1.85 |
| 6-(1H-indol-6-yl)-N-(4-(4-methylpiperazin-1-yl)phenyl)quinolin-4-amine | 434.3 | 2.35 |
| 6-(4-chloro-3-methoxyphenyl)-N-(4-(4-methylpiperazin-1-yl)phenyl)quinolin-4-amine | 459.5 | 2.49 |
| 6-(4-chloro-3-fluorophenyl)-N-(4-(4-methylpiperazin-1-yl)phenyl)quinolin-4-amine | 447.1 | 2.52 |

| Compound | LC/MS m/z [M + H] | HPLC retention time (min) |
|---|---|---|
| 2-chloro-4-(4-(4-(4-methylpiperazin-1-yl)phenylamino)quinolin-6-yl)benzonitrile | 454.3 | 2.41 |
| 6-(benzo[d][1,3]dioxol-5-yl)-N-(4-(4-methylpiperazin-1-yl)phenyl)quinolin-4-amine | 439.5 | 2.31 |
| 6-(3-fluoro-4-methylphenyl)-N-(4-(4-methylpiperazin-1-yl)phenyl)quinolin-4-amine | 427.1 | 2.50 |
| 6-(3-chloro-4-methylphenyl)-N-(4-(4-methylpiperazin-1-yl)phenyl)quinolin-4-amine | 443.5 | 2.64 |
| 6-(3-fluoro-4-methoxyphenyl)-N-(4-(4-methylpiperazin-1-yl)phenyl)quinolin-4-amine | 443.5 | 2.35 |
| 6-(4-ethylphenyl)-N-(4-(4-methylpiperazin-1-yl)phenyl)quinolin-4-amine | 423.1 | 2.62 |
| 6-(4-chloro-3-methylphenyl)-N-(4-(4-methylpiperazin-1-yl)phenyl)quinolin-4-amine | 443.5 | 2.60 |
| 4-(4-(4-(3,3,3-trifluoropropyl)piperazin-1-yl)phenylamino)quinolin-6-yl)benzonitrile | 502.0 | 2.45 |
| 6-(3-chlorophenyl)-N-(4-(3-(dimethylamino)pyrrolidin-1-yl)phenyl)quinolin-4-amine | 443.5 | 2.56 |
| 6-(4-chlorophenyl)-N-(4-(3-(dimethylamino)pyrrolidin-1-yl)phenyl)quinolin-4-amine | 443.5 | 2.57 |
| N-(4-(3-(dimethylamino)pyrrolidin-1-yl)phenyl)-6-m-tolylquinolin-4-amine | 423.1 | 2.53 |
| N-(4-(3-(dimethylamino)pyrrolidin-1-yl)phenyl)-6-p-tolylquinolin-4-amine | 423.1 | 2.56 |
| N-(4-(3-(dimethylamino)pyrrolidin-1-yl)phenyl)-6-(3-methoxyphenyl)quinolin-4-amine | 439.5 | 2.43 |
| N-(4-(3-(dimethylamino)pyrrolidin-1-yl)phenyl)-6-(4-methoxyphenyl)quinolin-4-amine | 439.5 | 2.42 |
| N-(4-(3-(dimethylamino)pyrrolidin-1-yl)phenyl)-6-(4-fluoro-3-methylphenyl)quinolin-4-amine | 441.5 | 2.56 |
| 6-(3-(benzyloxy)phenyl)-N-(4-(3-(dimethylamino)pyrrolidin-1-yl)phenyl)quinolin-4-amine | 515.5 | 2.84 |
| N-(4-(3-(dimethylamino)pyrrolidin-1-yl)phenyl)-6-(4-vinylphenyl)quinolin-4-amine | 435.5 | 2.60 |
| 6-(3,4-dichlorophenyl)-N-(4-(3-(dimethylamino)pyrrolidin-1-yl)phenyl)quinolin-4-amine | 477.1 | 2.71 |
| N-(4-(3-(dimethylamino)pyrrolidin-1-yl)phenyl)-6-(3,4-dimethylphenyl)quinolin-4-amine | 437.1 | 2.64 |
| N-(4-(3-(dimethylamino)pyrrolidin-1-yl)phenyl)-6-(naphthalen-2-yl)quinolin-4-amine | 459.5 | 2.71 |
| N-(4-(3-(dimethylamino)pyrrolidin-1-yl)phenyl)-6-(4-isopropylphenyl)quinolin-4-amine | 451.1 | 2.81 |
| 6-(benzo[b]thiophen-3-yl)-N-(4-(3-(dimethylamino)pyrrolidin-1-yl)phenyl)quinolin-4-amine | 465.1 | 2.64 |
| N-(4-(3-(dimethylamino)pyrrolidin-1-yl)phenyl)-6-(5-methylpyridin-2-yl)quinolin-4-amine | 424.3 | 1.86 |
| N-(4-(3-(dimethylamino)pyrrolidin-1-yl)phenyl)-6-(1H-indol-5-yl)quinolin-4-amine | 448.3 | 2.39 |
| 6-(4-(3-(dimethylamino)pyrrolidin-1-yl)phenylamino)quinolin-6-yl)benzo[d]thiazol-2(3H)-one | 482.3 | 2.24 |
| 5-(4-(4-(3-(dimethylamino)pyrrolidin-1-yl)phenylamino)quinolin-6-yl)-2,3-dihydroinden-1-one | 463.5 | 2.27 |
| 5-(4-(4-(3-(dimethylamino)pyrrolidin-1-yl)phenylamino)quinolin-6-yl)nicotinic acid | 454.3 | 1.87 |
| 6-(6-chloropyridin-3-yl)-N-(4-(3-(dimethylamino)pyrrolidin-1-yl)phenyl)quinolin-4-amine | 444.3 | 2.24 |
| N-(4-(3-(dimethylamino)pyrrolidin-1-yl)phenyl)-6-(1H-indol-4-yl)quinolin-4-amine | 448.3 | 2.34 |
| 6-(6-chloro-5-methylpyridin-3-yl)-N-(4-(3-(dimethylamino)pyrrolidin-1-yl)phenyl)quinolin-4-amine | 458.3 | 2.38 |
| N-(4-(3-(dimethylamino)pyrrolidin-1-yl)phenyl)-6-(thiazol-2-yl)quinolin-4-amine | 416.3 | 2.08 |
| 1-(5-(4-(4-(3-(dimethylamino)pyrrolidin-1-yl)phenylamino)quinolin-6-yl)indolin-1-yl)ethanone | 492.3 | 2.31 |
| 4-(4-(4-(3-(dimethylamino)pyrrolidin-1-yl)phenylamino)quinolin-6-yl)-2-methylbenzonitrile | 448.3 | 2.41 |
| 6-(4-(difluoromethoxy)phenyl)-N-(4-(3-(dimethylamino)pyrrolidin-1-yl)phenyl)quinolin-4-amine | 475.1 | 2.54 |
| 6-(4-(diethylamino)phenyl)-N-(4-(3-(dimethylamino)pyrrolidin-1-yl)phenyl)quinolin-4-amine | 480.3 | 1.94 |
| N-(4-(3-(dimethylamino)pyrrolidin-1-yl)phenyl)-6-(1H-indol-6-yl)quinolin-4-amine | 448.3 | 2.44 |
| 4-(4-(4-(3-(dimethylamino)pyrrolidin-1-yl)phenylamino)quinolin-6-yl)-2-fluorobenzonitrile | 452.3 | 2.41 |
| 6-(4-chloro-3-methoxyphenyl)-N-(4-(3-(dimethylamino)pyrrolidin-1-yl)phenyl)quinolin-4-amine | 473.1 | 2.57 |
| 6-(4-chloro-3-fluorophenyl)-N-(4-(3-(dimethylamino)pyrrolidin-1-yl)phenyl)quinolin-4-amine | 461.1 | 2.63 |
| 6-(benzo[d][1,3]dioxol-5-yl)-N-(4-(3-(dimethylamino)pyrrolidin-1-yl)phenyl)quinolin-4-amine | 453.1 | 2.42 |
| N-(4-(3-(dimethylamino)pyrrolidin-1-yl)phenyl)-6-(3-fluoro-4-methylphenyl)quinolin-4-amine | 441.5 | 2.60 |
| 6-(3-chloro-4-methylphenyl)-N-(4-(3-(dimethylamino)pyrrolidin-1-yl)phenyl)quinolin-4-amine | 457.5 | 2.79 |
| N-(4-(3-(dimethylamino)pyrrolidin-1-yl)phenyl)-6-(3-fluoro-4-methoxyphenyl)quinolin-4-amine | 457.5 | 2.46 |
| 6-(4-chloro-3-methylphenyl)-N-(4-(3-(dimethylamino)pyrrolidin-1-yl)phenyl)quinolin-4-amine | 457.5 | 2.74 |
| 6-(4-chlorophenyl)-N-(4-(3-(diethylamino)pyrrolidin-1-yl)phenyl)quinolin-4-amine | 471.5 | 2.64 |
| 4-(4-(4-(3-(diethylamino)pyrrolidin-1-yl)phenylamino)quinolin-6-yl)benzonitrile | 462.3 | 2.39 |
| N-(4-(3-(diethylamino)pyrrolidin-1-yl)phenyl)-6-(naphthalen-2-yl)quinolin-4-amine | 487.5 | 2.77 |
| (R)-6-(4-chlorophenyl)-N-(4-(3-(dimethylamino)pyrrolidin-1-yl)phenyl)quinolin-4-amine | 443.5 | 2.58 |
| (R)-4-(4-(4-(3-(dimethylamino)pyrrolidin-1-yl)phenylamino)quinolin-6-yl)benzonitrile | 434.3 | 2.30 |
| (R)-N-(4-(3-(dimethylamino)pyrrolidin-1-yl)phenyl)-6-(naphthalen-2-yl)quinolin-4-amine | 459.5 | 2.69 |
| (S)-6-(4-chlorophenyl)-N-(4-(3-(dimethylamino)pyrrolidin-1-yl)phenyl)quinolin-4-amine | 443.5 | 2.57 |
| (S)-4-(4-(4-(3-(dimethylamino)pyrrolidin-1-yl)phenylamino)quinolin-6-yl)benzonitrile | 434.3 | 2.31 |
| (S)-N-(4-(3-(dimethylamino)pyrrolidin-1-yl)phenyl)-6-(naphthalen-2-yl)quinolin-4-amine | 459.5 | 2.68 |
| 4-(4-(4-(3-(benzyl(methyl)amino)pyrrolidin-1-yl)phenylamino)quinolin-6-yl)benzonitrile | 510.4 | 2.63 |
| 4-(4-(4-(3-(methyl(3,3,3-trifluoropropyl)amino)pyrrolidin-1-yl)phenylamino)quinolin-6-yl)benzonitrile | 516.4 | 2.57 |

Example 5

Synthesis of (109)

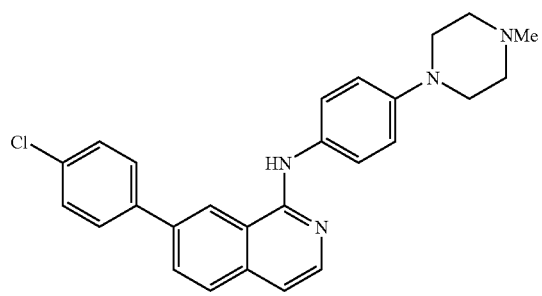

(109)

Step A: Synthesis of (110)

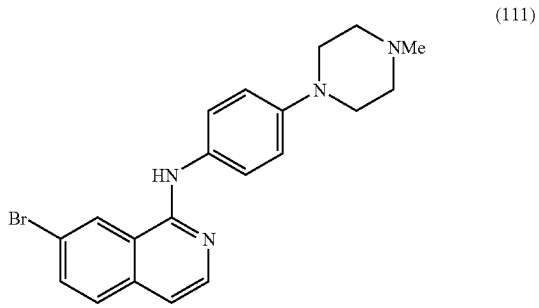

(110)

A mixture of 7-bromo-1-hydroxyisoquinoline (1 g, 4.47 mmol) and phosphorus oxychloride (20 mL) was heated at reflux for 20 min, cooled to room temperature, and concentrated in vacuo. The residue was treated with ice (100 g) and adjusted to pH 7 with 0.5M aqueous NaOH. The resulting mixture was extracted with EtOAc. The combined organic phases were washed with brine, dried over MgSO$_4$, and concentrated. The residue was crystallized from EtOAc/hexane to provide 110 (865 mg, 80%) as an off-white powder.

Step B: Synthesis of (111)

(111)

A solution of 110 (485 mg, 2 mmol) and sodium iodide (600 mg, 4 mmol) in sulfolane (4 mL) was irradiated in a microwave oven (max. power 250 W, 190° C.) for 5 min. To the cooled reaction mixture was added compound 104 from Example 2 (800 mg, 2.7 mmol) and N,N-diisopropylethylamine (500 µL, 2.9 mmol), and microwave heating was applied for an additional 10 min (max. power 250 W, 180° C.). The cooled reaction mixture was diluted with 0.5M aqueous HCl (15 mL) and resulting solution was subjected to HPLC purification (Method A). Fractions containing the desired product were combined and evaporated in vacuo. The resulting residue was lyophilized from water to provide 111 (437 mg, 35%) as a yellow amorphous solid as the trifluoroacetate salt.

Step C: Synthesis of (109)

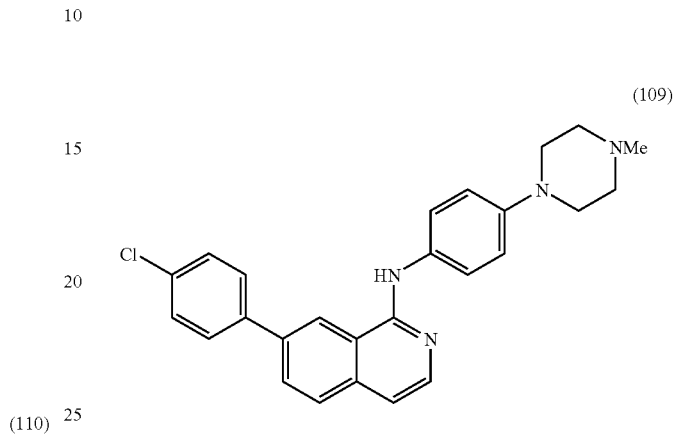

(109)

A mixture of 111 (3 mg, 0.008 mmol) and the 4-chlorophenylboronic acid (0.02 mmol) was dissolved in NMP (300 µL) followed by addition of cesium carbonate (10 mg, 0.31 mmol) and tetrakis(triphenylphosphine) palladium(0) (1 mg, 0.0006 mmol). The reaction mixture was irradiated in a microwave oven (max. power 250 W, 160° C.) for 5 min, cooled to room temperature, and concentrated in vacuo. The resulting residue was dissolved in DMSO (200 µL) and subjected to HPLC purification (Method B) to provide 1.1 mg (32%) the title compound as a yellow amorphous solid. LC/MS (ESI) m/z 429 [M+H]. HPLC retention time=2.12 min.

Example 6

The compounds listed below were prepared by the general procedures as set forth in the General Procedures and as exemplified in Example 5, utilizing the appropriate starting materials.

| Compound | LC/MS m/z [M + H] | HPLC retention time (min) |
|---|---|---|
| 7-(3-chlorophenyl)-N-(4-(4-methylpiperazin-1-yl)phenyl)isoquinolin-1-amine | 429.1 | 2.56 |
| 7-(2-methoxyphenyl)-N-(4-(4-methylpiperazin-1-yl)phenyl)isoquinolin-1-amine | 425.1 | 2.40 |
| 7-(3-methoxyphenyl)-N-(4-(4-methylpiperazin-1-yl)phenyl)isoquinolin-1-amine | 425.1 | 2.42 |
| 7-(4-methoxyphenyl)-N-(4-(4-methylpiperazin-1-yl)phenyl)isoquinolin-1-amine | 425.1 | 2.43 |
| 4-(1-(4-(4-propylpiperazin-1-yl)phenylamino)isoquinolin-7-yl)benzonitrile | 448.3 | 2.38 |
| 4-(1-(4-(4-(2-cyanoethyl)piperazin-1-yl)phenylamino)isoquinolin-7-yl)benzonitrile | 459.1 | 2.35 |
| 4-(1-(4-(4-(3-hydroxypropyl)piperazin-1-yl)phenylamino)isoquinolin-7-yl)benzonitrile | 464.3 | 2.31 |
| 4-(1-(4-(4-methylpiperazin-1-yl)phenylamino)isoquinolin-7-yl)benzonitrile | 420.3 | 2.31 |

Example 7

Synthesis of (112)

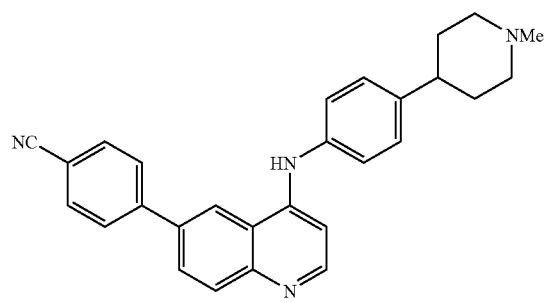

(112)

Step A: 1-methyl-4-phenylpiperidine (113)

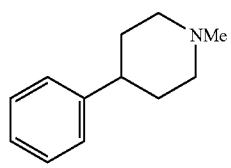

(113)

A solution of 4-phenylpiperidine (1.0 g, 6.2 mmol) was dissolved in THF (20 mL) and treated with formaldehyde (2.6 mL of a 37% solution in water). To the stirred reaction mixture was added sodium triacetoxyborohydride (2.63 g, 12.4 mmol). The reaction mixture was maintained at room temperature for 1 h, and then concentrated in vacuo. The residue was dissolved in dichloromethane, washed with 5% aqueous NaHCO$_3$ and brine, then dried over MgSO$_4$. Evaporation of the solvent yielded 1-methyl-4-phenylpiperidine 113 (1.06 g, 97%) as a colorless oil.

Step B: Synthesis of (114)

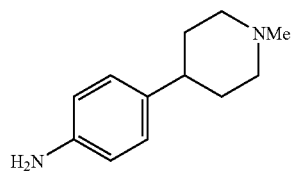

(114)

A solution of 113 in concentrated sulfuric acid (5 mL) was cooled in an ice bath, and a solution of fuming nitric acid (225 μL, 5 mmol) in concentrated sulfuric acid (3 mL) was added dropwise over 30 min. The reaction mixture was stirred at 0° C. for 3 h, then at room temperature for 1.5 h. The reaction mixture was poured over ice (50 g), basified with solid NaOH (15 g), and extracted with dichloromethane. The organic layer was washed with water and brine and dried over MgSO$_4$. Evaporation of the solvent provided a residue that was purified by preparative HPLC (Method A) to provide 114 as a yellow oil.

A mixture of 113 and 5% palladium on carbon (500 mg) in MeOH (50 mL) was hydrogenated at 80 psi for 20 min, then filtered. Evaporation of the solvent provided 114 (272 mg, 23%) as a clear oil.

Step C: Synthesis of (112)

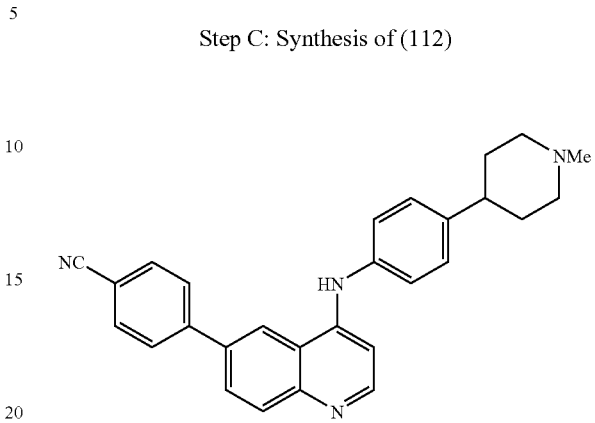

A mixture of 114 (3.8 mg, 0.02 mmol) and compound 106 from Example 2 (10.6 mg, 0.04 mmol) was dissolved in DMSO (250 μL), followed by addition of N,N-diisopropylethylamine (17 μL, 0.1 mmol). The reaction mixture was irradiated in a microwave oven (max. power 250 W, 180° C.) for 5 min, cooled to room temperature, and subjected to HPLC purification (Method B) to provide the title compound (1.4 mg, 17%) as a yellow amorphous solid. LC/MS (ESI) m/z 419 [M+H]. HPLC retention time=2.41 min.

Example 8

Synthesis of (115)

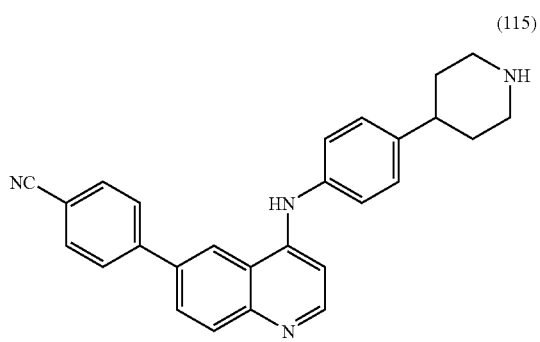

(115)

Step A: Synthesis of (116)

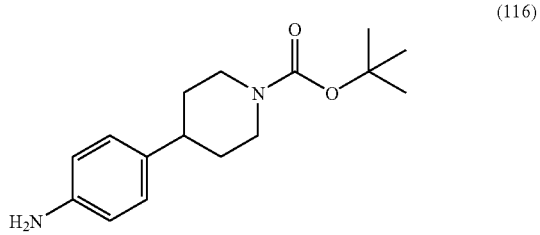

(116)

A solution of 4-phenylpiperidine (500 mg, 3.1 mmol) in concentrated sulfuric acid (3 mL) was cooled in an ice bath, and a solution of fuming nitric acid (140 μL, 5 mmol) in concentrated sulfuric acid (3 mL) was added dropwise over 20 min. The reaction mixture was stirred at 0° C. for 3 h then at room temperature for 1.5 h. The reaction mixture was poured over ice (30 g), basified with solid NaOH (8 g), and extracted with dichloromethane. The organic layer was separated and di-tert-butyl dicarbonate (653 mg, 3 mmol) was added. The reaction mixture was stirred at room temperature for 2 h. Evaporation of the solvent provided a residue that was purified by preparative HPLC (Method A) to provide 116 as a colorless oil.

A mixture of 116 and 5% palladium on carbon (500 mg) in MeOH (50 mL) was hydrogenated at 80 psi for 20 min, then filtered. Evaporation of the solvent provided 116 (228 mg, 33%) as a clear oil.

Step B: Synthesis of (117)

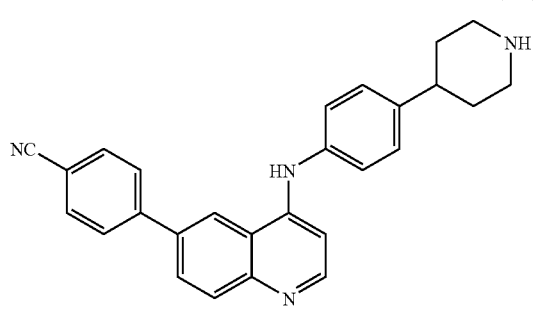

(117)

A mixture of 116 (5.5 mg, 0.02 mmol) and compound 106 from Example 2 (10.6 mg, 0.04 mmol) was dissolved in DMSO (250 μL), followed by addition of N,N-diisopropylethylamine (17 μL, 0.1 mmol). The reaction mixture was irradiated in a microwave oven (max. power 250 W, 180° C.) for 5 min, cooled to room temperature. Solvents were evaporated and the residue treated with 60% TFA in dichloromethane at room temperature for 30 min. Solvents were evaporated. The resulting residue was dissolved in DMSO (200 μL) and subjected to HPLC purification (Method B) to provide the title compound (1.6 mg, 20%) as a yellow amorphous solid. LC/MS (ESI) m/z 405 [M+H]. HPLC retention time=1.86 min.

Example 9

The compounds listed below were prepared by the general procedures as set forth above, utilizing the appropriate starting materials.

| Compound | LC/MS m/z [M + H] | HPLC retention time (min) |
| --- | --- | --- |
| 6-(4-chlorophenyl)-4-(4-(4-methylpiperazin-1-yl)phenoxy)quinoline | 430.3 | 2.47 |
| 4-(4-(4-(4-methylpiperazin-1-yl)phenoxy)quinolin-6-yl)benzonitrile | 421.1 | 2.17 |

Example 10

Characterization of Compounds

The following HPLC conditions were used for characterizing compounds of the present disclosure: Phenomenex Chromolith SpeedRod RP-18e C18 analytical column (4.6 mm×50 mm); flow rate=1.5 mL/min; injection volume=10-15 μL; mobile phase A: 100% water, 0.1% trifluoroacetic acid (TFA); mobile phase B: 100% acetonitrile, 0.1% trifluoroacetic acid (TFA); gradient elution from 5% B to 100% B over about 4.4 min, with a stay at 100% B for 1 min, then equilibration to 5% B over about 0.6 min. MS ions were detected using a Sciex API-100 electrospray single quadrupole mass spectrometer interfaced to the HPLC system.

The following HPLC methods were used for purifying compounds of the present disclosure:

Method A: YMC-Pack ODS-A C-18 column (30 mm×100 mm); flow rate=36 or 45 mL/min; injection volume=2-10 mL; mobile phase A: 100% water, 0.1% trifluoroacetic acid (TFA); mobile phase B: 100% acetonitrile, 0.1% TFA; gradient elution from 0% B to 100% B or from 0% B to 60% B over 60 min.

Method B: Phenomenex Synergi 4 μm Max-RP column (10 mm×50 mm) or Thermo Beta Basic 5 μm C-18 column (10 mm×50 mm); flow rate=6 mL/min; injection volume=100 μL; mobile phase A: 100% water, 0.1% trifluoroacetic acid (TFA); mobile phase B: 100% acetonitrile, 0.1% trifluoroacetic acid (TFA); gradient elution from 5% B to 100% B or 10% B to 100% B over 6 min.

Example 11

HTS ATP-Utilizing Enzyme Assays

The following procedures describe the reagent and plate preparation for a HTS of an ATP-utilizing enzyme, such as a protein kinase, run in an off-chip mobility-shift assay format. The following provides an HTS protocol for running a protein kinase HTS screen on a Caliper HTS 250 microfluidics system. The following parameters are dependent on the protein kinase used and can be determined by one skilled in the art as part of a typical assay development process. For example, the peptide substrate used can be identified from the current literature, by screening a peptide library of potential protein kinase substrates, or by other applicable means accepted in the field.

The following table provides typical screen assay parameters appropriate for a Caliper HTS 250 microfluidics system.

| Reaction Concentration | | |
| --- | --- | --- |
| Inhibitor concentration | 10 | μM |
| Enzyme concentration | 0.25 | nM |
| Substrate/Peptide Conc. | 1 | μM |
| ATP | 20 | μM |
| Reaction Properties | | |
| Inhibitor Volume | 5 | μL |
| Enzyme Volume | 10 | μL |
| Substrate Volume | 10 | μL |
| Termination Volume | 45 | μL |
| Reaction Time | 3 | hr |
| Reaction Temperature | 20-25 | ° C. |

-continued

| Sipper Properties | | |
| --- | --- | --- |
| Initial Delay | 18 | sec |
| Buffer | 18 | sec |
| Sample | 0.2 | sec |
| Final Delay | 120 | sec |
| Dye Well | | |
| Dye | 0.2 | sec |
| Script Properties | | |
| Electrode 1 | −250 | Volts |
| Electrode 2 | −2250 | Volts |
| Electrode 3 | −2250 | Volts |
| Electrode 4 | −250 | Volts |
| Laser Properties | yes/no | |
| UV | no | |
| Blue | yes | |
| Red | no | |
| Data Collection | yes/no | |
| CCD1 | no | |
| CCD2 | yes | |
| CCD3 | no | |
| Inhibitor Concentrations | | |
| Inhibitor: EDTA 100% | 20 | mM |
| Inhibitor Staurosporine 50% | 185.8 | nM |
| Pressure Driven Flow | | |
| Pressure | −2 | psi |
| Base Pressure | −2 | psi |

The reagents and buffers listed in the following table are generally applicable for developing and running an HTS screen on a human protein kinase using the Caliper HTS 250 system.

| Reagent | Reagent Name | Manufacturer | Catalog # | MW | Storage |
| --- | --- | --- | --- | --- | --- |
| 4 sipper LABCHIP | FS266 | Caliper Tech. Inc. | 760077-0266 | — | 2-8° C. |
| Enzyme | Specific enzyme | — | — | — | −20° C. |
| Substrate | Specific substrate 3 | BioPeptide | — | 1528 Da | −20° C. |
| Control Inhibitor | Staurosporine | Calbiochem | 56397 | 466.5 | 20° C. |
| Buffer Components | HEPES (free acid) | Calbiochem | 391338 | 238.3 | RT |
| | HEPES (Na Salt) | Calbiochem | 391333 | 260.3 | RT |
| | DMSO | Sigma | D8418 | — | RT |
| | Triton X-100 | Sigma | T8787 | — | RT |
| | BSA | Sigma | A8806 | — | 2-8° C. |
| | DTT (Cleland's Reagent) | Calbiochem | 233153 | 154.2 | 2-8° C. |
| | EDTA (0.5M) | Sigma | E7889 | n/a | RT |
| | Coating Reagent 3 | Caliper Tech. Inc. | 760050 | n/a | 2-8° C. |
| | 6 N HCl | VWR | JT5619-2 | n/a | RT |
| | ATP disodium salt | Sigma | A7699 | 551.1 | −20° C. |
| | $Na_3VO_4$ | Calbiochem | 567540 | 183.9 | −20° C. |
| | β-Glycerophosphate | Calbiochem | 35675 | 306.1 | −20° C. |
| | $MgCl_2 \cdot 6H_2O$ | Sigma | M2670 | 203.3 | RT |

The following reagents were prepared using the previously described buffers.

A 2× Master Buffer solution was prepared by combining 200 mL of 1 M HEPES, pH 7.5, 2 mL of 10% Triton X-100, 20 mL of 10% BSA, and 778 mL of $H_2O$.

A 2.5× Enzyme Buffer solution was prepared by combining 177.408 mL of 2× Master Buffer, 0.887 mL of 1 M DTT, 0.089 mL of 100 mM ATP, 8.870 mL of 1 M $MgCl_2$, 0.089 mL of 100 mM β-glycerophosphate, 0.089 mL of 100 mM $Na_3VO_4$, 0.254 mL of 62.8 µM enzyme, and 167.13 mL $H_2O$.

A 2.5× Substrate Buffer solution was prepared by combining 177.408 mL of 2× Master Buffer, 0.887 mL of 1 mM peptide-X, and 176.521 mL of $H_2O$.

A 1.55× Termination Buffer solution was prepared by combining 762.05 mL of 2× Master Buffer, 95.1 mL of 0.5 M EDTA, and 666.94 mL of $H_2O$.

A TCB Buffer solution was prepared by combining 125 mL of 2× Master Buffer, 10 mL of 0.5 M EDTA, 6.25 mL of 4% coating reagent, 1.01 mL of 100% DMSO, and 107.74 mL $H_2O$.

A Dye Trough solution was prepared by combining 0.5 µL of peptide-X, and 2,999.5 µL of IX Master Buffer.

A 1.06× Assay Buffer solution was prepared by combining 205.15 mL of 2× Master Buffer, and 181.92 mL of $H_2O$.

Assays to determine the kinase inhibitory activity of compounds of the present disclosure were performed using a Caliper HTS 250 microfluidics device, Greiner U-bottom assay plates, a Multidrop for transfer of reagents, and Biomek FX (AMNCBM03) software. Initially, 2.4 µL of a 1 mM solution of a test compound in 100% DMSO was added to a well of the Greiner U-bottom plate. A single Greiner U-bottom plate having 24×16 wells could include multiple test compounds. Next, 40 µL of 1.06× Assay Buffer was added to each well of the assay plate. Using the Biomek FX, 10 µL of 0.5 M EDTA was added by the span-8 to wells, indicated as 100% Control and 2.4 µL of 100% DMSO was added by the span-8 to wells, indicated as 0% Control. Using the Multidrop, 10 µL of 2.5× Enzyme Buffer, followed by 10 µL of 2.5× Substrate Buffer was added to each well of the assay plate.

The total reaction volume in each well was 25 µL, and the concentration of the test compound was 10 µM. The assay plate was incubated for 2.5 hrs at 20° C. to 22° C. After the incubation period, using the Multidrop, 45 µL of 1.55× Termination Buffer was added to each well of the assay plate to stop the reaction. The inhibition of the ATP-utilizing enzyme, such as a particular protein kinase, was determined by measuring the ratio of the peptide substrate to phosphorylated product for each well of the assay plate using the Caliper HTS 250 system.

Compounds exhibiting an activity for a particular target ATP-utilizing enzyme greater than six-sigma from the mean activity for the population of predominately inactive compounds for the same target ATP-utilizing enzyme were considered to be active. The use of six-sigma statistical limits represents a conservative method for declaring potential hits among targets. The six-sigma activity, as well as the mean population activity, can be different for each target enzyme. This method has an expected false positive rate, from an in-control measurement process, of one in one million. Compounds were considered to show selectivity between a primary target and one or more other targets if the activity (e.g. % inhibition, $IC_{50}$, $K_i$, $EC_{50}$, etc.) for that compound against the primary target was significantly different than that for the other target(s) within the error of the activity measurement.

Certain compounds of Formula 1 which exhibit protein kinase inhibitory activity are provided below:

TABLE 1

| Compound Name | Activity |
| --- | --- |
| N-(4-(4-methylpiperazin-1-yl)phenyl)-6-phenylquinolin-4-amine | MAPKAPK2 |
| | PRAK |
| | P38-δ |
| 6-(3-chlorophenyl)-N-(4-(4-methylpiperazin-1-yl)phenyl)quinolin-4-amine | MAPKAPK2 |
| | PRAK |
| | NEK2 |
| 6-(4-chlorophenyl)-N-(4-(4-methylpiperazin-1-yl)phenyl)quinolin-4-amine | MAPKAPK2 |
| | PRAK |
| N-(4-(4-methylpiperazin-1-yl)phenyl)-6-o-tolylquinolin-4-amine | MAPKAPK2 |
| | PRAK |
| | DYRK2 |
| | NEK2 |
| | BMX |
| N-(4-(4-methylpiperazin-1-yl)phenyl)-6-m-tolylquinolin-4-amine | MAPKAPK2 |
| | PRAK |
| | NEK2 |
| N-(4-(4-methylpiperazin-1-yl)phenyl)-6-p-tolylquinolin-4-amine | MAPKAPK2 |
| | PRAK |
| | NEK2 |
| 6-(2-methoxyphenyl)-N-(4-(4-methylpiperazin-1-yl)phenyl)quinolin-4 amine | MAPKAPK2 |
| | PRAK |
| | P38-δ |
| | NEK2 |
| 6-(3-methoxyphenyl)-N-(4-(4-methylpiperazin-1-yl)phenyl)quinolin-4-amine | MAPKAPK2 |
| | PRAK |
| | DYRK2 |
| | NEK2 |
| 6-(4-methoxyphenyl)-N-(4-(4-methylpiperazin-1-yl)phenyl)quinolin-4-amine | MAPKAPK2 |
| | PRAK |
| | p38-δ |
| | DYRK2 |
| | NEK2 |
| 2-(4-(4-(4-methylpiperazin-1-yl)phenylamino)quinolin-6-yl)benzamide | MAPKAPK2 |
| 3-(4-(4-(4-methylpiperazin-1-yl)phenylamino)quinolin-6-yl)benzonitrile | AKT3 |
| | PRAK |
| | MAPKAPK2 |
| | AKT1 |
| | NEK2 |
| 4-(4-(4-(4-methylpiperazin-1-yl)phenylamino)quinolin-6-yl)benzonitrile | MAPKAPK2 |
| | PRAK |
| | NEK2 |
| 6-(3,4-dimethoxyphenyl)-N-(4-(4-methylpiperazin-1-yl)phenyl)quinolin-4-amine | MAPKAPK2 |
| | PRAK |
| | DYRK2 |
| | NEK2 |
| 6-(2,4-difluorophenyl)-N-(4-(4-methylpiperazin-1-yl)phenyl)quinolin-4-amine | MAPKAPK2 |
| | PRAK |
| | P70S6K1 |
| | NEK2 |
| 6-(4-fluoro-3-methylphenyl)-N-(4-(4-methylpiperazin-1-yl)phenyl)quinolin-4-amine | MAPKAPK2 |
| | PRAK |
| | P70S6K1 |
| | C-TAK1 |
| | NEK2 |
| (3-(4-(4-(4-methylpiperazin-1-yl)phenylamino)quinolin-6-yl)phenyl)methanol | PRAK |
| | MAPKAPK2 |
| | FLT3 |

TABLE 1-continued

| Compound Name | Activity |
|---|---|
| | P70S6K1 |
| | CHEK2 |
| 6-(5-fluoro-2-methoxyphenyl)-N-(4-(4-methylpiperazin-1-yl)phenyl)quinolin-4-amine | MAPKAPK2 |
| | PRAK |
| | P38-δ |
| 3-(4-(4-(4-methylpiperazin-1-yl)phenylamino)quinolin-6-yl)phenol | MAPKAPK2 |
| | PRAK |
| | SRC |
| | ABL1 |
| | P70S6K1 |
| | AKT3 |
| | LCK |
| 6-(3-chloro-4-fluorophenyl)-N-(4-(4-methylpiperazin-1-yl)phenyl)quinolin-4-amine | MAPKAPK2 |
| | PRAK |
| | P70S6K1 |
| | C-TAK1 |
| | NEK2 |
| | MSK1 |
| 4-(4-(4-(4-methylpiperazin-1-yl)phenylamino)quinolin-6-yl)phenol | DYRK2 |
| | FLT-3 |
| | PRAK |
| | MAPKAPK2 |
| | ROCK2 |
| 6-(2,3-dimethylphenyl)-N-(4-(4-methylpiperazin-1-yl)phenyl)quinolin-4-amine | MAPKAPK2 |
| | PRAK |
| | NEK2 |
| 6-(2,5-dimethoxyphenyl)-N-(4-(4-methylpiperazin-1-yl)phenyl)quinolin-4-amine | MAPKAPK2 |
| | PRAK |
| 6-(2-ethylphenyl)-N-(4-(4-methylpiperazin-1-yl)phenyl)quinolin-4-amine | MAPKAPK2 |
| | PRAK |
| | NEK2 |
| 4-(4-(4-(4-methylpiperazin-1-yl)phenylamino)quinolin-6-yl)benzamide | MAPKAPK2 |
| | PRAK |
| | ROCK2 |
| | DYRK2 |
| | NEK2 |
| 6-(4-(ethylthio)phenyl)-N-(4-(4-methylpiperazin-1-yl)phenyl)quinolin-4-amine | MAPKAPK2 |
| | PRAK |
| | P70S6K1 |
| | C-TAK1 |
| | NEK2 |
| 6-(3,5-difluorophenyl)-N-(4-(4-methylpiperazin-1-yl)phenyl)quinolin-4-amine | MAPKAPK2 |
| | PRAK |
| 6-(biphenyl-2-yl)-N-(4-(4-methylpiperazin-1-yl)phenyl)quinolin-4-amine | LCK |
| | ABL |
| | LYNA |
| | NEK2 |
| | PRAK |
| 6-(2,5-difluorophenyl)-N-(4-(4-methylpiperazin-1-yl)phenyl)quinolin-4-amine | MAPKAPK2 |
| | PRAK |
| | P70S6K1 |
| | P38-δ |
| | NEK2 |
| 6-(4-fluorophenyl)-N-(4-(4-methylpiperazin-1-yl)phenyl)quinolin-4-amine | MAPKAPK2 |
| | PRAK |
| | DYRK2 |
| | P70S6K1 |
| | C-TAK1 |
| | GSK3-α |
| | NEK2 |
| 6-(2,3-dichlorophenyl)-N-(4-(4-methylpiperazin-1-yl)phenyl)quinolin-4-amine | MAPKAPK2 |
| | C-TAK1 |
| | PRAK |
| | LYNA |
| | P70S6K1 |
| 6-(2,5-dimethylphenyl)-N-(4-(4-methylpiperazin-1-yl)phenyl)quinolin-4-amine | MAPKAPK2 |
| | PRAK |
| | AKT3 |
| | NEK2 |
| 3-(4-(4-(4-methylpiperazin-1-yl)phenylamino)quinolin-6-yl)benzoic acid | CK2 |
| | PRAK |
| | MAPKAPK2 |
| N-(4-(4-methylpiperazin-1-yl)phenyl)-6-(4-(methylthio)phenyl)quinolin-4-amine | MAPKAPK2 |
| | PRAK |
| 6-(3-ethoxyphenyl)-N-(4-(4-methylpiperazin-1-yl)phenyl)quinolin-4-amine | PARK |
| | MAPKAPK2 |
| | P70S6K1 |

TABLE 1-continued

| Compound Name | Activity |
|---|---|
| N-(4-(4-methylpiperazin-1-yl)phenyl)-6-(2-(trifluoromethyl)phenyl)quinolin-4-amine | CHEK2<br>NEK2<br>P38-δ<br>MAPKAPK2<br>PRAK<br>CK2 |
| 6-(3-(benzyloxy)phenyl)-N-(4-(4-methylpiperazin-1-yl)phenyl)quinolin-4-amine | NEK2<br>PRAK<br>MAPKAPK2<br>C-TAK1<br>CDK2/cyclin A |
| N-(4-(4-methylpiperazin-1-yl)phenyl)-6-(4-vinylphenyl)quinolin-4-amine | CHEK2<br>MAPKAPK2<br>PRAK<br>NEK2 |
| 6-(2,4-dimethoxyphenyl)-N-(4-(4-methylpiperazin-1-yl)phenyl)quinolin-4-amine | CHEK2<br>MAPKAPK2<br>PRAK<br>NEK2 |
| N-(4-(4-methylpiperazin-1-yl)phenyl)-6-(3,4,5-trifluorophenyl)quinolin-4-amine | MAPKAPK2<br>PRAK<br>CHEK1<br>NEK2 |
| (4-(4-(4-methylpiperazin-1-yl)phenylamino)quinolin-6-yl)phenyl)methanol | MAPKAPK2<br>PRAK |
| N-(4-(4-methylpiperazin-1-yl)phenyl)-6-(4-phenoxyphenyl)quinolin-4-amine | PRAK<br>C-TAK1<br>MAPKAPK2 |
| 6-(4-ethoxyphenyl)-N-(4-(4-methylpiperazin-1-yl)phenyl)quinolin-4-amine | MAPKAPK2<br>PRAK |
| 6-(3,4-dichlorophenyl)-N-(4-(4-methylpiperazin-1-yl)phenyl)quinolin-4-amine | MAPKAPK2<br>PRAK<br>C-TAK1<br>CDK2/cyclin A<br>CHEK2<br>NEK2 |
| N-(4-(4-methylpiperazin-1-yl)phenyl)-6-(4-(trifluoromethyl)phenyl)quinolin-4-amine | MAPKAPK2<br>PRAK<br>CHEK1<br>P70S6K1<br>NEK2<br>C-TAK1 |
| 6-(2,5-dichlorophenyl)-N-(4-(4-methylpiperazin-1-yl)phenyl)quinolin-4-amine | MAPKAPK2 |
| 6-(2,4-dichlorophenyl)-N-(4-(4-methylpiperazin-1-yl)phenyl)quinolin-4-amine | MAPKAPK2<br>PRAK<br>NEK2 |
| 6-(3-isopropylphenyl)-N-(4-(4-methylpiperazin-1-yl)phenyl)quinolin-4-amine | MAPKAPK2<br>PRAK |
| 6-(4-isopropylphenyl)-N-(4-(4-methylpiperazin-1-yl)phenyl)quinolin-4-amine | MAPKAPK2<br>PRAK<br>NEK2 |
| 6-(4-fluoro-2-methylphenyl)-N-(4-(4-methylpiperazin-1-yl)phenyl)quinolin-4-amine | MAPKAPK2<br>PRAK |
| 6-(3,4-difluorophenyl)-N-(4-(4-methylpiperazin-1-yl)phenyl)quinolin-4-amine | MAPKAPK2<br>PRAK |
| 6-(biphenyl-3-yl)-N-(4-(4-methylpiperazin-1-yl)phenyl)quinolin-4-amine | MAPKAPK2<br>PRAK<br>P38-β<br>C-TAK1 |
| 6-(5-isopropyl-2-methoxyphenyl)-N-(4-(4-methylpiperazin-1-yl)phenyl)quinolin-4-amine | MAPKAPK2<br>PRAK |
| N-(3-(4-(4-methylpiperazin-1-yl)phenylamino)quinolin-6-yl)phenyl)acetamide | MAPKAPK2<br>PRAK<br>GSK3-α |
| 6-(2,4-bis(trifluoromethyl)phenyl)-N-(4-(4-methylpiperazin-1-yl)phenyl)quinolin-4-amine | MAPKAPK2 |
| N-(4-(4-methylpiperazin-1-yl)phenyl)-6-(4-(methylsulfinyl)phenyl)quinolin-4-amine | MAPKAPK2<br>PRAK |
| N-(4-(4-methylpiperazin-1-yl)phenyl)-6-(4-pentylphenyl)quinolin-4-amine | PRAK<br>C-TAK1 |
| 6-(3,5-bis(trifluoromethyl)phenyl)-N-(4-(4-methylpiperazin-1-yl)phenyl)quinolin-4-amine | MAPKAPK2 |
| 6-(4-butylphenyl)-N-(4-(4-methylpiperazin-1-yl)phenyl)quinolin-4-amine | MAPKAPK2<br>PRAK |
| 3-(4-(4-(4-methylpiperazin-1-yl)phenylamino)quinolin-6-yl)phenyl)propanoic acid | MAPKAPK2 |

TABLE 1-continued

| Compound Name | Activity |
|---|---|
| N-(4-(4-methylpiperazin-1-yl)phenyl)-6-(3-nitrophenyl)quinolin-4-amine | MAPKAPK2<br>PRAK<br>AKT3 |
| 6-(3-fluorophenyl)-N-(4-(4-methylpiperazin-1-yl)phenyl)quinolin-4-amine | MAPKAPK2<br>PRAK |
| 6-(2-fluorophenyl)-N-(4-(4-methylpiperazin-1-yl)phenyl)quinolin-4-amine | MAPKAPK2<br>PRAK |
| 6-(4-tert-butylphenyl)-N-(4-(4-methylpiperazin-1-yl)phenyl)quinolin-4-amine | MAPKAPK2<br>CHEK1<br>C-TAK1<br>P70S6K1<br>PRAK<br>NEK2 |
| N-(4-(4-methylpiperazin-1-yl)phenyl)-6-(3-(trifluoromethoxy)phenyl)quinolin-4-amine | MAPKAPK2<br>PRAK |
| N-(4-(4-methylpiperazin-1-yl)phenyl)-6-(4-(trifluoromethoxy)phenyl)quinolin-4-amine | MAPKAPK2<br>PRAK<br>P70S6K1 |
| 6-(2,6-difluorophenyl)-N-(4-(4-methylpiperazin-1-yl)phenyl)quinolin-4-amine | MAPKAPK2<br>PRAK |
| N-(4-(4-methylpiperazin-1-yl)phenyl)-6-(3-(trifluoromethyl)phenyl)quinolin-4-amine | MAPKAPK2<br>PRAK |
| 6-(4-(benzyloxy)phenyl)-N-(4-(4-methylpiperazin-1-yl)phenyl)quinolin-4-amine | C-TAK1<br>SRC<br>BMX |
| 6-(2-((dimethylamino)methyl)phenyl)-N-(4-(4-methylpiperazin-1-yl)phenyl)quinolin-4-amine | MAPKAPK2 |
| 6-(4-(benzyloxy)-3-fluorophenyl)-N-(4-(4-methylpiperazin-1-yl)phenyl)quinolin-4-amine | C-TAK1<br>MAPKAPK2<br>SRC<br>SYK |
| 6-(4-cyclohexylphenyl)-N-(4-(4-methylpiperazin-1-yl)phenyl)quinolin-4-amine | C-TAK1<br>MAPKAPK2 |
| 6-(3,4-dimethylphenyl)-N-(4-(4-methylpiperazin-1-yl)phenyl)quinolin-4-amine | MAPKAPK2<br>PRAK<br>NEK2 |
| 6-phenyl-N-(4-(piperazin-1-yl)phenyl)quinolin-4-amine | PRAK<br>FLT-3<br>MAPKAPK2<br>PDGFR-α<br>P38-δ<br>LYNA<br>KIT<br>CHEK1 |
| N-(4-(4-ethylpiperazin-1-yl)phenyl)-6-phenylquinolin-4-amine | PRAK<br>MAPKAPK2 |
| 6-phenyl-N-(4-(4-propylpiperazin-1-yl)phenyl)quinolin-4-amine | MAPKAPK2<br>PRAK |
| N-(4-(4-butylpiperazin-1-yl)phenyl)-6-phenylquinolin-4-amine | MAPKAPK2 |
| N-(4-(4-isopropylpiperazin-1-yl)phenyl)-6-phenylquinolin-4-amine | MAPKAPK2<br>KIT |
| N-(4-(4-(pentan-3-yl)piperazin-1-yl)phenyl)-6-phenylquinolin-4-amine | MAPKAPK2 |
| 2-(4-(4-(6-phenylquinolin-4-ylamino)phenyl)piperazin-1-yl)ethanol | MAPKAPK2 |
| N-(4-(4-(2-methoxyethyl)piperazin-1-yl)phenyl)-6-phenylquinolin-4-amine | MAPKAPK2 |
| 3-(4-(4-(6-phenylquinolin-4-ylamino)phenyl)piperazin-1-yl)propan-1-ol | MAPKAPK2<br>PRAK |
| N-(4-(4-(2-(dimethylamino)ethyl)piperazin-1-yl)phenyl)-6-phenylquinolin-4-amine | MAPKAPK2 |
| 3-(4-(4-(6-phenylquinolin-4-ylamino)phenyl)piperazin-1-yl)propanenitrile | MAPKAPK2<br>PRAK |
| 2-(4-(4-(6-phenylquinolin-4-ylamino)phenyl)piperazin-1-yl)acetic acid | PDGFR-α<br>FLT-3<br>MAPKAPK2 |
| 6-(4-methoxyphenyl)-N-(4-(piperazin-1-yl)phenyl)quinolin-4-amine | MAPKAPK2<br>PRAK<br>P38-δ<br>DYRK2<br>CDK1/cyclin B<br>FLT-3<br>CHEK1<br>KIT |
| N-(4-(4-ethylpiperazin-1-yl)phenyl)-6-(4-methoxyphenyl)quinolin-4-amine | MAPKAPK2 |
| 6-(4-methoxyphenyl)-N-(4-(4-propylpiperazin-1-yl)phenyl)quinolin-4-amine | MAPKAPK2 |

TABLE 1-continued

| Compound Name | Activity |
|---|---|
| N-(4-(4-butylpiperazin-1-yl)phenyl)-6-(4-methoxyphenyl)quinolin-4-amine | MAPKAPK2 |
| N-(4-(4-isopropylpiperazin-1-yl)phenyl)-6-(4-methoxyphenyl)quinolin-4-amine | MAPKAPK2 BMX |
| 2-(4-(4-(6-(4-methoxyphenyl)quinolin-4-ylamino)phenyl)piperazin-1-yl)ethanol | MAPKAPK2 |
| 3-(4-(4-(6-(4-methoxyphenyl)quinolin-4-ylamino)phenyl)piperazin-1-yl)propan-1-ol | MAPKAPK2 DYRK2 P38-δ |
| N-(4-(4-(2-(dimethylamino)ethyl)piperazin-1-yl)phenyl)-6-(4-methoxyphenyl)quinolin-4-amine | MAPKAPK2 C-TAK1 DYRK2 |
| 3-(4-(4-(6-(4-methoxyphenyl)quinolin-4-ylamino)phenyl)piperazin-1-yl)propanenitrile | MAPKAPK2 |
| 2-(4-(4-(6-(4-methoxyphenyl)quinolin-4-ylamino)phenyl)piperazin-1-yl)-N,N-dimethylacetamide | MAPKAPK2 |
| 2-(4-(4-(6-(4-methoxyphenyl)quinolin-4-ylamino)phenyl)piperazin-1-yl)acetic acid | MAPKAPK2 PDGFR-α |
| 4-(4-(piperazin-1-yl)phenylamino)quinolin-6-yl)benzonitrile | MAPKAPK2 PRAK P38-α |
| 4-(4-(4-ethylpiperazin-1-yl)phenylamino)quinolin-6-yl)benzonitrile | MAPKAPK2 PRAK |
| 4-(4-(4-propylpiperazin-1-yl)phenylamino)quinolin-6-yl)benzonitrile | MAPKAPK2 PRAK |
| 4-(4-(4-butylpiperazin-1-yl)phenylamino)quinolin-6-yl)benzonitrile | MAPKAPK2 |
| 4-(4-(4-sec-butylpiperazin-1-yl)phenylamino)quinolin-6-yl)benzonitrile | MAPKAPK2 BMX |
| 4-(4-(4-(pentan-3-yl)piperazin-1-yl)phenylamino)quinolin-6-yl)benzonitrile | MAPKAPK2 |
| 4-(4-(4-allylpiperazin-1-yl)phenylamino)quinolin-6-yl)benzonitrile | MAPKAPK2 |
| 4-(4-(4-cyclohexylpiperazin-1-yl)phenylamino)quinolin-6-yl)benzonitrile | MAPKAPK2 |
| 4-(4-(4-(2-hydroxyethyl)piperazin-1-yl)phenylamino)quinolin-6-yl)benzonitrile | MAPKAPK2 |
| 4-(4-(4-(3-hydroxypropyl)piperazin-1-yl)phenylamino)quinolin-6-yl)benzonitrile | MAPKAPK2 |
| 4-(4-(4-(2-(dimethylamino)ethyl)piperazin-1-yl)phenylamino)quinolin-6-yl)benzonitrile | C-TAK1 MAPKAPK2 CHEK1 |
| 4-(4-(4-(2-cyanoethyl)piperazin-1-yl)phenylamino)quinolin-6-yl)benzonitrile | MAPKAPK2 PRAK |
| 2-(4-(4-(6-(4-cyanophenyl)quinolin-4-ylamino)phenyl)piperazin-1-yl)acetic acid | MAPKAPK2 PRAK |
| N-(4-(4-sec-butylpiperazin-1-yl)phenyl)-6-phenylquinolin-4-amine | MAPKAPK2 |
| N-(4-(4-cyclopentylpiperazin-1-yl)phenyl)-6-phenylquinolin-4-amine | MAPKAPK2 |
| N-(4-(4-cyclohexylpiperazin-1-yl)phenyl)-6-phenylquinolin-4-amine | MAPKAPK2 |
| N-(4-(4-sec-butylpiperazin-1-yl)phenyl)-6-(4-methoxyphenyl)quinolin-4-amine | MAPKAPK2 |
| N-(4-(4-cyclopentylpiperazin-1-yl)phenyl)-6-(4-methoxyphenyl)quinolin-4-amine | MAPKAPK2 |
| N-(4-(4-cyclohexylpiperazin-1-yl)phenyl)-6-(4-methoxyphenyl)quinolin-4-amine | MAPKAPK2 |
| 4-(4-(4-isopropylpiperazin-1-yl)phenylamino)quinolin-6-yl)benzonitrile | MAPKAPK2 |
| 4-(4-(4-cyclopentylpiperazin-1-yl)phenylamino)quinolin-6-yl)benzonitrile | MAPKAPK2 |
| 4-(4-(4-(2-methoxyethyl)piperazin-1-yl)phenylamino)quinolin-6-yl)benzonitrile | MAPKAPK2 |
| 2-(4-(4-(6-(4-cyanophenyl)quinolin-4-ylamino)phenyl)piperazin-1-yl)-N,N-dimethylacetamide | MAPKAPK2 |
| N-(4-(4-methylpiperazin-1-yl)phenyl)-6-(naphthalen-2-yl)quinolin-4-amine | MAPKAPK2 PRAK C-TAK1 CHEK1 CHEK2 DYRK2 NEK2 SYK BMX NEK2 SYK BMX |
| N-(4-(4-methylpiperazin-1-yl)phenyl)-6-(naphthalen-1-yl)quinolin-4-amine | MAPKAPK2 NEK2 PRAK CDK1/cyclin B |

TABLE 1-continued

| Compound Name | Activity |
| --- | --- |
| | KIT |
| | AKT3 |
| | C-TAK1 |
| | LYNA |
| | BMX |
| | SYK |
| | P38-δ |
| | P38-β |
| | P38-α |
| | SRC |
| | ABL1 |
| | LCK |
| | CHEK2 |
| N-(4-(4-methylpiperazin-1-yl)phenyl)-6-(thiophen-2-yl)quinolin-4-amine | PRAK |
| | MAPKAPK2 |
| | GSK3-α |
| | CDK2/cyclin A |
| | CHEK2 |
| N-(4-(4-methylpiperazin-1-yl)phenyl)-6-(thiophen-3-yl)quinolin-4-amine | PRAK |
| | MAPKAPK2 |
| 6-(furan-2-yl)-N-(4-(4-methylpiperazin-1-yl)phenyl)quinolin-4-amine | PRAK |
| | MAPKAPK2 |
| | CHEK2 |
| 6-(furan-3-yl)-N-(4-(4-methylpiperazin-1-yl)phenyl)quinolin-4-amine | DYRK2 |
| | MAPKAPK2 |
| | GSK-3-β |
| | DYRK2 |
| | GSK3-α |
| N-(4-(4-methylpiperazin-1-yl)phenyl)-6-(pyridin-3-yl)quinolin-4-amine | MAPKAPK2 |
| | PRAK |
| | AKT3 |
| N-(4-(4-methylpiperazin-1-yl)phenyl)-6-(pyridin-4-yl)quinolin-4-amine | DYRK2 |
| | ROCK2 |
| | MSK1 |
| | GSK-3-β |
| | GSK-3-α |
| | FLT-3 |
| | AKT1 |
| | CDK5 |
| | P70S6K1 |
| | CDK5 |
| | CK2 |
| | NEK2 |
| | PRAK |
| | AKT1 |
| | KIT |
| | PKA |
| | AKT3 |
| 6-(benzo[b]thiophen-3-yl)-N-(4-(4-methylpiperazin-1-yl)phenyl)quinolin-4-amine | MAPKAPK2 |
| | PRAK |
| | ABL1 |
| 1-(5-(4-(4-(4-methylpiperazin-1-yl)phenylamino)quinolin-6-yl)thiophen-2-yl)ethanone | MAPKAPK2 |
| | PRAK |
| 6-(benzo[b]thiophen-2-yl)-N-(4-(4-methylpiperazin-1-yl)phenyl)quinolin-4-amine | MAPKAPK2 |
| | C-TAK1 |
| | SRC |
| 6-(5-chlorothiophen-2-yl)-N-(4-(4-methylpiperazin-1-yl)phenyl)quinolin-4-amine | MAPKAPK2 |
| N-(4-(4-methylpiperazin-1-yl)phenyl)-6-(4-methylthiophen-2-yl)quinolin-4-amine | MAPKAPK2 |
| | PRAK |
| | P70S6K1 |
| | NEK2 |
| | CHEK2 |
| N-(4-(4-methylpiperazin-1-yl)phenyl)-6-(pyrimidin-5-yl)quinolin-4-amine | MAPKAPK2 |
| N-(4-(4-methylpiperazin-1-yl)phenyl)-6,8'-biquinolin-4-amine | MAPKAPK2 |
| | KIT |
| | PRAK |
| | P38-δ |
| | BMX |
| N-methyl-N-(4-(4-methylpiperazin-1-yl)phenyl)-6-phenylquinolin-4-amine | KIT |
| | FLT-3 |
| | MAPKAPK2 |
| | BMX |
| N-(4-(4-methylpiperazin-1-yl)phenyl)-6-phenyl-N-propylquinolin-4-amine | MAPKAPK2 |
| 6-(4-methoxyphenyl)-N-methyl-N-(4-(4-methylpiperazin-1- | KIT |

TABLE 1-continued

| Compound Name | Activity |
|---|---|
| yl)phenyl)quinolin-4-amine | MAPKAPK2<br>FLT-3<br>DYRK2<br>PDGFR-α<br>BMX |
| 6-(4-methoxyphenyl)-N-(4-(4-methylpiperazin-1-yl)phenyl)-N-propylquinolin-4-amine | MAPKAPK2 |
| 4-(4-(methyl(4-(4-methylpiperazin-1-yl)phenyl)amino)quinolin-6-yl)benzonitrile | MAPKAPK2<br>KIT<br>FLT-3<br>BMX |
| 4-(4-(4-(4-methylpiperidin-1-yl)phenylamino)quinolin-6-yl)benzonitrile | MAPKAPK2 |
| 4-(4-(4-(dimethylamino)piperidin-1-yl)phenylamino)quinolin-6-yl)benzonitrile | KIT |
| 4-(4-(4-(2-((dimethylamino)methyl)pyrrolidin-1-yl)phenylamino)quinolin-6-yl)benzonitrile | MAPKAPK2 |
| 4-(4-(4-(3-((dimethylamino)methyl)piperidin-1-yl)phenylamino)quinolin-6-yl)benzonitrile | MAPKAPK2 |
| 4-(4-(4-((dimethylamino)methyl)piperidin-1-yl)phenylamino)quinolin-6-yl)benzonitrile | MAPKAPK2 |
| 4-(4-(4-(3-(dimethylamino)piperidin-1-yl)phenylamino)quinolin-6-yl)benzonitrile | MAPKAPK2 |
| 4-(4-(4-(3-(dimethylamino)pyrrolidin-1-yl)phenylamino)quinolin-6-yl)benzonitrile | PRAK |
| 4-(4-(4-(3-(methylamino)pyrrolidin-1-yl)phenylamino)quinolin-6-yl)benzonitrile | PRAK<br>CDK1/cyclin B<br>KIT |
| 6-(3-chlorophenyl)-N-(4-(3-(dimethylamino)pyrrolidin-1-yl)phenyl)quinolin-4-amine | MAPKAPK2 |
| 6-(4-chlorophenyl)-N-(4-(3-(dimethylamino)pyrrolidin-1-yl)phenyl)quinolin-4-amine | MAPKAPK2 |
| N-(4-(3-(dimethylamino)pyrrolidin-1-yl)phenyl)-6-m-tolylquinolin-4-amine | MAPKAPK2 |
| N-(4-(3-(dimethylamino)pyrrolidin-1-yl)phenyl)-6-p-tolylquinolin-4-amine | MAPKAPK2 |
| N-(4-(3-(dimethylamino)pyrrolidin-1-yl)phenyl)-6-(3-methoxyphenyl)quinolin-4-amine | MAPKAPK2 |
| N-(4-(3-(dimethylamino)pyrrolidin-1-yl)phenyl)-6-(4-methoxphenyl)quinolin-4-amine | MAPKAPK2 |
| N-(4-(3-(dimethylamino)pyrrolidin-1-yl)phenyl)-6-(4-fluoro-3-methylphenyl)quinolin-4-amine | MAPKAPK2 |
| 6-(3-(benzyloxy)phenyl)-N-(4-(3-(dimethylamino)pyrrolidin-1-yl)phenyl)quinolin-4-amine | MAPKAPK2 |
| N-(4-(3-(dimethylamino)pyrrolidin-1-yl)phenyl)-6-(4-vinylphenyl)quinolin-4-amine | MAPKAPK2 |
| 6-(3,4-dichlorophenyl)-N-(4-(3-(dimethylamino)pyrrolidin-1-yl)phenyl)quinolin-4-amine | MAPKAPK2 |
| N-(4-(3-(dimethylamino)pyrrolidin-1-yl)phenyl)-6-(3,4-dimethylphenyl)quinolin-4-amine | MAPKAPK2 |
| N-(4-(3-(dimethylamino)pyrrolidin-1-yl)phenyl)-6-(naphthalen-2-yl)quinolin-4-amine | MAPKAPK2 |
| N-(4-(3-(dimethylamino)pyrrolidin-1-yl)phenyl)-6-(4-isopropylphenyl)quinolin-4-amine | MAPKAPK2 |
| 6-(benzo[b]thiophen-3-yl)-N-(4-(3-(dimethylamino)pyrrolidin-1-yl)phenyl)quinolin-4-amine | MAPKAPK2 |
| N-(4-(3-(dimethylamino)pyrrolidin-1-yl)phenyl)-6-(5-methylpyridin-2-yl)quinolin-4-amine | MAPKAPK2 |
| N-(4-(3-(dimethylamino)pyrrolidin-1-yl)phenyl)-6-(1H-indol-5-yl)quinolin-4-amine | MAPKAPK2 |
| 6-(4-(4-(3-(dimethylamino)pyrrolidin-1-yl)phenylamino)quinolin-6-yl)benzo[d]thiazol-2(3H)-one | MAPKAPK2 |
| 5-(4-(4-(3-(dimethylamino)pyrrolidin-1-yl)phenylamino)quinolin-6-yl)-2,3-dihydroinden-1-one | MAPKAPK2 |
| 5-(4-(4-(3-(dimethylamino)pyrrolidin-1-yl)phenylamino)quinolin-6-yl)nicotinic acid | MAPKAPK2 |
| 6-(6-chloropyridin-3-yl)-N-(4-(3-(dimethylamino)pyrrolidin-1-yl)phenyl)quinolin-4-amine | MAPKAPK2 |
| N-(4-(3-(dimethylamino)pyrrolidin-1-yl)phenyl)-6-(1H-indol-4-yl)quinolin-4-amine | MAPKAPK2 |
| 6-(6-chloro-5-methylpyridin-3-yl)-N-(4-(3-(dimethylamino)pyrrolidin-1-yl)phenyl)quinolin-4-amine | MAPKAPK2 |
| N-(4-(3-(dimethylamino)pyrrolidin-1-yl)phenyl)-6-(thiazol-2-yl)quinolin-4-amine | MAPKAPK2 |
| 1-(5-(4-(4-(3-(dimethylamino)pyrrolidin-1-yl)phenylamino)quinolin-6-yl)indolin-1-yl)ethanone | MAPKAPK2 |
| 4-(4-(4-(3-(dimethylamino)pyrrolidin-1-yl)phenylamino)quinolin-6-yl)-2-methylbenzonitrile | MAPKAPK2 |

TABLE 1-continued

| Compound Name | Activity |
|---|---|
| 6-(4-(difluoromethoxy)phenyl)-N-(4-(3-(dimethylamino)pyrrolidin-1-yl)phenyl)quinolin-4-amine | MAPKAPK2 |
| 6-(4-(diethylamino)phenyl)-N-(4-(3-(dimethylamino)pyrrolidin-1-yl)phenyl)quinolin-4-amine | MAPKAPK2 |
| N-(4-(3-(dimethylamino)pyrrolidin-1-yl)phenyl)-6-(1H-indol-6-yl)quinolin-4-amine | MAPKAPK2 |
| 4-(4-(4-(3-(dimethylamino)pyrrolidin-1-yl)phenylamino)quinolin-6-yl)-2-fluorobenzonitrile | MAPKAPK2 |
| 6-(4-chloro-3-methoxyphenyl)-N-(4-(3-(dimethylamino)pyrrolidin-1-yl)phenyl)quinolin-4-amine | MAPKAPK2 |
| 6-(4-chloro-3-fluorophenyl)-N-(4-(3-(dimethylamino)pyrrolidin-1-yl)phenyl)quinolin-4-amine | MAPKAPK2 |
| 6-(benzo[d][1,3]dioxol-5-yl)-N-(4-(3-(dimethylamino)pyrrolidin-1-yl)phenyl)quinolin-4-amine | MAPKAPK2 |
| N-(4-(3-(dimethylamino)pyrrolidin-1-yl)phenyl)-6-(3-fluoro-4-methylphenyl)quinolin-4-amine | MAPKAPK2 |
| 6-(3-chloro-4-methylphenyl)-N-(4-(3-(dimethylamino)pyrrolidin-1-yl)phenyl)quinolin-4-amine | MAPKAPK2 |
| N-(4-(3-(dimethylamino)pyrrolidin-1-yl)phenyl)-6-(3-fluoro-4-methoxyphenyl)quinolin-4-amine | MAPKAPK2 |
| 6-(4-chloro-3-methylphenyl)-N-(4-(3-(dimethylamino)pyrrolidin-1-yl)phenyl)quinolin-4-amine | MAPKAPK2 |
| 6-(4-chlorophenyl)-N-(4-(3-(diethylamino)pyrrolidin-1-yl)phenyl)quinolin-4-amine | MAPKAPK2 |
| 4-(4-(4-(3-(diethylamino)pyrrolidin-1-yl)phenylamino)quinolin-6-yl)benzonitrile | MAPKAPK2 |
| N-(4-(3-(diethylamino)pyrrolidin-1-yl)phenyl)-6-(naphthalen-2-yl)quinolin-4-amine | MAPKAPK2 |
| (R)-6-(4-chlorophenyl)-N-(4-(3-(dimethylamino)pyrrolidin-1-yl)phenyl)quinolin-4-amine | MAPKAPK2 |
| (R)-4-(4-(4-(3-(dimethylamino)pyrrolidin-1-yl)phenylamino)quinolin-6-yl)benzonitrile | MAPKAPK2 |
| (R)-N-(4-(3-(dimethylamino)pyrrolidin-1-yl)phenyl)-6-(naphthalen-2-yl)quinolin-4-amine | MAPKAPK2 |
| (S)-6-(4-chlorophenyl)-N-(4-(3-(dimethylamino)pyrrolidin-1-yl)phenyl)quinolin-4-amine | MAPKAPK2 |
| (S)-4-(4-(4-(3-(dimethylamino)pyrrolidin-1-yl)phenylamino)quinolin-6-yl)benzonitrile | MAPKAPK2 |
| (S)-N-(4-(3-(dimethylamino)pyrrolidin-1-yl)phenyl)-6-(naphthalen-2-yl)quinolin-4-amine | MAPKAPK2 |
| 4-(4-(4-(3-(benzyl(methyl)amino)pyrrolidin-1-yl)phenylamino)quinolin-6-yl)benzonitrile | MAPKAPK2 |
| 4-(4-(4-(3-(methyl(3,3,3-trifluoropropyl)amino)pyrrolidin-1-yl)phenylamino)quinolin-6-yl)benzonitrile | MAPKAPK2 |
| 6-(4-chlorophenyl)-N-(6-(4-methylpiperazin-1-yl)pyridin-3-yl)quinolin-4-amine | MAPKAPK2 |
| 4-(4-(6-(4-methylpiperazin-1-yl)pyridazin-3-ylamino)quinolin-6-yl)benzonitrile | MAPKAPK2 |
| 4-(4-(6-(4-methylpiperazin-1-yl)pyridin-3-ylamino)quinolin-6-yl)benzonitrile | MAPKAPK2 |
| 4-(4-(4-(4-methylpiperazin-1-yl)phenoxy)quinolin-6-yl)benzonitrile | MAPKAPK2 |
| 6-(4-chlorophenyl)-4-(4-(4-methylpiperazin-1-yl)phenoxy)quinoline | MAPKAPK2 |
| 4-(4-(4-(1-methylpiperidin-4-yl)phenylamino)quinolin-6-yl)benzonitrile | MAPKAPK2 |
| 4-(4-(4-(piperidin-4-yl)phenylamino)quinolin-6-yl)benzonitrile | KIT |
| N1-(3,6'-biquinolin-4'-yl)-N4-methyl-N4-(1-methylpyrrolidin-3-yl)benzene-1,4-diamine | MAPKAPK2 |
| 4-(4-(4-(methyl(1-methylpyrrolidin-3-yl)amino)phenylamino)quinolin-6-yl)benzonitrile | MAPKAPK2 |
| N1-methyl-N4-(6-(5-methylpyridin-2-yl)quinolin-4-yl)-N1-(1-methylpyrrolidin-3-yl)benzene-1,4-diamine | MAPKAPK2 |

What is claimed is:

1. A compound or Formula 1 or a

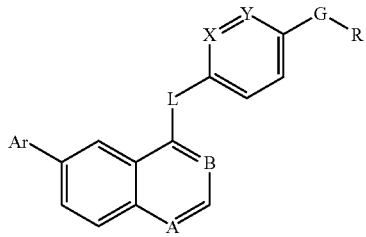
(Formula 1)

pharmaceutically acceptable salt thereof, wherein:
Ar is chosen from aryl, substituted aryl, heteroaryl, and substituted heteroaryl;
A is —N— and B is —CH—, or A is —CH— and B is —N—;
L is chosen from NR¹ and O;
R¹ is chosen from H, alkyl, substituted alkyl, cycloalkyl, substituted cycloalkyl, heterocycloalkyl, and substituted heterocycloalkyl;
X and Y are independently chosen from CH and N;
G is chosen from a covalent bond and NR⁶;
R⁶ is chosen from hydrogen and optionally substituted alkyl; and
R is chosen from optionally substituted heterocycloalkyl, with the proviso that when Ar is phenyl, A is —N—, B is —CH—, L is NR¹, R¹ is H, X is CH,
Y is CH, and G is a covalent bond, then R is not 4-methylpiperazin-1-yl.

2. The compound of claim 1 wherein A is —N— and B is —CH—.

3. The compound of claim 1 wherein A is —CH— and B is —N—.

4. The compound of claim 1 wherein R is chosen from optionally substituted piperidinyl, optionally substituted pyrrolidinyl, and optionally substituted piperazinyl.

5. The compound of claim 1 wherein G is a covalent bond.

6. The compound of claim 1 wherein G is NR⁶.

7. The compound of claim 1 wherein the compound of Formula 1 is chosen from compounds of Formula 2:

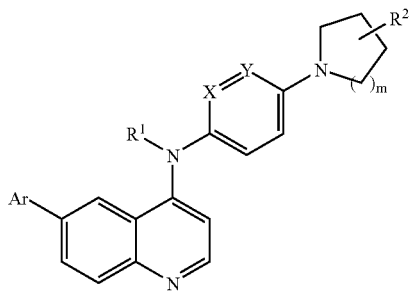
(Formula 2)

wherein
m is an integer chosen from 1, 2, and 3; and
R² is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

8. The compound of claim 1 wherein the compound of Formula 1 is chosen from compounds of Formula 3:

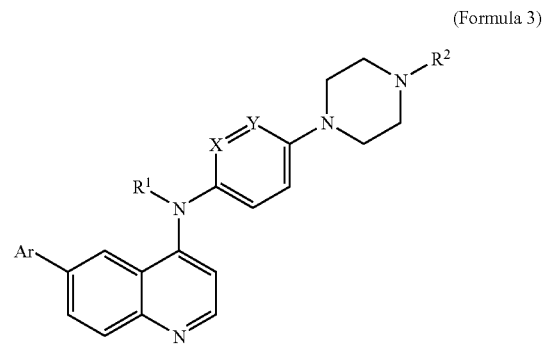
(Formula 3)

wherein
R² is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

9. The compound of claim 1 wherein the compound of Formula 1 is chosen from compounds of Formula 4:

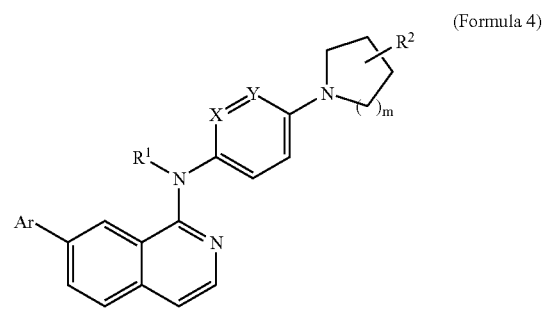
(Formula 4)

wherein
m is an integer chosen from 1, 2, and 3; and
R² is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

10. The compound of claim 1 wherein the compound of Formula 1 is chosen from compounds of Formula 5:

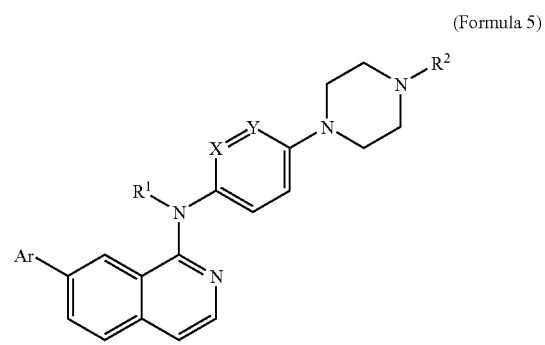
(Formula 5)

wherein
R² is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

11. The compound of claim 1 wherein the compound of Formula 1 is chosen from compounds of Formula 6:

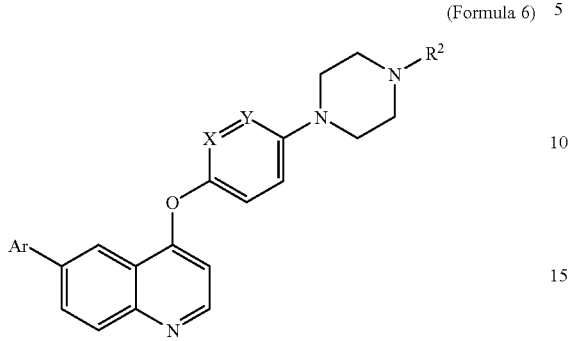

(Formula 6)

wherein
- $R^2$ is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

12. The compound of claim 7 wherein $R^2$ is chosen from H, alkyl, substituted alkyl, cycloalkyl, substituted cycloalkyl, and —$NR^4R^5$, wherein
- $R^4$ and $R^5$ are independently chosen from H, alkyl, and substituted alkyl; and
- when $R^2$ is attached to a carbon α to the ring nitrogen, then $R^2$ is not —$NR^4R^5$.

13. The compound of claim 12 wherein $R^2$ is chosen from alkyl, and substituted alkyl.

14. The compound of claim 12 wherein $R^2$ is independently chosen from —$NR^4R^1$ and —$CH_2$—$NR^4R^5$.

15. The compound of claim 14 wherein
- $R^2$ is —$NR^4R^5$ and
- $R^4$ and $R^5$ are independently chosen from $C_{1-4}$ alkyl, and substituted $C_{1-4}$ alkyl.

16. The compound of claim 15 wherein $R^2$ is —$N(CH_3)_2$.

17. The compound of claim 1 wherein the compound of Formula 1 is chosen from compounds of Formula 7:

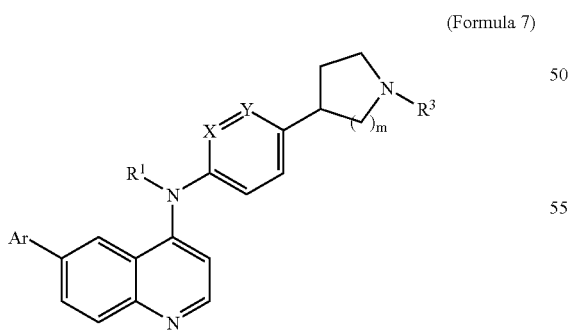

(Formula 7)

wherein
- m is an integer chosen from 1, 2, and 3; and
- $R^3$ is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

18. The compound of claim 1 wherein the compound of Formula 1 is chosen from compounds of Formula 8:

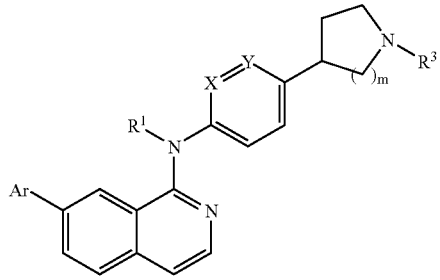

(Formula 8)

wherein
- m is an integer chosen from 1, 2, and 3; and
- $R^3$ is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

19. The compound of claim 1 wherein the compound of Formula 1 is chosen from compounds of Formula 9:

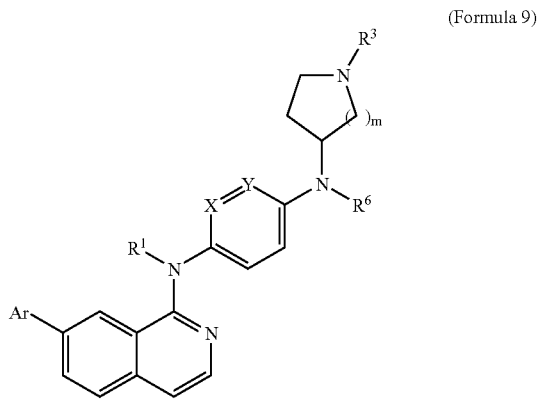

(Formula 9)

wherein
- m is an integer chosen from 1, 2, and 3; and
- $R^3$ is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

20. The compound of claim 1 wherein the compound of Formula 1 is chosen from compounds of Formula 10:

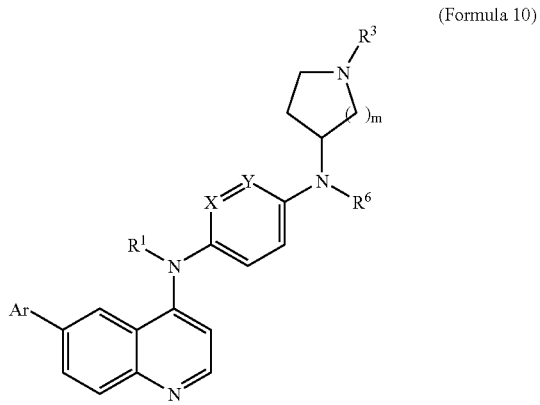

(Formula 10)

wherein
   m is an integer chosen from 1, 2, and 3; and
   R³ is chosen from H, alkyl, substituted alkyl, cycloalkyl, substituted cycloalkyl, heterocycloalkyl, substituted heterocycloalkyl, aryl, substituted aryl, heteroaryl, and substituted heteroaryl.

21. The compound of claim 19 wherein R⁶ is chosen from hydrogen and lower alkyl.

22. The compound of claim 17 wherein R³ is chosen from H, alkyl, substituted alkyl, cycloalkyl, substituted cycloalkyl, aryl, substituted aryl, heteroaryl, and substituted heteroaryl.

23. The compound of claim 22 wherein R³ is chosen from H, alkyl, and substituted alkyl.

24. The compound of claim 23 wherein R³ is chosen from $C_{1-4}$ alkyl, and substituted $C_{1-4}$ alkyl.

25. The compound of claim 1 wherein R¹ is chosen from hydrogen, alkyl, and substituted alkyl.

26. The compound of claim 25 wherein R¹ is hydrogen.

27. The compound of claim 1 wherein Ar is chosen from aryl and substituted aryl.

28. The compound of claim 27 wherein Ar is chosen from phenyl, substituted phenyl, and naphthyl.

29. The compound of claim 28 wherein Ar is chosen from phenyl and substituted phenyl.

30. The compound of claim 29 wherein Ar is substituted phenyl.

31. The compound of claim 27 wherein the substituent groups are selected from halogen, —CN, —OH, —COOH, —NO₂, $C_{1-8}$ alkoxy, substituted $C_{1-8}$ alkoxy, $C_{1-8}$ alkyl, substituted $C_{1-8}$ alkyl, $C_{5-10}$ aryl, substituted $C_{5-10}$ aryl, $C_{5-10}$ cycloalkyl, substituted $C_{5-10}$ cycloalkyl, $C_{1-8}$ alkylthio, substituted $C_{1-8}$ alkylthio, $C_{1-8}$ alkylsulfinyl, substituted $C_{1-8}$ alkylsulfinyl, $C_{1-8}$ alkylamino, substituted $C_{1-8}$ alkylamino, $C_{1-8}$ aminocarbonyl, substituted $C_{1-8}$ aminocarbonyl, $C_{1-8}$ alkylcarbonylamino, substituted $C_{1-8}$ alkylcarbonylamino, $C_{1-8}$ alkylsulfonyl, substituted $C_{1-8}$ alkylsulfonyl, $C_{1-8}$ alkylcarbonyl, and substituted $C_{1-8}$ alkylcarbonyl.

32. The compound claim 1 wherein X is CH and Y is CH.

33. The compound of claim 1 wherein X is CH and Y is N.

34. The compound of claim 1 wherein X is N and Y is N.

35. The compound of claim 1 wherein the at least one chemical entity inhibits at least one ATP-utilizing enzyme.

36. The compound of claim 35, wherein the at least one ATP-utilizing enzyme is a human protein kinase.

37. The compound of claim 36, wherein the human protein kinase is chosen from ABL1, AKT1, AKT2, AKT3, AURORA-A, BMX, c-TAK1, CDK1, CDK1/cyclinB, CDK2/cyclinA, CDK2/cyclinE, CDK5, CHEK1, CHEK2, CK2, CSK, DAPK1, DYRK2, FLT-3, FYN, GSK3-α, GSK3-β, HCK, INSR, KIT, LCK, LYNA, MAPKAPK2, MAPKAPK3, MSK1, MSK2, NEK2, p38-α, p38-β, p38-δ, p38-γ, P70S6K1, PAK2, PDGFR-α, PAK1, PKA, PRAK, ROCK2, SGK1, SRC, SYK, PIM-1-kinase, PDK1, and RSK2.

38. The compound of claim 37, wherein the human protein kinase is MAPKAPK2.

39. The compound of claim 1 chosen from:
   N-(4-(4-methylpiperazin-1-yl)phenyl)-6-phenylquinolin-4-amine;
   6-(3-chlorophenyl)-N-(4-(4-methylpiperazin-1-yl)phenyl)quinolin-4-amine;
   6-(4-chlorophenyl)-N-(4-(4-methylpiperazin-1-yl)phenyl)quinolin-4-amine;
   N-(4-(4-methylpiperazin-1-yl)phenyl)-6-o-tolylquinolin-4-amine;
   N-(4-(4-methylpiperazin-1-yl)phenyl)-6-m-tolylquinolin-4-amine;
   N-(4-(4-methylpiperazin-1-yl)phenyl)-6-p-tolylquinolin-4-amine;
   6-(2-methoxyphenyl)-N-(4-(4-methylpiperazin-1-yl)phenyl)quinolin-4-amine;
   6-(3-methoxyphenyl)-N-(4-(4-methylpiperazin-1-yl)phenyl)quinolin-4-amine;
   6-(4-methoxyphenyl)-N-(4-(4-methylpiperazin-1-yl)phenyl)quinolin-4-amine;
   2-(4-(4-(4-methylpiperazin-1-yl)phenylamino)quinolin-6-yl)benzamide;
   3-(4-(4-(4-methylpiperazin-1-yl)phenylamino)quinolin-6-yl)benzonitrile;
   4-(4-(4-(4-methylpiperazin-1-yl)phenylamino)quinolin-6-yl)benzonitrile;
   6-(3,4-dimethoxyphenyl)-N-(4-(4-methylpiperazin-1-yl)phenyl)quinolin-4-amine;
   6-(2,4-difluorophenyl)-N-(4-(4-methylpiperazin-1-yl)phenyl)quinolin-4-amine;
   6-(4-fluoro-3-methylphenyl)-N-(4-(4-methylpiperazin-1-yl)phenyl)quinolin-4-amine;
   (3-(4-(4-(4-methylpiperazin-1-yl)phenylamino)quinolin-6-yl)phenyl)methanol;
   6-(5-fluoro-2-methoxyphenyl)-N-(4-(4-methylpiperazin-1-yl)phenyl)quinolin-4-amine;
   3-(4-(4-(4-methylpiperazin-1-yl)phenylamino)quinolin-6-yl)phenol;
   6-(3-chloro-4-fluorophenyl)-N-(4-(4-methylpiperazin-1-yl)phenyl)quinolin-4-amine;
   4-(4-(4-(4-methylpiperazin-1-yl)phenylamino)quinolin-6-yl)phenol;
   6-(2,3-dimethylphenyl)-N-(4-(4-methylpiperazin-1-yl)phenyl)quinolin-4-amine;
   6-(2,5-dimethoxyphenyl)-N-(4-(4-methylpiperazin-1-yl)phenyl)quinolin-4-amine;
   6-(2-ethylphenyl)-N-(4-(4-methylpiperazin-1-yl)phenyl)quinolin-4-amine;
   4-(4-(4-(4-methylpiperazin-1-yl)phenylamino)quinolin-6-yl)benzamide;
   6-(4-(ethylthio)phenyl)-N-(4-(4-methylpiperazin-1-yl)phenyl)quinolin-4-amine;
   6-(2,5-difluorophenyl)-N-(4-(4-methylpiperazin-1-yl)phenyl)quinolin-4-amine;
   6-(fluorophenyl)-N-(4-(4-methylpiperazin-1yl)phenyl)quinolin-4-amine;
   6-(2,3-dichlorophenyl)-N-(4-(4-methylpiperazin-1-yl)phenyl)quinolin-4-amine;
   6-(2,5-dimethylphenyl)-N-(4-(4-methylpiperazin-1-yl)phenyl)quinolin-4-amine;
   3-(4-(4-(4-methylpiperazin-1-yl)phenylamino)quinolin-6-yl)benzoic acid;
   N-(4-(4-methylpiperazin-1-yl)phenyl)-6-(4-(methylthio)phenyl)quinolin-4-amine;
   6-(3-ethoxyphenyl)-N-(4-(4-methylpiperazin-1-yl)phenyl)quinolin-4-amine;
   N-(4-(4-methylpiperazin-1-yl)phenyl)-6-(2-(trifluoromethyl)phenyl)quinolin-4-amine;
   6-(3-(benzyloxy)phenyl)-N-(4-(4-methylpiperazin-1-yl)phenyl)quinolin-4-amine;
   N-(4-(4-methylpiperazin-1-yl)phenyl)-6-(4-vinylphenyl)quinolin-4-amine;
   6-(2,4-dimethoxyphenyl)-N-(4-(4-methylpiperazin-1-yl)phenyl)quinolin-4-amine;
   N-(4-(4-methylpiperazin-1-yl)phenyl)-6-(3,4,5-trifluorophenyl)quinolin-4-amine;
   (4-(4-(4-(4-methylpiperazin-1-yl)phenylamino)quinolin-6-yl)phenyl)methanol;

N-(4-(4-methylpiperazin-1-yl)phenyl)-6-(4-phenoxyphenyl)quinolin-4-amine;
6-(4-ethoxyphenyl)-N-(4-(4-methylpiperazin-1-yl)phenyl)quinolin-4-amine;
6-(3,4-dichlorophenyl)-N-(4-(4-methylpiperazin-1-yl)phenyl)quinolin-4-amine;
N-(4-(4-methylpiperazin-1-yl)phenyl)-6-(4-(trifluoromethyl)phenyl)quinolin-4-amine;
6-(2,5-dichlorophenyl)-N-(4-(4-methylpiperazin-1-yl)phenyl)quinolin-4-amine;
6-(2,4-dichlorophenyl)-N-(4-(4-methylpiperazin-1-yl)phenyl)quinolin-4-amine;
6-(3-isopropylphenyl)-N-(4-(4-methylpiperazin-1-yl)phenyl)quinolin-4-amine;
6-(4-isopropylphenyl)-N-(4-(4-methylpiperazin-1-yl)phenyl)quinolin-4-amine;
6-(4-fluoro-2-methylphenyl)-N-(4-(4-methylpiperazin-1-yl)phenyl)quinolin-4-amine;
6-(3,4-difluorophenyl)-N-(4-(4-methylpiperazin-1-yl)phenyl)quinolin-4-amine;
6-(biphenyl-3-yl)-N-(4-(4-methylpiperazin-1-yl)phenyl)quinolin-4-amine;
6-(5-isopropyl-2-methoxyphenyl)-N-(4-(4-methylpiperazin-1-yl)phenyl)quinolin-4-amine;
N-(3-(4-(4-(4-methylpiperazin-1-yl)phenylamino)quinolin-6-yl)phenyl)acetamide;
6-(2,4-bis(trifluoromethyl)phenyl)-N-(4-(4-methylpiperazin-1-yl)phenyl)quinolin-4-amine;
N-(4-(4-methylpiperazin-1-yl)phenyl)-6-(4-(methylsulfinyl)phenyl)quinolin-4-amine;
N-(4-(4-methylpiperazin-1-yl)phenyl)-6-(4-pentylphenyl)quinolin-4-amine;
6-(3,5-bis(trifluoromethyl)phenyl)-N-(4-(4-methylpiperazin-1-yl)phenyl)quinolin-4-amine;
6-(4-butylphenyl)-N-(4-(4-methylpiperazin-1-yl)phenyl)quinolin-4-amine;
3-(4-(4-(4-(4-methylpiperazin-1-yl)phenylamino)quinolin-6-yl)phenyl)propanoic acid;
N-(4-(4-methylpiperazin-1-yl)phenyl)-6-(3-nitrophenyl)quinolin-4-amine;
6-(3-fluorophenyl)-N-(4-(4-methylpiperazin-1-yl)phenyl)quinolin-4-amine;
6-(2-fluorophenyl)-N-(4-(4-methylpiperazin-1-yl)phenyl)quinolin-4-amine;
6-(4-tert-butylphenyl)-N-(4-(4-methylpiperazin-1-yl)phenyl)quinolin-4-amine;
N-(4-(4-methylpiperazin-1-yl)phenyl)-6-(3-(trifluoromethoxy)phenyl)quinolin-4-amine;
N-(4-(4-methylpiperazin-1-yl)phenyl)-6-(4-(trifluoromethoxy)phenyl)quinolin-4-amine;
6-(2,6-difluorophenyl)-N-(4-(4-methylpiperazin-1-yl)phenyl)quinolin-4-amine;
N-(4-(4-methylpiperazin-1-yl)phenyl)-6-(3-(trifluoromethyl)phenyl)quinolin-4-amine;
6-(4-(benzyloxy)phenyl)-N-(4-(4-methylpiperazin-1-yl)phenyl)quinolin-4-amine;
6-(2-((dimethylamino)methyl)phenyl)-N-(4-(4-methylpiperazin-1-yl)phenyl)quinolin-4-amine;
6-(4-(benzyloxy)-3-fluorophenyl)-N-(4-(4-methylpiperazin-1-yl)phenyl)quinolin-4-amine;
6-(4-cyclohexylphenyl)-N-(4-(4-methylpiperazin-1-yl)phenyl)quinolin-4-amine;
6-(3,4-dimethylphenyl)-N-(4-(4-methylpiperazin-1-yl)phenyl)quinolin-4-amine;
6-phenyl-N-(4-(piperazin-1-yl)phenyl)quinolin-4-amine;
N-(4-(4-ethylpiperazin-1-yl)phenyl)-6-phenylquinolin-4-amine;
6-phenyl-N-(4-(4-propylpiperazin-1-yl)phenyl)quinolin-4-amine;
N-(4-(4-butylpiperazin-1-yl)phenyl)-6-phenylquinolin-4-amine;
N-(4-(4-isopropylpiperazin-1-yl)phenyl)-6-phenylquinolin-4-amine;
N-(4-(4-(pentan-3-yl)piperazin-1-yl)phenyl)-6-phenylquinolin-4-amine;
2-(4-(4-(6-phenylquinolin-4-ylamino)phenyl)piperazin-1-yl)ethanol;
N-(4-(4-(2-methoxyethyl)piperazin-1-yl)phenyl)-6-phenylquinolin-4-amine;
3-(4-(4-(6-phenylquinolin-4-ylamino)phenyl)piperazin-1-yl)propan-1-ol;
N-(4-(4-(2-(dimethylamino)ethyl)piperazin-1-yl)phenyl)-6-phenylquinolin-4-amine;
3-(4-(4-(6-phenylquinolin-4-ylamino)phenyl)piperazin-1-yl)propanenitrile;
2-(4-(4-(6-phenylquinolin-4-ylamino)phenyl)piperazin-1-yl)acetic acid;
6-(4-methoxyphenyl)-N-(4-(piperazin-1-yl)phenyl)quinolin-4-amine;
N-(4-(4-ethylpiperazin-1-yl)phenyl)-6-(4-methoxyphenyl)quinolin-4-amine;
6-(4-methoxyphenyl)-N-(4-(4-propylpiperazin-1-yl)phenyl)quinolin-4-amine;
N-(4-(4-butylpiperazin-1-yl)phenyl)-6-(4-methoxyphenyl)quinolin-4-amine;
N-(4-(4-isopropylpiperazin-1-yl)phenyl)-6-(4-methoxyphenyl)quinolin-4-amine;
2-(4-(4-(6-(4-methoxyphenyl)quinolin-4-ylamino)phenyl)piperazin-1-yl)ethanol;
3-(4-(4-(6-(4-methoxyphenyl)quinolin-4-ylamino)phenyl)piperazin-1-yl)propan-1-ol;
N-(4-(4-(2-(dimethylamino)ethyl)piperazin-1-yl)phenyl)-6-(4-methoxyphenyl)quinolin-4-amine;
3-(4-(4-(6-(4-methoxyphenyl)quinolin-4-ylamino)phenyl)piperazin-1-yl)propanenitrile;
2-(4-(4-(6-(4-methoxyphenyl)quinolin-4-ylamino)phenyl)piperazin-1-yl)-N,N-dimethylacetamide;
2-(4-(4-(6-(4-methoxyphenyl)quinolin-4-ylamino)phenyl)piperazin-1-yl)acetic acid;
4-(4-(4-(piperazin-1-yl)phenylamino)quinolin-6-yl)benzonitrile;
4-(4-(4-(4-ethylpiperazin-1-yl)phenylamino)quinolin-6-yl)benzonitrile;
4-(4-(4-(4-propylpiperazin-1-yl)phenylamino)quinolin-6-yl)benzonitrile;
4-(4-(4-(4-butylpiperazin-1-yl)phenylamino)quinolin-6-yl)benzonitrile;
4-(4-(4-(4-sec-butylpiperazin-1-yl)phenylamino)quinolin-6-yl)benzonitrile;
4-(4-(4-(4-(pentan-3-yl)piperazin-1-yl)phenylamino)quinolin-6-yl)benzonitrile;
4-(4-(4-(4-allylpiperazin-1-yl)phenylamino)quinolin-6-yl)benzonitrile;
4-(4-(4-(4-cyclohexylpiperazin-1-yl)phenylamino)quinolin-6-yl)benzonitrile;
4-(4-(4-(4-(2-hydroxyethyl)piperazin-1-yl)phenylamino)quinolin-6-yl)benzonitrile;
4-(4-(4-(4-(3-hydroxypropyl)piperazin-1-yl)phenylamino)quinolin-6-yl)benzonitrile;
4-(4-(4-(4-(2-(dimethylamino)ethyl)piperazin-1-yl)phenylamino)quinolin-6-yl)benzonitrile;
4-(4-(4-(4-(2-cyanoethyl)piperazin-1-yl)phenylamino)quinolin-6-yl)benzonitrile;

2-(4-(4-(6-(4-cyanophenyl)quinolin-4-ylamino)phenyl) piperazin-1-yl)acetic acid;
N-(4-(4-sec-butylpiperazin-1-yl)phenyl)-6-phenylquinolin-4-amine;
N-(4-(4-cyclopentylpiperazin-1-yl)phenyl)-6-phenylquinolin-4-amine;
4-(4-(4-(4-methylpiperidin-1-yl)phenylamino)quinolin-6-yl)benzonitrile;
4-(4-(4-(4-(dimethylamino)piperidin-1-yl)phenylamino) quinolin-6-yl)benzonitrile;
4-(4-(4-(2-((dimethylamino)methyl)pyrrolidin-1-yl)phenylamino)quinolin-6-yl)benzonitrile;
4-(4-(4-(3-((dimethylamino)methyl)piperidin-1-yl)phenylamino)quinolin-6-yl)benzonitrile;
4-(4-(4-(4-((dimethylamino)methyl)piperidin-1-yl)phenylamino)quinolin-6-yl)benzonitrile;
4-(4-(4-(3-(dimethylamino)piperidin-1-yl)phenylamino) quinolin-6-yl)benzonitrile;
4-(4-(4-(3-(dimethylamino)pyrrolidin-1-yl)phenylamino) quinolin-6-yl)benzonitrile;
4-(4-(4-(3-(methylamino)pyrrolidin-1-yl)phenylamino) quinolin-6-yl)benzonitrile;
6-(3-chlorophenyl)-N-(4-(3-(dimethylamino)pyrrolidin-1-yl)phenyl)quinolin-4-amine;
6-(4-chlorophenyl)-N-(4-(3-(dimethylamino)pyrrolidin-1-yl)phenyl)quinolin-4-amine;
N-(4-(3-(dimethylamino)pyrrolidin-1-yl)phenyl)-6-m-tolylquinolin-4-amine;
N-(4-(3-(dimethylamino)pyrrolidin-1-yl)phenyl)-6-p-tolylquinolin-4-amine;
N-(4-(3-(dimethylamino)pyrrolidin-1-yl)phenyl)-6-(3-methoxyphenyl)quinolin-4-amine;
N-(4-(3-(dimethylamino)pyrrolidin-1-yl)phenyl)-6-(4-methoxyphenyl)quinolin-4-amine;
N-(4-(3-(dimethylamino)pyrrolidin-1-yl)phenyl)-6-(4-fluoro-3-methylphenyl)quinolin-4-amine;
6-(3-(benzyloxy)phenyl)-N-(4-(3-(dimethylamino)pyrrolidin-1-yl)phenyl)quinolin-4-amine;
N-(4-(3-(dimethylamino)pyrrolidin-1-yl)phenyl)-6-(4-vinylphenyl)quinolin-4-amine;
6-(3,4-dichlorophenyl)-N-(4-(3-(dimethylamino)pyrrolidin-1-yl)phenyl)quinolin-4-amine;
N-(4-(3-(dimethylamino)pyrrolidin-1-yl)phenyl)-6-(3,4-dimethylphenyl)quinolin-4-amine;
N-(4-(3-(dimethylamino)pyrrolidin-1-yl)phenyl)-6-(naphthalen-2-yl)quinolin-4-amine;
N-(4-(3-(dimethylamino)pyrrolidin-1-yl)phenyl)-6-(4-isopropylphenyl)quinolin-4-amine;
6-(benzo[b]thiophen-3-yl)-N-(4-(3-(dimethylamino)pyrrolidin-1-yl)phenyl)quinolin-4-amine;
N-(4-(3-(dimethylamino)pyrrolidin-1-yl)phenyl)-6-(5-methylpyridin-2-yl)quinolin-4-amine;
N-(4-(3-(dimethylamino)pyrrolidin-1-yl)phenyl)-6-(1H-indol-5-yl)quinolin-4-amine;
6-(4-(4-(3-(dimethylamino)pyrrolidin-1-yl)phenylamino) quinolin-6-yl)benzo[d]thiazol-2 (3H)-one;
5-(4-(4-(3-(dimethylamino)pyrrolidin-1-yl)phenylamino) quinolin-6-yl)-2,3-dihydroinden-1-one;
5-(4-(4-(3-(dimethylamino)pyrrolidin-1-yl)phenylamino) quinolin-6-yl)nicotinic acid;
6-(6-chloropyridin-3-yl)-N-(4-(3-(dimethylamino)pyrrolidin-1-yl)phenyl)quinolin-4-amine;
N-(4-(3-(dimethylamino)pyrrolidin-1-yl)phenyl)-6-(1H-indol-4-yl)quinolin-4-amine;
6-(6-chloro-5-methylpyridin-3-yl)-N-(4-(3-(dimethylamino)pyrrolidin-1-yl)phenyl)quinolin-4-amine;
N-(4-(3-(dimethylamino)pyrrolidin-1-yl)phenyl)-6-(thiazol-2-yl)quinolin-4-amine;
1-(5-(4-(4-(3-(dimethylamino)pyrrolidin-1-yl)phenylamino)quinolin-6-yl)indolin-1-yl)ethanone;
4-(4-(4-(3-(dimethylamino)pyrrolidin-1-yl)phenylamino) quinolin-6-yl)-2-methylbenzonitrile;
6-(4-(difluoromethoxy)phenyl)-N-(4-(3-(dimethylamino) pyrrolidin-1-yl)phenyl)quinolin-4-amine;
6-(4-(diethylamino)phenyl)-N-(4-(3-(dimethylamino) pyrrolidin-1-yl)phenyl)quinolin-4-amine;
N-(4-(3-(dimethylamino)pyrrolidin-1-yl)phenyl)-6-(1H-indol-6-yl)quinolin-4-amine;
4-(4-(4-(3-(dimethylamino)pyrrolidin-1-yl)phenylamino) quinolin-6-yl)-2-fluorobenzonitrile;
6-(4-chloro-3-methoxyphenyl)-N-(4-(3-(dimethylamino) pyrrolidin-1-yl)phenyl)quinolin-4-amine;
6-(4-chloro-3-fluorophenyl)-N-(4-(3-(dimethylamino) pyrrolidin-1-yl)phenyl)quinolin-4-amine;
6-(benzo[d][1,3]dioxol-5-yl)-N-(4-(3-(dimethylamino) pyrrolidin-1-yl)phenyl)quinolin-4-amine;
N-(4-(3-(dimethylamino)pyrrolidin-1-yl)phenyl)-6-(3-fluoro-4-methylphenyl)quinolin-4-amine;
6-(3-chloro-4-methylphenyl)-N-(4-(3-(dimethylamino) pyrrolidin-1-yl)phenyl)quinolin-4-amine;
N-(4-(3-(dimethylamino)pyrrolidin-1-yl)phenyl)-6-(3-fluoro-4-methoxyphenyl)quinolin-4-amine;
6-(4-chloro-3-methylphenyl)-N-(4-(3-(dimethylamino) pyrrolidin-1-yl)phenyl)quinolin-4-amine;
6-(4-chlorophenyl)-N-(4-(3-(diethylamino)pyrrolidin-1-yl)phenyl)quinolin-4-amine;
4-(4-(4-(3-(diethylamino)pyrrolidin-1-yl)phenylamino) quinolin-6-yl)benzonitrile;
N-(4-(3-(diethylamino)pyrrolidin-1-yl)phenyl)-6-(naphthalen-2-yl)quinolin-4-amine;
(R)-6-(4-chlorophenyl)-N-(4-(3-(dimethylamino)pyrrolidin-1-yl)phenyl)quinolin-4-amine;
(R)-4-(4-(4-(3-(dimethylamino)pyrrolidin-1-yl)phenylamino)quinolin-6-yl)benzonitrile;
(R)-N-(4-(3-(dimethylamino)pyrrolidin-1-yl)phenyl)-6-(naphthalen-2-yl)quinolin-4-amine;
(S)-6-(4-chlorophenyl)-N-(4-(3-(dimethylamino)pyrrolidin-1-yl)phenyl)quinolin-4-amine;
(S)-4-(4-(4-(3-(dimethylamino)pyrrolidin-1-yl)phenylamino)quinolin-6-yl)benzonitrile;
(S)-N-(4-(3-(dimethylamino)pyrrolidin-1-yl)phenyl)-6-(naphthalen-2-yl)quinolin-4-amine;
4-(4-(4-(3-(benzyl(methyl)amino)pyrrolidin-1-yl)phenylamino)quinolin-6-yl)benzonitrile;
4-(4-(4-(3-(methyl(3,3,3-trifluoropropyl)amino)pyrrolidin-1-yl)phenylamino)quinolin-6-yl)benzonitrile;
6-(4-chlorophenyl)-N-(6-(4-methylpiperazin-1-yl)pyridin-3-yl)quinolin-4-amine;
4-(4-(6-(4-methylpiperazin-1-yl)pyridazin-3-ylamino) quinolin-6-yl)benzonitrile;
4-(4-(6-(4-methylpiperazin-1-yl)pyridin-3-ylamino) quinolin-6-yl)benzonitrile;
4-(4-(4-(4-methylpiperazin-1-yl)phenoxy)quinolin-6-yl) benzonitrile;

6-(4-chlorophenyl)-4-(4-(4-methylpiperazin-1-yl)phenoxy)quinoline;
4-(4-(4-(1-methylpiperidin-4-yl)phenylamino)quinolin-6-yl)benzonitrile;
4-(4-(4-(piperidin-4-yl)phenylamino)quinolin-6-yl)benzonitrile;
N1-(3,6'-biquinolin-4'-yl)-N-4-methyl-N-4-(1-methylpyrrolidin-3-yl)benzene-1,4-diamine;
4-(4-(4-(methyl(1-methylpyrrolidin-3-yl)amino)phenylamino)quinolin-6-yl)benzonitrile; and
N1-methyl-N-4-(6-(5-methylpyridin-2-yl)quinolin-4-yl)-N-1-(1-methylpyrrolidin-3-yl)benzene-1,4-diamine.

40. A pharmaceutical composition comprising at least one pharmaceutically acceptable excipient, and a therapeutically effective amount of a compound of claim 1.

41. The pharmaceutical composition of claim 40, wherein the compound is present in an amount effective for the treatment in a patient of a disease chosen from Alzheimer's disease, stroke, diabetes, obesity, inflammation, and cancer.

42. The pharmaceutical composition of claim 41, wherein inflammation is chosen from Crohn's disease, rheumatoid arthritis, psoriasis, and inflammatory bowel disease.

* * * * *